US012735436B2

(12) United States Patent
Parham

(10) Patent No.: US 12,735,436 B2
(45) Date of Patent: Sep. 15, 2026

(54) MATERIALS FOR ORGANIC ELECTROLUMINESCENT DEVICES

(71) Applicant: UDC IRELAND LIMITED, Dublin (IE)

(72) Inventor: Amir Hossain Parham, Darmstadt (DE)

(73) Assignee: UNIVERSAL DISPLAY COROPRATION, Ewing, NJ (US)

( * ) Notice: Subject to any disclaimer, the term of this patent is extended or adjusted under 35 U.S.C. 154(b) by 964 days.

(21) Appl. No.: 17/912,871

(22) PCT Filed: Mar. 19, 2021

(86) PCT No.: PCT/EP2021/057039

§ 371 (c)(1),
(2) Date: Sep. 20, 2022

(87) PCT Pub. No.: WO2021/191058

PCT Pub. Date: Sep. 30, 2021

(65) Prior Publication Data

US 2023/0337537 A1 Oct. 19, 2023

(30) Foreign Application Priority Data

Mar. 23, 2020 (EP) .................................... 20164893

(51) Int. Cl.

| | |
|---|---|
| ***H10K 85/60*** | (2023.01) |
| ***C07D 487/06*** | (2006.01) |
| ***C07D 487/16*** | (2006.01) |
| ***C07D 498/06*** | (2006.01) |
| ***C07D 498/16*** | (2006.01) |
| ***C07D 513/06*** | (2006.01) |
| ***C07D 513/16*** | (2006.01) |
| ***C07F 5/02*** | (2006.01) |
| ***C09K 11/06*** | (2006.01) |
| ***H10K 50/12*** | (2023.01) |
| ***H10K 101/20*** | (2023.01) |

(52) U.S. Cl.

CPC ............ *C07F 5/027* (2013.01); *C07D 487/06* (2013.01); *C07D 487/16* (2013.01); *C07D 498/06* (2013.01); *C07D 498/16* (2013.01); *C07D 513/06* (2013.01); *C07D 513/16* (2013.01); *C09K 11/06* (2013.01); *H10K 85/657* (2023.02); *H10K 85/6572* (2023.02); *H10K 85/658* (2023.02); *C09K 2211/1018* (2013.01); *H10K 50/121* (2023.02); *H10K 2101/20* (2023.02)

(58) Field of Classification Search

CPC .... C07F 5/027; H10K 85/658; H10K 85/657; H10K 85/6572; C07D 487/06; C07D 487/16; C07D 498/06; C07D 498/16; C07D 513/06; C07D 513/16; C09K 11/06

USPC .................................................... 252/301.16

See application file for complete search history.

(56) References Cited

U.S. PATENT DOCUMENTS

| | | | |
|---|---|---|---|
| 4,539,507 A | 9/1985 | Vanslyke et al. | |
| 2015/0236274 A1 | 8/2015 | Hatakeyama et al. | |
| 2016/0093812 A1 | 3/2016 | Stoessel et al. | |
| 2019/0256538 A1 | 8/2019 | Hatakeyama et al. | |
| 2020/0031827 A1 | 1/2020 | Jatsch et al. | |
| 2020/0176684 A1* | 6/2020 | Lee ........................ | H10K 50/16 |
| 2021/0005821 A1 | 1/2021 | Linge et al. | |

FOREIGN PATENT DOCUMENTS

| | | |
|---|---|---|
| CN | 102869662 A | 1/2013 |
| CN | 104871329 A | 8/2015 |
| CN | 105102581 A | 11/2015 |
| CN | 107501311 A | 12/2017 |
| CN | 109996788 A | 7/2019 |
| WO | 2011/137951 A1 | 11/2011 |
| WO | 2014/094964 A1 | 6/2014 |
| WO | 2014/166586 A1 | 10/2014 |
| WO | 2015/135624 A1 | 9/2015 |
| WO | 2016/128103 A1 | 8/2016 |
| WO | 2018/047639 A1 | 3/2018 |
| WO | 2018/099846 A1 | 6/2018 |

OTHER PUBLICATIONS

International Search Report and Written Opinion received for PCT Patent Application No. PCT/EP2021/057039, mailed on May 17, 2021, 11 pages.

Uoyama et al., "Highly efficient organic light-emitting diodes from delayed fluorescence", Nature, vol. 492, Dec. 13, 2012, pp. 234-238.

* cited by examiner

*Primary Examiner* — Anita Nassiri-Motlagh

(74) *Attorney, Agent, or Firm* — DUANE MORRIS LLP

(57) ABSTRACT

The present invention relates to compounds of the formula (1) which are suitable for use in electronic devices, in particular organic electroluminescent devices, and to electronic device.

20 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2021/057039, filed Mar. 19, 2021, which claims benefit of European Application No. 20164893.8, filed Mar. 23, 2020, both of which are incorporated herein by reference in their entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim is, in particular, the development of compounds with which improved properties of electronic devices in one or more relevant points can be achieved, such as, for example, power efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and also the colour values achieved. In particular, in case of blue-emitting OLEDs, there is potential for improvement with respect to the lifetime, the efficiency of the devices and the colour purity of the emitters.

An important starting point for achieving the said improvements is the choice of the emitter compound and of the host compound employed in the electronic device.

Blue-fluorescent emitters known from the prior art are a multiplicity of compounds. Arylamines containing one or more condensed aryl are very well known from the prior art. Arylamines containing dibenzofuran groups or indenodibenzofuran groups are also known from the prior art.

In the last decade, compounds which exhibit thermally activated delayed fluorescence (TADF) (e.g. H. Uoyama et al., Nature 2012, vol. 492, 234) have also been intensively researched. TADF materials are, in general, organic materials in which the energy gap between the lowest triplet state $T_1$ and the first excited singlet state $S_1$ is sufficiently small so that the $S_1$ state is thermally accessible from the $T_1$ state. For quantum-statistical reasons, on electronic excitation in the OLED, 75% of the excited states are in the triplet state and 25% in the singlet state. Since purely organic molecules cannot usually emit efficiently from the triplet state, 75% of the excited states cannot be utilized for emission, which means that it is possible in principle to convert only 25% of the excitation energy to light. If, however, the energy gap between the lowest triplet state and the lowest excited singlet state is sufficiently small, the first excited singlet state of the molecule is accessible from the triplet state by thermal excitation and can be populated thermally. Since this singlet state is an emissive state from which fluorescence is possible, this state can be used to generate light. Thus, in principle, the conversion of up to 100% of the electrical energy to light is possible when purely organic materials are used as emitter.

Recently, polycyclic aromatic compounds comprising Boron and Nitrogen atoms have been described (for example in US2015/0236274A1, CN107501311A, WO2018/047639A1). These compounds can be used as fluorescent emitters, where the fluorescent emission is mainly prompt fluorescence or as TADF compounds.

However, there is still a need for further fluorescent emitters, especially blue-fluorescent emitters, which may be employed in OLEDs and lead to OLEDs having very good properties in terms of lifetime, colour emission and efficiency. More particularly, there is a need for blue-fluorescent emitters combining very high efficiencies, very good lifetime and suitable colour coordinates as well as high colour purity.

Additionally, organic electroluminescent devices having, in the emitting layer, a TADF compound as a sensitizer and a fluorescent compound having high steric shielding with respect to its environment as an emitter have been recently described (for example in WO2015/135624). This device construction makes it possible to provide organic electroluminescent devices which emit in all emission colours, so that it is possible to use the base structures of known fluorescent emitters which nevertheless exhibit the high efficiency of electroluminescent devices with TADF. This is also known as hyperfluorescence.

As an alternative, the prior art describes organic electroluminescent devices comprising, in the emitting layer, a phosphorescent organometallic complex as a sensitizer, which shows mixing of S1 and T1 states due to the large spin-orbit coupling, and a fluorescent compound as an emitter, so that the emission decay time can significantly be shortened. This is also known as hyperphosphorescence.

Hyperfluorescence and hyperphosphorescence are also promising techniques to improve OLEDs properties, especially in terms of deep blue emission.

However, here too, further improvements are still necessary with respect to the performance data of OLEDs, in particular with a view to broad commercial use, for example in display devices or as light sources. Of particular importance in this connection are the lifetime, the efficiency, the operating voltage of the OLEDs and the colour values achieved, in particular colour purity.

An important starting point for achieving the said improvements in hyperfluorescent and hyperphosphorescent systems is the choice of the fluorescent emitter compound, which might advantageously be a sterically hindered fluorescent emitter compound. For example, sterically hindered fluorescent emitters based on rubrene are described in WO 2015/135624.

Furthermore, it is known that an OLED may comprise different layers, which may be applied either by vapour deposition in a vacuum chamber or by processing from a solution. In case the materials are used for the fabrication a layer applied from a solution, the materials should have good solubility properties in the solution that comprises them.

The present invention is based on the technical object of providing emitters exhibiting prompt fluorescence and/or delayed fluorescence. The present invention is also based on the technical object of providing sterically hindered fluorescent emitters, which can be used in combination with a sensitizer compound in a hyperfluorescent or hyperphosphorescent system. The present invention is also based on the technical object of providing compounds which are suitable for use in electronic devices, such as OLEDs, more particularly as emitters and, which are suitable for vacuum processing or for solution processing.

In investigations on novel compounds for use in electronic devices, it has now been found, that compounds of formula (1) as defined below are eminently suitable for use in electronic devices. In particular, they achieve one or more, preferably all, of the above-mentioned technical objects.

The invention thus relates to compounds of the formula (1), formula (1)

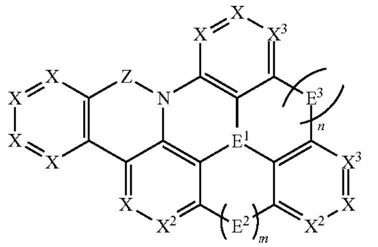

where the following applies to the symbols and indices used:

Z stands, on each occurrence, identically or differently, for C═O, C═S, C═NR, BR, SO or $SO_2$;

$E^1$ stands for N, B, P or P═O;

$E^2$, $E^3$ stand, on each occurrence, identically or differently, for a single bond or for a divalent bridge selected from $B(R^0)$, $N(R^N)$, $C(R^0)_2$, $Si(R^0)_2$, C═O, C═NRN, $C{=}C(R^0)_2$, O, S, S═O, $SO_2$, $P(R^0)$ or $P(=O)R^0$; or a group $E^2$ forms a lactam ring (L-1) as depicted below with one group $X^2$, or a group $E^3$ forms a lactam ring (L-1) with one group $X^3$;

(L-1)

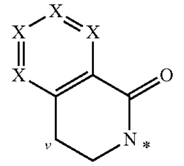

where the sign "v" indicates the position of the group $X^2$ or $X^3$, which stands for C in this case, and the N atom marked with the sign "*" corresponds to $E^2$ or $E^3$;

X stands, on each occurrence, identically or differently, for $CR^1$ or N;

$X^2$, $X^3$ stand, on each occurrence, identically or differently, for X;

$R^0$, $R^1$, $R^N$ stand on each occurrence, identically or differently, for H, D, F, Cl, Br, I, CHO, CN, C(═O)Ar, $P(=O)(Ar)_2$, S(═O)Ar, $S(=O)_2Ar$, $N(R)_2$, $N(Ar)_2$, $NO_2$, $Si(R)_3$, $B(OR)_2$, $OSO_2R$, a straight-chain alkyl, alkoxy or thioalkyl group having 1 to 40 C atoms or branched or a cyclic alkyl, alkoxy or thioalkyl group having 3 to 40 C atoms, each of which may be substituted by one or more radicals R, where in each case one or more non-adjacent $CH_2$ groups may be replaced by RC═CR, C≡C, $Si(R)_2$, $Ge(R)_2$, $Sn(R)_2$, C═O, C═S, C═Se, P(═O)(R), SO, $SO_2$, O, S or CONR and where one or more H atoms may be replaced by D, F, Cl, Br, I, CN or $NO_2$, an aromatic or heteroaromatic ring system having 5 to 60 aromatic ring atoms, which may in each case be substituted by one or more radicals R, an aralkyl or heteroaralkyl group having 5 to 60 aromatic ring atoms, which may be substituted by one or more R radicals, or an aryloxy or heteroaryloxy group having 5 to 60 aromatic ring atoms, which may be substituted by one or more radicals R; where two radicals $R^0$, $R^1$, $R^N$ may form an aliphatic, aromatic or heteroaromatic ring system together, which may be substituted by one or more radicals R;

R stands on each occurrence, identically or differently, for H, D, F, Cl, Br, I, CHO, CN, C(═O)Ar, $P(=O)(Ar)_2$, S(═O)Ar, $S(=O)_2Ar$, $N(R')_2$, $N(Ar)_2$, $NO_2$, $Si(R')_3$, $B(OR')_2$, $OSO_2R'$, a straight-chain alkyl, alkoxy or thioalkyl group having 1 to 40 C atoms or branched or a cyclic alkyl, alkoxy or thioalkyl group having 3 to 40 C atoms, each of which may be substituted by one or more radicals R', where in each case one or more non-adjacent $CH_2$ groups may be replaced by R'C═CR', C═C, $Si(R')_2$, $Ge(R')_2$, $Sn(R')_2$, C═O, C═S, C═Se, P(═O)(R'), SO, $SO_2$, O, S or CONR' and where one or more H atoms may be replaced by D, F, Cl, Br, I, CN or $NO_2$, an aromatic or heteroaromatic ring system having 5 to 60 aromatic ring atoms, which may in each case be substituted by one or more radicals R'; where two substituents R may form an aliphatic or aromatic ring system together, which may be substituted by one or more radicals R';

Ar is, on each occurrence, identically or differently, an aromatic or heteroaromatic ring system having 5 to 60 aromatic ring atoms, which may in each case also be substituted by one or more radicals R';

R' stands on each occurrence, identically or differently, for H, D, F, Cl, Br, I, CN, a straight-chain alkyl, alkoxy or thioalkyl group having 1 to 20 C atoms or branched or cyclic alkyl, alkoxy or thioalkyl group having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 aromatic ring atoms;

m, n are, identically or differently, 0 or 1; with the proviso that m+n=1, and when m is 0, then $E^2$ is absent and a group X is present at each bonding site of $E^2$, and when n is 0, then $E^3$ is absent and a group X is present at each bonding site of $E^3$.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aralkyl group in accordance with the definition of the present invention is taken to mean an alkyl group, where at least one hydrogen atom is replaced by an aryl group. An analogous definition applies to heteroaralkyl groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom.

The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphtha-cene, pentacene, benzopyrene, biphenyl, biphenylene, terphenyl, terphenyl-ene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoro-methyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoro-methylthio, pentafluoroethylthio, 2,2,2-trifluoroethylthio, ethenylthio, propenyl-thio, butenylthio, pentenylthio, cyclopentenylthio, hexenylthio, cyclohexenylthio, heptenylthio, cycloheptenylthio, octenylthio, cyclooctenyl-thio, ethynylthio, propynylthio, butynylthio, pentynylthio, hexynylthio, heptynyl-thio or octynylthio.

The formulation that two or more radicals may form a ring with one another is, for the purposes of the present application, intended to be taken to mean, inter alia, that the two radicals are linked to one another by a chemical bond. This is illustrated by the following schemes:

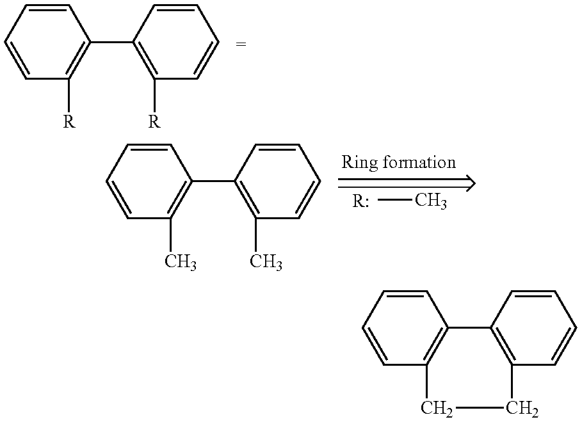

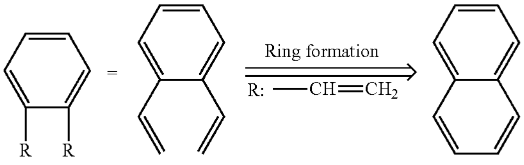

Furthermore, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

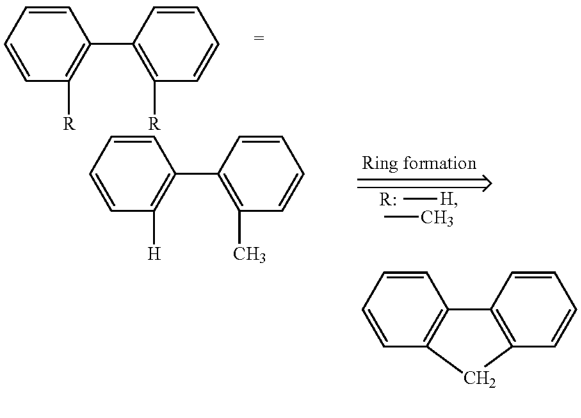

Adjacent substituents in the sense of the present invention are substituents which are bonded to atoms which are linked directly or via 1, 2, 3 or 4 atoms to one another or which are bonded to the same atom.

Preferably, $E^1$ stands for N or B.

In accordance with the invention, $E^2$, $E^3$ stand, on each occurrence, identically or differently, for a single bond or for a divalent bridge selected from $B(R^0)$, $N(R^N)$, $C(R^0)_2$, $Si(R^0)_2$, C=O, C=NRN, $C{=}C(R^0)_2$, O, S, S=O, $SO_2$, $P(R^0)$ or $P(=O)R^0$; or a group $E^2$ forms a lactam ring (L-1) as depicted above with one group $X^2$, or a group $E^3$ forms a lactam ring (L-1) with one group $X^3$. Preferably, the groups $E^2$ and $E^3$ stand, on each occurrence, identically or differently, for a divalent bridge selected from $B(R^0)$, $N(R^N)$, $C(R^0)_2$, O or S, or a group $E^2$ forms a lactam ring (L-1) as depicted above with a group $X^2$, or a group $E^3$ forms a lactam ring (L-1) with a group $X^3$.

In accordance with a preferred embodiment, the compounds of formula (1) comprise at least one group $E^2$ or $E^3$, which stands for a divalent bridge selected from $B(R^0)$, $N(R^N)$, $C(R^0)_2$, $Si(R^0)_2$, C=O, C=NRN, $C{=}C(R^0)_2$, O, S, S=O, $SO_2$, $P(R^0)$ or $P(=O)R^0$ or at least one group $E^2$ or $E^3$ forms a lactam ring (L-1) as depicted above with one group $X^2$ or one group $X^3$. More preferably, the compounds of formula (1) comprise at least one group $E^2$ or $E^3$, which stands for a divalent bridge selected from $N(R^N)$ or forms a lactam ring (L-1) as depicted above with a group $X^2$ or $X^3$.

Preferably, the group Z stands, on each occurrence, identically or differently, for C=O or C=S, more preferably for C=O.

Preferably, the compounds of formula (1) are selected from the compounds of formula (1A) or (1B), formula (1A)

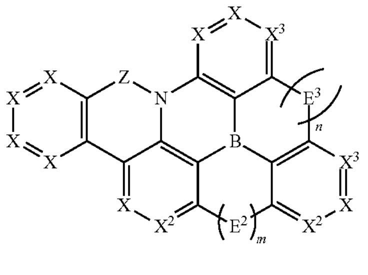

formula (1B)

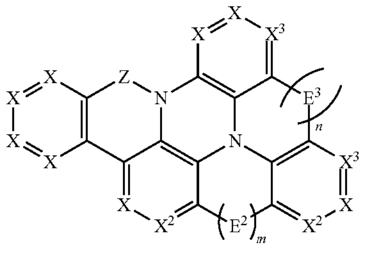

where the symbols have the same meaning as above.

More preferably, the compounds of formula (1) are selected from the compounds of formula (2A) or (2B), formula (2A)

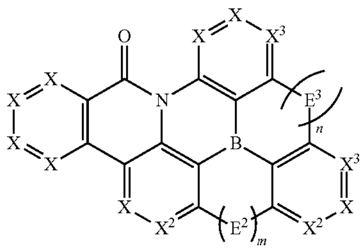

formula (2B)

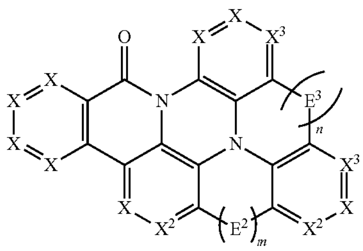

where the symbols have the same meaning as above.

Even more preferably, the compounds of formula (1) are selected from the compounds of formulae (2A-1) to (2B-3), formula (2A-1)

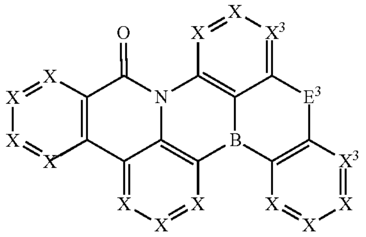

formula (2A-2)

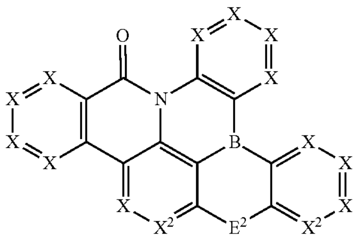

formula (2A-3)

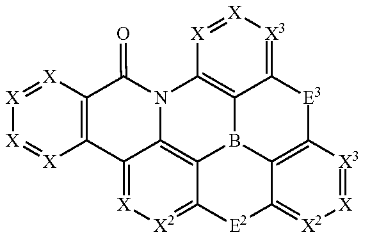

-continued formula (2B-1)

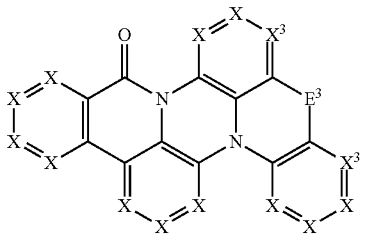

formula (2B-2)

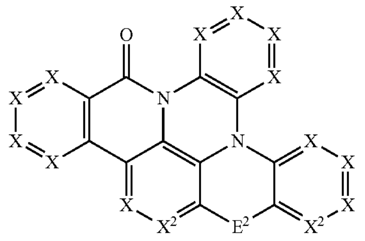

formula (2B-3)

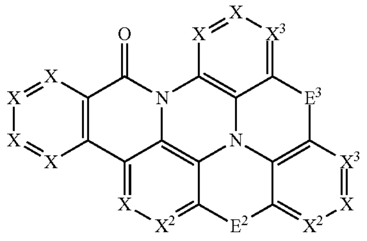

where the symbols have the same meaning as above.

Particularly preferably, the compounds of formula (1) are selected from compounds of formulae (2A-1-1) to (2-A-3-6), formula (2A-1-1)

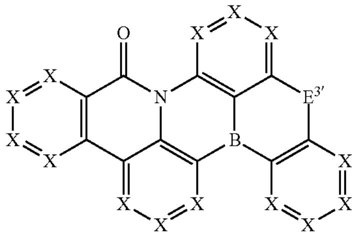

formula (2A-1-2)

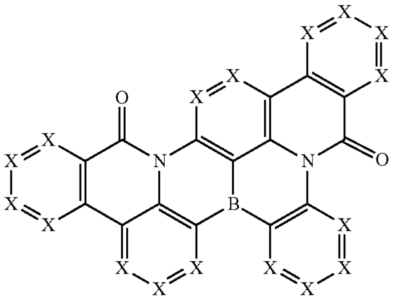

formula (2A-1-3)
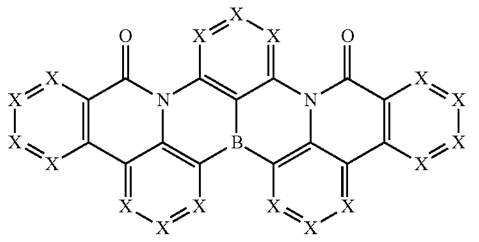
formula (2A-2-1)
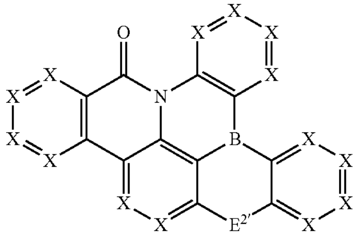
formula (2A-2-2)
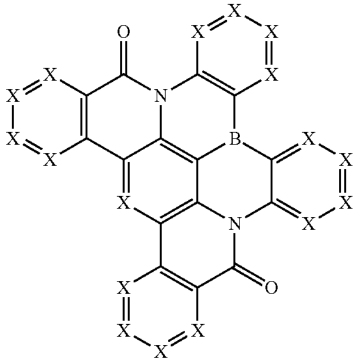
formula (2A-2-3)
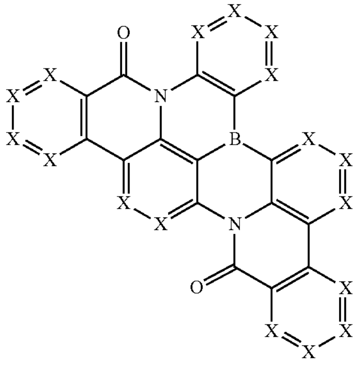
formula (2A-3-1)
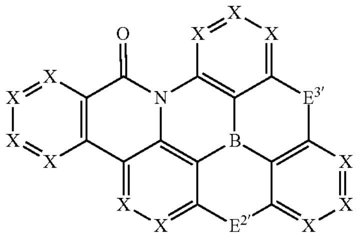
formula (2A-3-2)
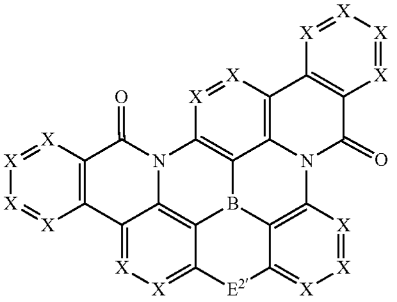
formula (2A-3-3)
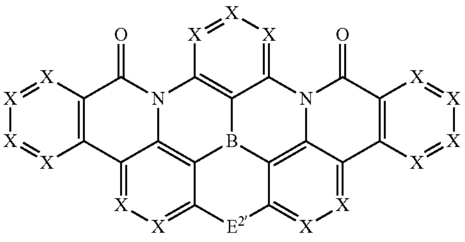
formula (2A-3-4)
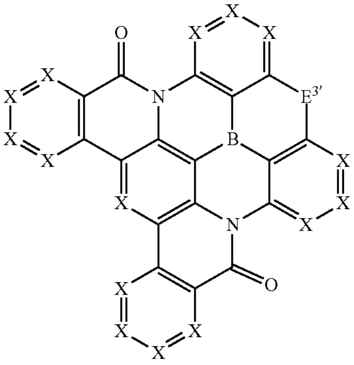
formula (2A-3-5)
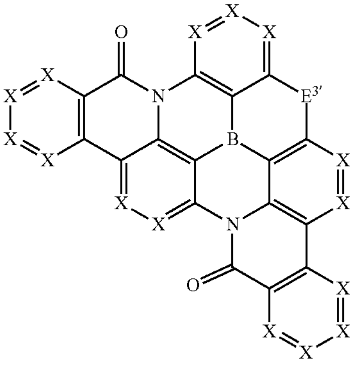

-continued
formula (2A-3-6)
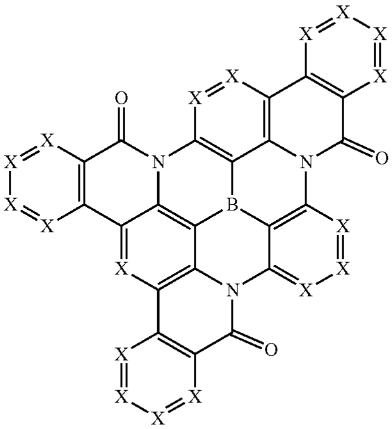
formula (2B-1-1)
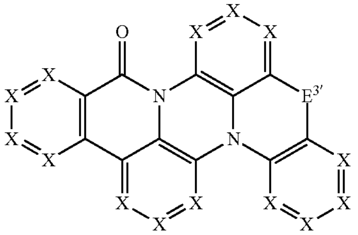
formula (2B-1-2)
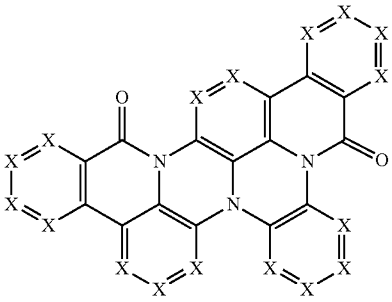
formula (2B-1-3)
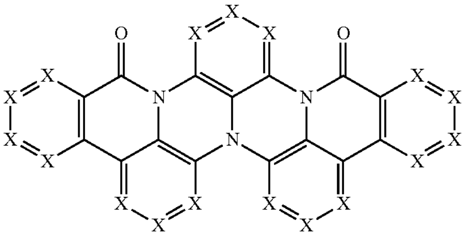
formula (2B-2-1)
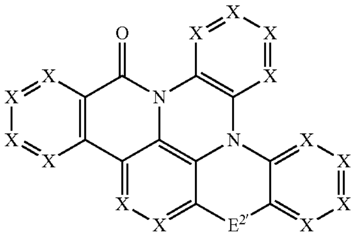
-continued
formula (2B-2-2)
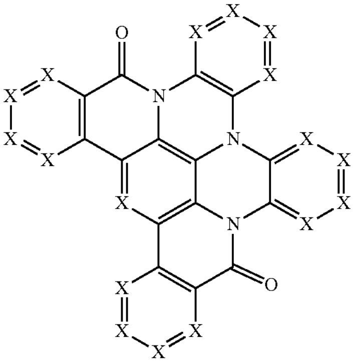
formula (2B-2-3)
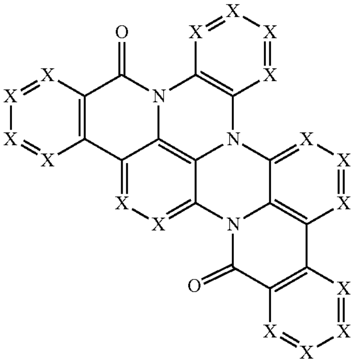
formula (2B-3-1)
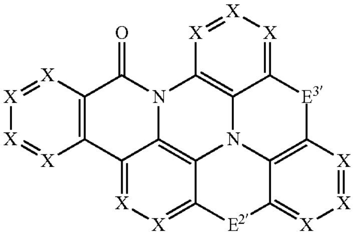
formula (2B-3-2)
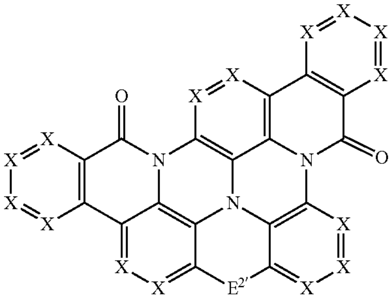
formula (2B-3-3)
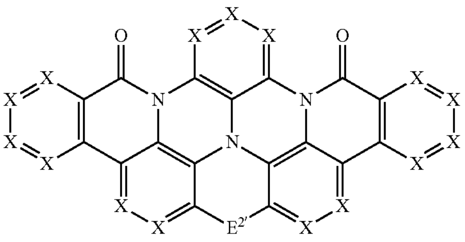

-continued formula (2B-3-4)

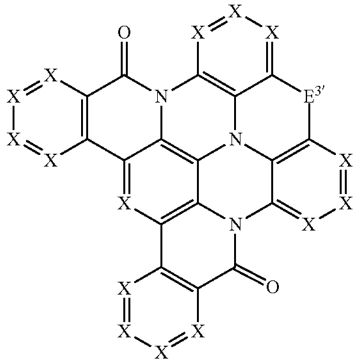

formula (2B-3-5)

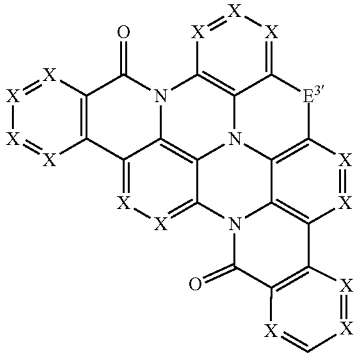

formula (2B-3-6)

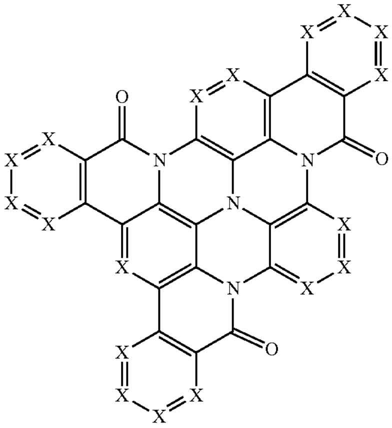

where X has the same meaning as above and where $E^{2'}$, $E^{3'}$ stand, on each occurrence, identically or differently, for a single bond or for a divalent bridge selected from $B(R^0)$, $N(R^N)$, $C(R^0)_2$, $Si(R^0)_2$, C═O, C═NRN, $C═C(R^0)_2$, O, S, S═O, $SO_2$, $P(R^0)$ or $P(═O)R^0$.

Preferably, $E^{2'}$, $E^{3'}$ stand, on each occurrence, identically or differently, for a divalent bridge selected from $B(R^0)$, $N(R^N)$, $C(R^0)_2$, O or S.

In accordance with a preferred embodiment, the compounds of formula (1) comprise at least one radical $R^0$, $R^1$, $R^N$ or R, which is selected from the following groups of formulae (RS-a) to (RS-e):

branched or cyclic alkyl groups represented by the general following formula a group of formula (RS-a), (RS-a)

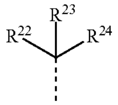

wherein $R^{22}$, $R^{23}$, $R^{24}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{25}$, and where two of radicals $R^{22}$, $R^{23}$, $R^{24}$ or all radicals $R^{22}$, $R^{23}$, $R^{24}$ may be joined to form a (poly)cyclic alkyl group, which may be substituted by one or more radicals $R^{25}$;

$R^{25}$ is at each occurrence, identically or differently, selected from a straight-chain alkyl group having 1 to 10 carbon atoms, or a branched or cyclic alkyl group having 3 to 10 carbon atoms;

with the proviso that at each occurrence at least one of radicals $R^{22}$, $R^{23}$ and $R^{24}$ is other than H, with the proviso that at each occurrence all of radicals $R^{22}$, $R^{23}$ and $R^{24}$ together have at least 4 carbon atoms and with the proviso that at each occurrence, if two of radicals $R^{22}$, $R^{23}$, $R^{24}$ are H, the remaining radical is not a straight-chain; or branched or cyclic alkoxy groups represented by the general following formula (RS-b)

(RS-b)

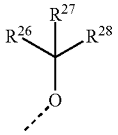

wherein $R^{26}$, $R^{27}$, $R^{28}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{25}$ as defined above, and where two of radicals $R^{26}$, $R^{27}$, $R^{28}$ or all radicals $R^{26}$, $R^{27}$, $R^{28}$ may be joined to form a (poly)cyclic alkyl group, which may be substituted by one or more radicals $R^{25}$ as defined above;

with the proviso that at each occurrence only one of radicals $R^{26}$, $R^{27}$ and $R^{28}$ may be H;

aralkyl groups represented by the general following formula (RS-c)

(RS-c)

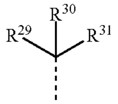

wherein $R^{29}$, $R^{30}$, $R^{31}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{32}$, or an aromatic ring system having 6 to 30 aromatic ring atoms, which may in each case be substituted by one or more radicals $R^{32}$, and where two or all of radicals $R^{29}$, $R^{30}$, $R^{31}$ may be joined to form a (poly)cyclic alkyl group or an aromatic ring system, each of which may be substituted by one or more radicals $R^{32}$;

$R^{32}$ is at each occurrence, identically or differently, selected from a straight-chain alkyl group having 1 to 10 carbon atoms, or a branched or cyclic alkyl group having 3 to 10 carbon atoms, or an aromatic ring system having 6 to 24 aromatic ring atoms;

with the proviso that at each occurrence at least one of radicals $R^{29}$, $R^{30}$ and $R^{31}$ is other than H and that at each occurrence at least one of radicals $R^{29}$, $R^{30}$ and $R^{31}$ is or contains an aromatic ring system having at least 6 aromatic ring atoms;

aromatic ring systems represented by the general formula (RS-d)

(RS-d)

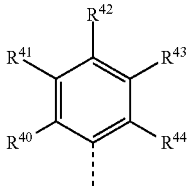

wherein $R^{40}$ to $R^{44}$ is at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{32}$, or an aromatic ring system having 6 to 30 aromatic ring atoms, which may in each case be substituted by one or more radicals $R^{32}$, and where two or more of radicals $R^{40}$ to $R^{44}$ may be joined to form a (poly)cyclic alkyl group or an aromatic ring system, each of which may be substituted by one or more radicals $R^{32}$ as defined above; or groups of formula (RS-e), formula (RS-e)

$$---(Ar^{50})_m—Ar^{51}$$

where the dashed bond in formula (RS-e) indicates the bonding to the compound, where $Ar^{50}$, $Ar^{51}$ stand on each occurrence, identically or differently, for an aromatic or heteroaromatic ring systems having 5 to 60 aromatic ring atoms, which may in each case be substituted by one or more radicals R; and where m is an integer selected from 1 to 10.

Examples of suitable groups of formulae (RS-a) to (RS-d) are the groups (RS-1) to (RS-78):

(RS-1)

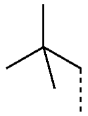

-continued (RS-2)

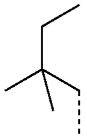

(RS-3)

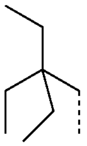

(RS-4)

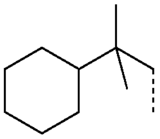

(RS-5)

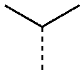

(RS-6)

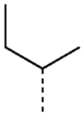

(RS-7)

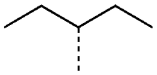

(RS-8)

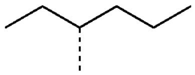

(RS-9)

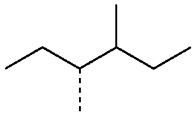

(RS-10)

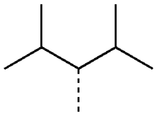

(RS-11)

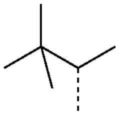

(RS-12)

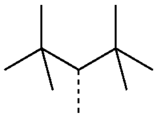

(RS-13)

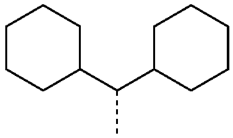

(RS-14)

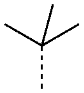

-continued
(RS-15)
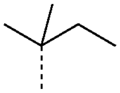
(RS-16)
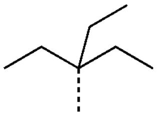
(RS-17)
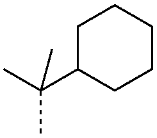
(RS-18)
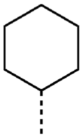
(RS-19)
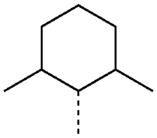
(RS-20)
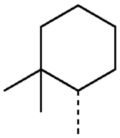
(RS-21)
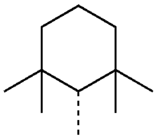
(RS-22)
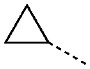
(RS-23)
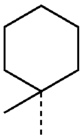
(RS-24)
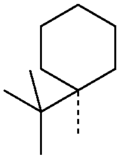
(RS-25)
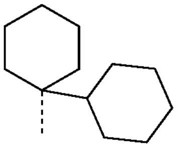
-continued
(RS-26)
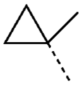
(RS-27)
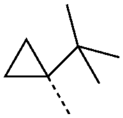
(RS-28)
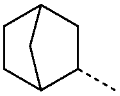
(RS-29)
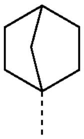
(RS-30)
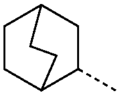
RS-31)
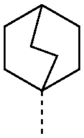
(RS-32)
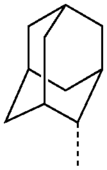
(RS-33)
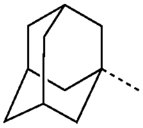
(RS-34)
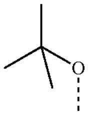
(RS-35)
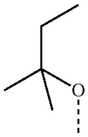
(RS-36)
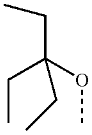

-continued
(RS-37)
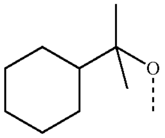
(RS-38)
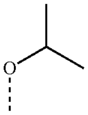
(RS-39)
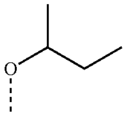
(RS-40)
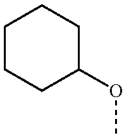
(RS-41)
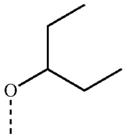
(RS-42)
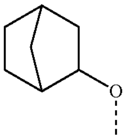
(RS-43)
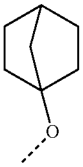
(RS-44)
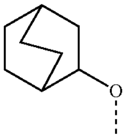
(RS-45)
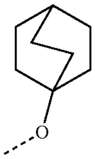
(RS-46)
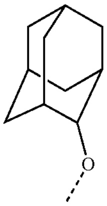
-continued
(RS-47)
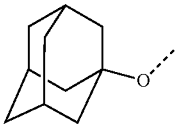
(RS-48)
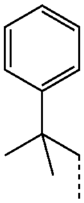
(RS-49)
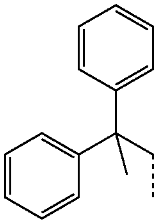
(RS-50)
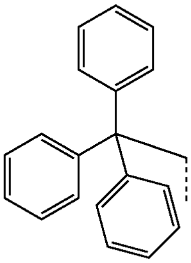
(RS-51)
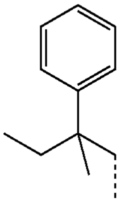
(RS-52)
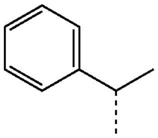
(RS-53)
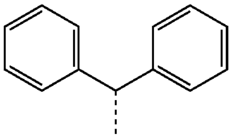
(RS-54)
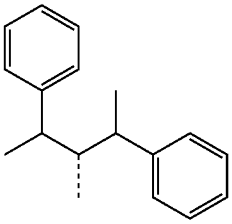

-continued
(RS-55)
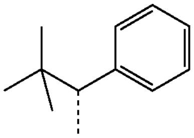
(RS-56)
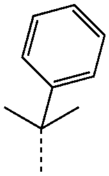
(RS-57)
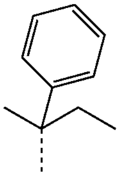
(RS-58)
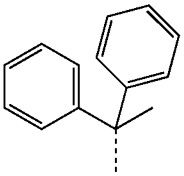
(RS-59)
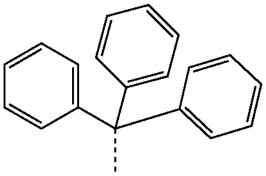
(RS-60)
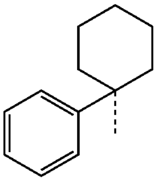
(RS-61)
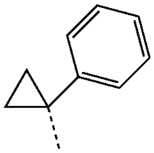
(RS-62)
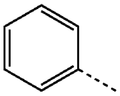
(RS-63)
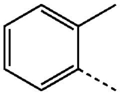
(RS-64)
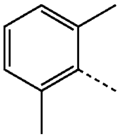
-continued
(RS-65)
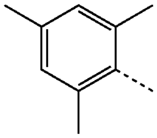
(RS-66)
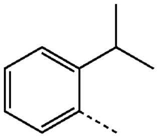
(RS-67)
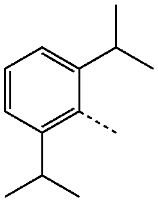
(RS-68)
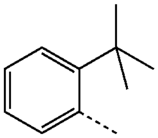
(RS-69)
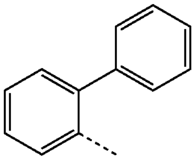
(RS-70)
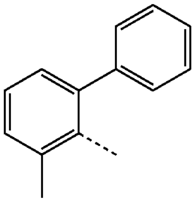
(RS-71)
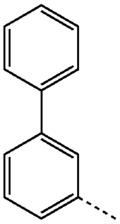
(RS-72)
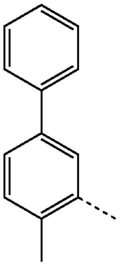

-continued (RS-73)

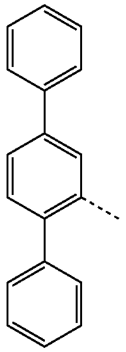

(RS-74)

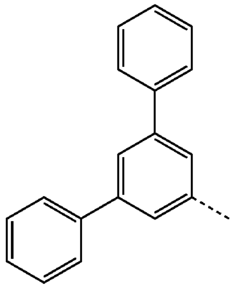

(RS-75)

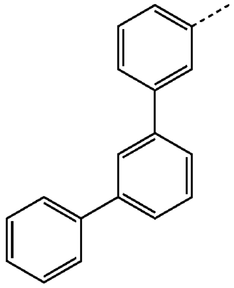

(RS-76)

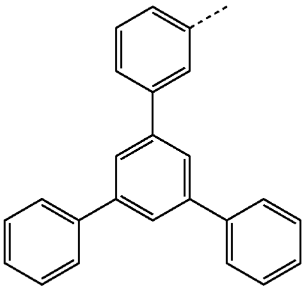

(RS-77)

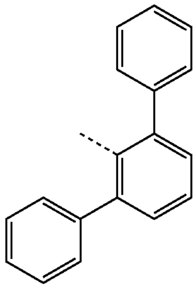

-continued (RS-78)

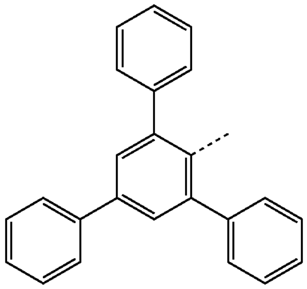

where the dashed bond indicates the bonding of these groups to the structure of formula (1) and where the groups of formulae (RS-1) to (RS-47) may further be substituted by a least one group $R^{25}$ as defined above and groups (RS-48) to (RS-78) may further be substituted by a least one group $R^{32}$ as defined above.

Preferably, the index m in the group of formula (RS-e) is an integer selected from 1 to 6, very preferably from 1 to 4, very more preferably from 1 and 2.

In formula (RS-e), it is preferred that the group $Ar^{50}$ is selected from the groups of formulae (Ar50-1) to (Ar50-19), (Ar50-1)

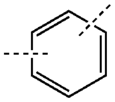

(Ar50-2)

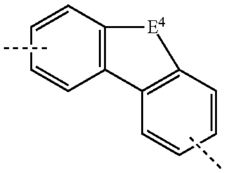

(Ar50-3)

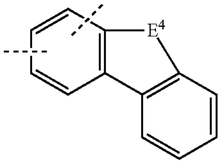

(Ar50-4)

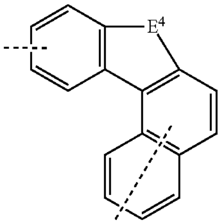

(Ar50-5)

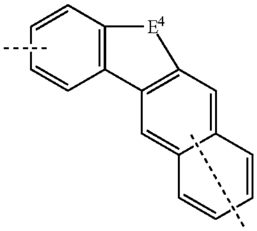

-continued (Ar50-6)

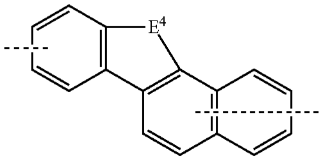

(Ar50-7)

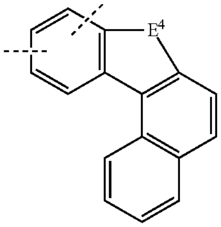

(Ar50-8)

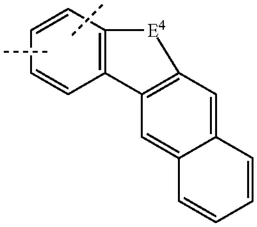

(Ar50-9)

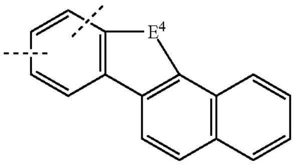

(Ar50-10)

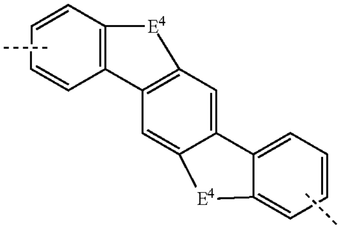

(Ar50-11)

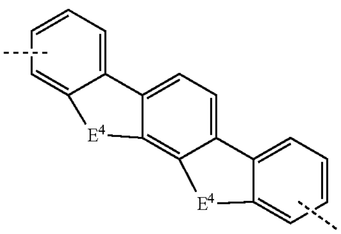

(Ar50-12)

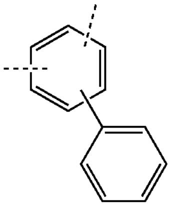

-continued (Ar50-13)

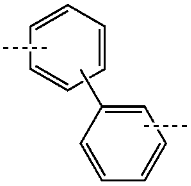

(Ar50-14)

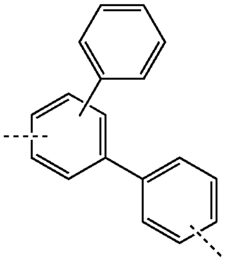

(Ar50-15)

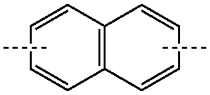

(Ar50-16)

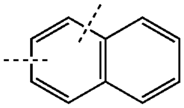

(Ar50-17)

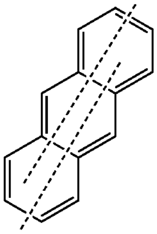

(Ar50-18)

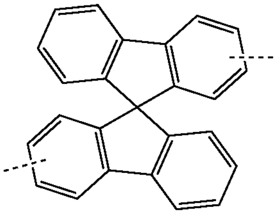

(Ar50-19)

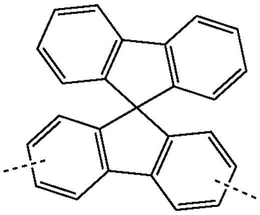

where the dashed bonds indicate the bonding to the structure of formula (1) and to a group $Ar^{50}$ or $Ar^{51}$ and the groups of formulae (Ar50-1) to (Ar50-19) may be substituted at each free position by a group R, which has the same meaning as above and where:

$E^4$ is selected from —B($R^{0-}$), —C($R^0$)$_2$—, —C($R^0$)$_2$—C(R)$_2$—, —Si(R)$_2$—, —C(═O)—, —C(═N$R^0$)—, —C═(C($R^0$))$_2$—, —O—, —S—, —S(═O)—, —$SO_2$—, —N($R^0$)—, —P($R^0$)— and —P((═O)

$R^0$)—, preferably from —C($R^0$)$_2$—, —Si($R^0$)$_2$—, —O—, —S— or —N($R^0$)—; and
$R^0$ has the same definition as above.
It is also preferred that the group $Ar^{51}$ is selected from the groups of formulae (Ar51-1) to (Ar51-15),
(Ar51-1)
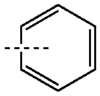
(Ar51-2)
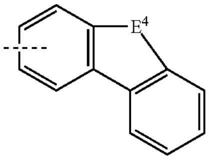
(Ar51-3)
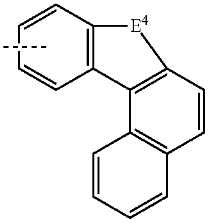
(Ar51-4)
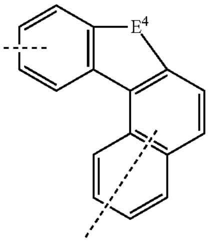
(Ar51-5)
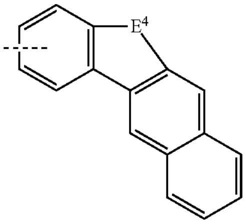
(Ar51-6)
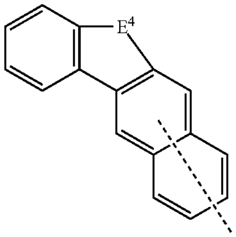
(Ar51-7)
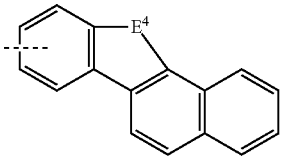
-continued
(Ar51-8)
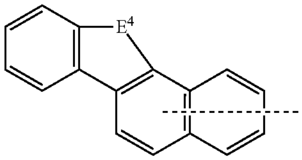
(Ar51-9)
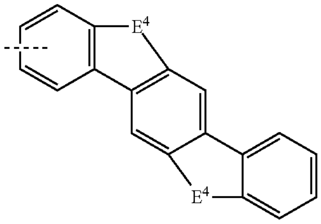
(Ar51-10)
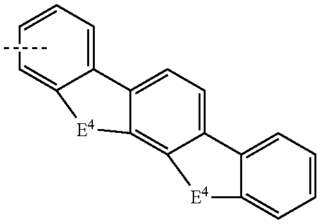
(Ar51-11)
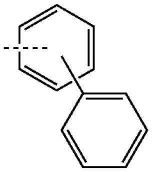
(Ar51-12)
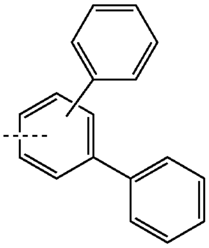
(Ar51-13)
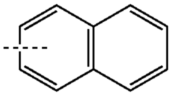
(Ar51-14)
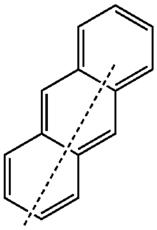

-continued (Ar51-15)

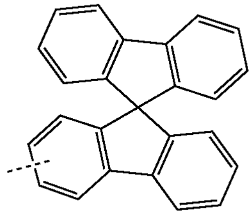

where the dashed bond indicates the bonding to $Ar^{50}$ and where $E^4$ has the same meaning as above and the groups of formulae (Ar51-1) to (Ar51-15) may be substituted at each free position by a group R, which has the same meaning as above.

In accordance with a preferred embodiment at least one group $Ar^{50}$ in formula (RS-e) stands for a group of formula (Ar50-2) and/or at least one group $Ar^3$ stands for a group of formula (Ar51-2), (Ar50-2)

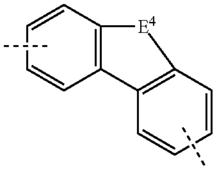

(Ar51-2)

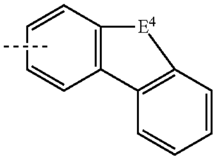

where the dashed bonds in formula (Ar50-2) indicate the bonding to the structure of formula (1) and to a group $Ar^{50}$ or $Ar^{51}$; and the dashed bond in formula (Ar51-2) indicates the bonding to $Ar^{50}$;

$E^4$ has the same meaning as above; and the groups of formulae (Ar50-2) and (Ar51-2) may be substituted at each free position by a group R, which has the same meaning as above.

In accordance with a very preferred embodiment, at least one group $Ar^{50}$ stands for a group of formula (Ar50-2-1) and/or at least one group $Ar^{51}$ stands for a group of formula (Ar51-2-1), (Ar50-2-1)

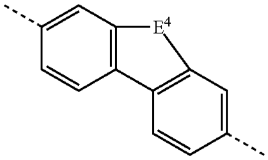

(Ar51-2-1)

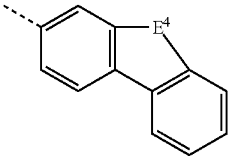

where the dashed bonds in formula (Ar50-2-1) indicate the bonding to the structure of formula (1) and to a group $Ar^{50}$ or $Ar^{51}$;

the dashed bond in formula (Ar51-2-1) indicates the bonding to $Ar^{50}$;

$E^4$ has the same meaning as above; and the groups of formulae (Ar50-2-1) and (Ar51-2-1) may be substituted at each free position by a group R, which has the same meaning as above.

In accordance with a particularly preferred embodiment, at least one group $Ar^{50}$ stands for a group of formula (Ar50-2-1b) and/or at least one group $Ar^{51}$ stands for a group of formula (Ar51-2-1b), (Ar50-2-1b)

(Ar51-2-1b)

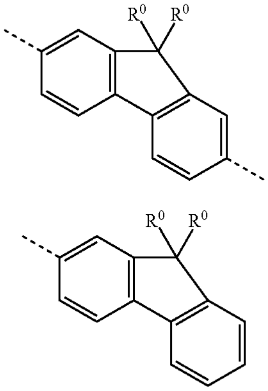

where the dashed bonds in formula (Ar50-2-1b) indicate the bonding to the structure of formula (1) and to a group $Ar^{50}$ or $Ar^{51}$;

the dashed bond in formula (Ar51-2-1b) indicates the bonding to $Ar^{50}$;

$R^0$ has the same meaning as above; and the groups of formulae (Ar50-2-1b) and (Ar51-2-1b) may be substituted at each free position by a group R, which has the same meaning as above.

Preferably, the group $R^0$ stands on each occurrence, identically or differently, for H, D;

for a straight-chain alkyl group having 1 to 20, preferably 1 to 10 carbon atoms, a branched or cyclic alkyl group having 3 to 20, preferably 3 to 10 carbon atoms, each of which may be substituted by one or more radicals R;

for an aromatic or heteroaromatic ring system having 5 to 60, preferably 5 to 40, more preferably 5 to 30, very preferably 5 to 18 aromatic ring atoms, which may in each case be substituted by one or more radicals R; or for a group of formula (RS-a), (RS-b), (RS-c), (RS-d) or (RS-e) as defined above;

where two adjacent radicals $R^0$ may form an aliphatic, aromatic or heteroaromatic ring system together, which may be substituted by one or more radicals R.

Very preferably, the group $R^0$ stands on each occurrence, identically or differently, for H;

for a straight-chain alkyl group having 1 to 10, preferably 1 to 5 carbon atoms, a branched or cyclic alkyl group having 3 to 10, preferably 3 to 5 carbon atoms, each of which may be substituted by one or more radicals R; or for an aromatic or heteroaromatic ring system having 5 to 18 aromatic ring atoms, which may in each case be substituted by one or more radicals R; where two adjacent radicals $R^0$ may form an aliphatic, aromatic or heteroaromatic ring system together, which may be substituted by one or more radicals R.

When two adjacent radicals $R^0$ form a ring system together, they preferably form a ring of formula ($R^0$-1), ($R^0$-1)

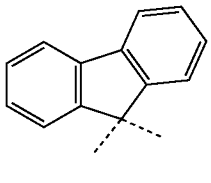

where the group of formula ($R^0$-1) may be substituted by one or more radicals R and where the dashed bonds indicate the bonding to the structure of formula (1).

Preferably, $R^1$ stands on each occurrence, identically or differently, for H, D, F, Cl, Br, I, CN or $N(Ar)_2$, for a straight-chain alkyl, alkoxy or thioalkyl group having 1 to 40, preferably 1 to 20, more preferably 1 to 10 C atoms or for a branched or cyclic alkyl, alkoxy or thioalkyl group having 3 to 40, preferably 3 to 20, more preferably 3 to 10 C atoms, each of which may be substituted by one or more radicals R, where in each case one or more non-adjacent $CH_2$ groups may be replaced by RC═CR, C≡C, $Si(R)_2$, $Ge(R)_2$, $Sn(R)_2$, C═O, C═S, C═Se, P(═O)(R), SO, $SO_2$, O, S or CONR and where one or more H atoms may be replaced by D, F, Cl, Br, I, CN or $NO_2$;

for an aromatic or heteroaromatic ring system having 5 to 60, preferably 5 to 40, more preferably 5 to 30, very preferably 5 to 18 aromatic ring atoms, which may in each case be substituted by one or more radicals R; or for a group of formula (RS-a), (RS-b), (RS-c), (RS-d) or (RS-e) as defined above;

where two adjacent radicals $R^1$ may form an aliphatic, aromatic or heteroaromatic ring system together, which may be substituted by one or more radicals R.

More preferably, $R^1$ stands on each occurrence, identically or differently, for H, D, F or CN;

for a straight-chain alkyl or alkoxy group having 1 to 40, preferably 1 to 20, more preferably 1 to 10 C atoms or for a branched or cyclic alkyl or alkoxy group having 3 to 40, preferably 3 to 20, more preferably 3 to 10 C atoms, each of which may be substituted by one or more radicals R, and where one or more H atoms may be replaced by D or F;

for an aromatic or heteroaromatic ring system having 5 to 60, preferably 5 to 40, more preferably 5 to 30, very preferably 5 to 18 aromatic ring atoms, which may in each case be substituted by one or more radicals R; or for a group of formula (RS-a), (RS-b), (RS-c), (RS-d) or (RS-e) as defined above;

where two adjacent radicals $R^1$ may form an aliphatic, aromatic or heteroaromatic ring system together, which may be substituted by one or more radicals R.

Examples of very suitable radicals $R^1$ are H, D, F, CN, substituted and unsubstituted straight-chain alkyl groups having 1 to 10 C atoms, more particularly, methyl, ethyl, propyl, butyl, substituted and unsubstituted branched or cyclic alkyl groups having 3 to 10 C atoms, more particularly t-butyl, and groups of formulae (Ar1-1) to (Ar1-24), (Ar1-1)

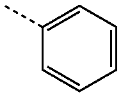

(Ar1-2)

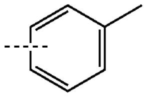

(Ar1-3)

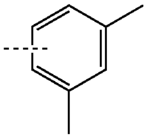

(Ar1-4)

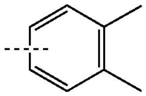

(Ar1-5)

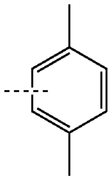

(Ar1-6)

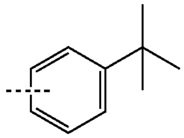

(Ar1-7)

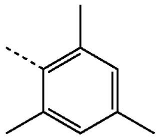

(Ar1-8)

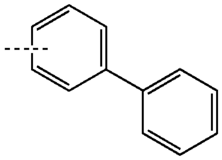

(Ar1-9)

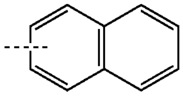

(Ar1-10)

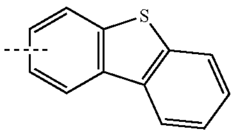

(Ar1-11)

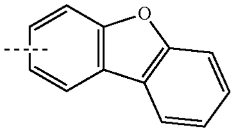

-continued
(Ar1-12)
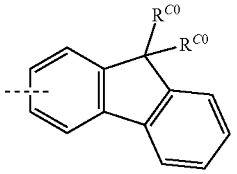
(Ar1-13)
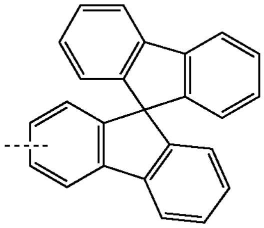
(Ar1-14)
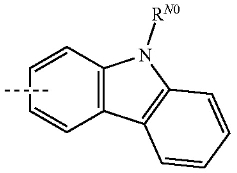
(Ar1-15)
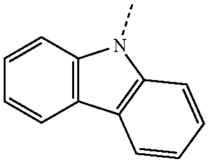
(Ar1-16)
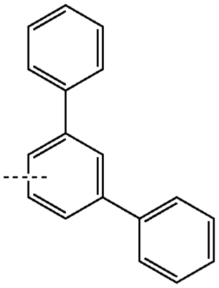
(Ar1-17)
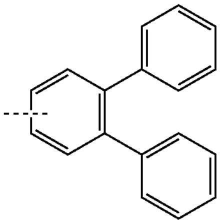
-continued
(Ar1-18)
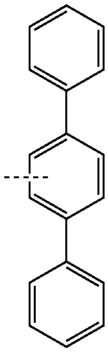
(Ar1-19)
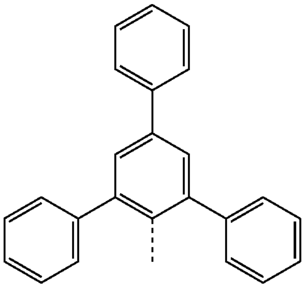
(Ar1-20)
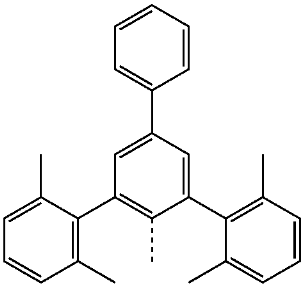
(Ar1-21)
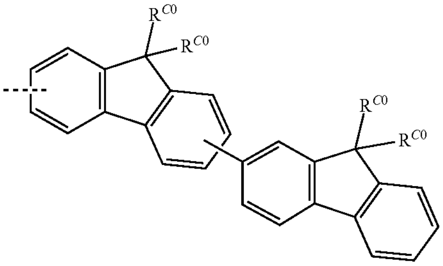
(Ar1-22)
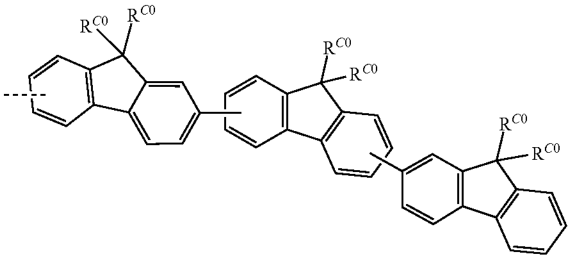

-continued (Ar1-23)

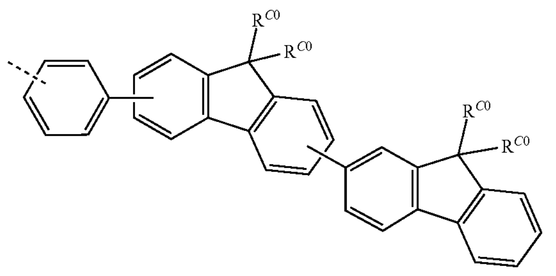

(Ar1-24)

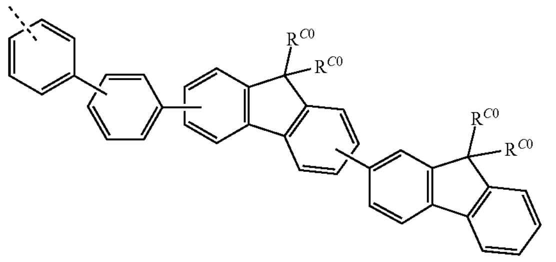

where in formulae (Ar1-1) to (Ar1-24):

the dashed bond indicates the bonding of the radical to the rest of the structure;

$R^{N0}$, $R^{C0}$ are on each occurrence, identically or differently, H, D, F, Cl, Br, I, CN, a straight-chain alkyl, alkoxy or thioalkoxy group having 1 to 40, preferably 1 to 20, more preferably 1 to 10 C atoms or cyclic alkyl, alkoxy or thioalkoxy group having 3 to 40, preferably 3 to 20, more preferably 3 to 10 C atoms, each of which may be substituted by one or more radicals R, where one or more non-adjacent $CH_2$ groups may be replaced by (R)C═C(R), C≡C, O or S and where one or more H atoms may be replaced by D, F, Cl, Br, I, CN or $NO_2$, or an aromatic or heteroaromatic ring system having 5 to 60, preferably 5 to 40, more preferably 5 to 30, very more preferably 5 to 18 aromatic ring atoms, which may in each case be substituted by one or more radicals R, where optionally two adjacent radicals $R^{C0}$ can form a mono- or polycyclic, aliphatic, aromatic or heteroaromatic ring system with one another;

the groups of formulae (Ar1-1) to (Ar1-24) may be substituted at each free position by a group R, which has the same meaning as above.

Preferably, $R^N$ stands on each occurrence, identically or differently, for H, D;

for a straight-chain alkyl group having 1 to 40, preferably 1 to 20, more preferably 1 to 10 C atoms or a branched or cyclic alkyl group having 3 to 40, preferably 3 to 20, more preferably 3 to 10 C atoms, each of which may be substituted by one or more radicals R, where in each case one or more non-adjacent $CH_2$ groups may be replaced by RC═CR, C≡C, O or S and where one or more H atoms may be replaced by D or F;

for an aromatic or heteroaromatic ring system having 5 to 60, preferably 5 to 40, more preferably 5 to 30, very preferably 5 to 18 aromatic ring atoms, which may in each case be substituted by one or more radicals R; or for a group of formula (RS-a), (RS-b), (RS-c), (RS-d) or (RS-e) as defined above.

More preferably, $R^N$ stands on each occurrence, identically or differently, for an aromatic or heteroaromatic ring system having 5 to 30, preferably 5 to 18 aromatic ring atoms, preferably selected from the group consisting of phenyl, biphenyl, terphenyl, quaterphenyl, fluorene, spirobifluorene, naphthalene, anthracene, phenanthrene, triphenylene, fluoranthene, indole, benzofuran, benzothiophene, dibenzofuran, dibenzothiophene, carbazole, indenocarbazole, indolocarbazole, phenanthroline, pyridine, pyrimidine, pyrazine, pyridazine, triazine, quinolone, benzopyridine, benzopyridazine, benzopyrimidine, quinazoline, benzimidazole, or a combination of two or three of these groups, each of which may be substituted by one or more radicals R;

for a group of formula (RS-a), (RS-b), (RS-c), (RS-d) or (RS-e) as defined above.

Examples of very suitable radicals $R^N$ are the groups of formulae (Ar1-1) to (Ar1-24) as depicted above.

Preferably, the group R stands on each occurrence, identically or differently, for H, D, F, Cl, Br, I, CHO, CN, $N(Ar)_2$, $Si(R')_3$, a straight-chain alkyl, alkoxy or thioalkyl group having 1 to 40, preferably 1 to 20, more preferably 1 to 10 C atoms or a branched or cyclic alkyl, alkoxy or thioalkyl group having 3 to 40, preferably 3 to 20, more preferably 3 to 10 C atoms, each of which may be substituted by one or more radicals R', where in each case one or more non-adjacent $CH_2$ groups may be replaced by R'C═CR', O or S and where one or more H atoms may be replaced by D, F or CN, an aromatic or heteroaromatic ring system having 5 to 60 aromatic ring atoms, which may in each case be substituted by one or more radicals R', where two adjacent radicals R may form a mono- or polycyclic, aliphatic ring system or aromatic ring system, which may be substituted by one or more radicals R'. When R is selected from aromatic and heteroaromatic ring systems, it is preferably selected from aromatic and heteroaromatic ring systems having 5 to 40, preferably 5 to 30, more preferably 5 to 18 aromatic ring atoms or from aromatic or heteroaromatic ring system having 5 to 60 aromatic ring atoms corresponding to groups of formula (RS-e) as defined above.

Preferably, the group Ar is on each occurrence, identically or differently, an aromatic or heteroaromatic ring system having 5 to 18, preferably 6 to 18 aromatic ring atoms, which may in each case also be substituted by one or more radicals R'.

Preferably, R' stands on each occurrence, identically or differently, for H, D, F, Cl, Br, I, CN, a straight-chain alkyl, alkoxy or thioalkyl group having 1 to 10 C atoms or a branched or cyclic alkyl, alkoxy or thioalkyl group having 3 to 10 C atoms, where one or more H atoms may be replaced by D or F, or an aromatic or heteroaromatic ring system having 5 to 18, preferably 6 to 18 C atoms.

Examples of suitable compounds of formula (1) are the structures shown in the table below:

-continued
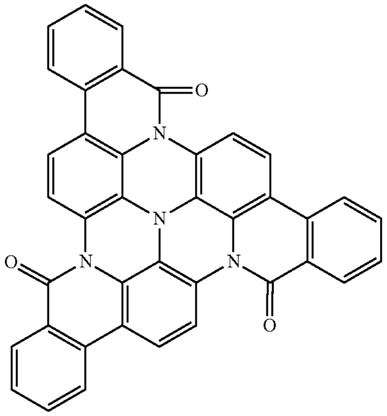
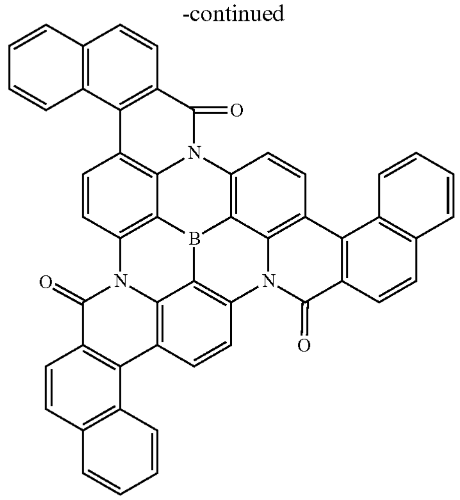
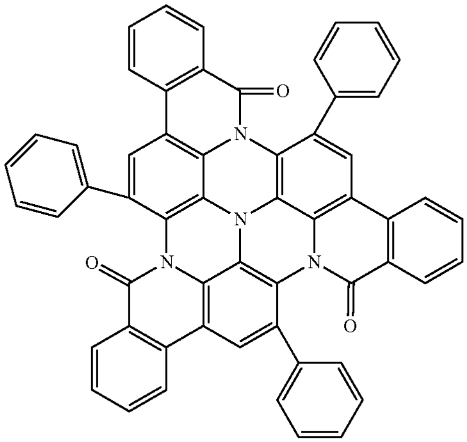
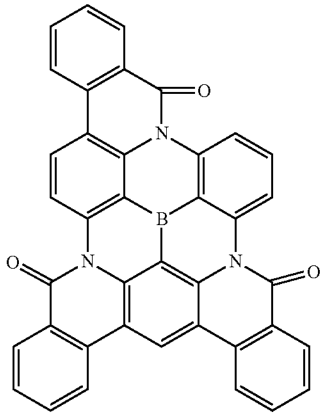
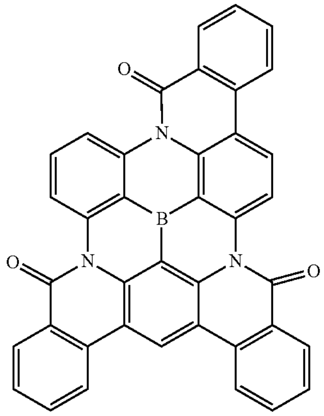
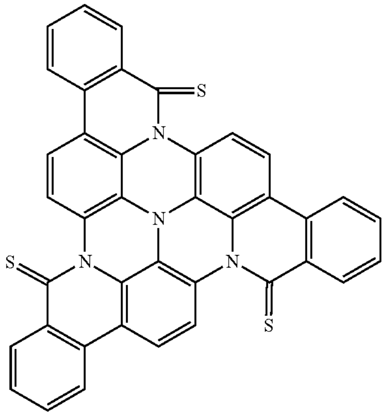
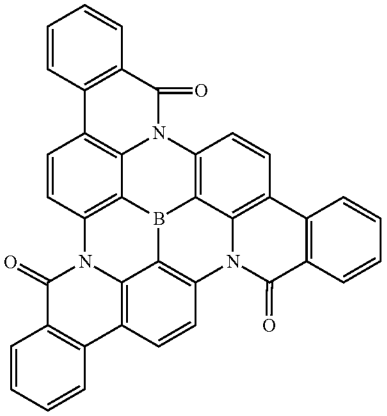

-continued
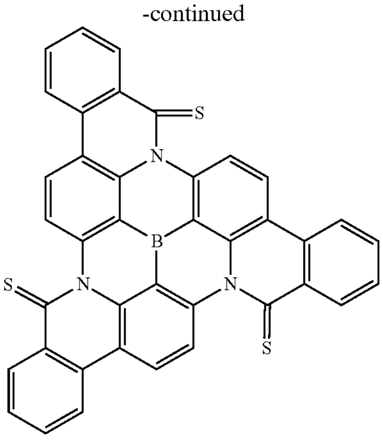
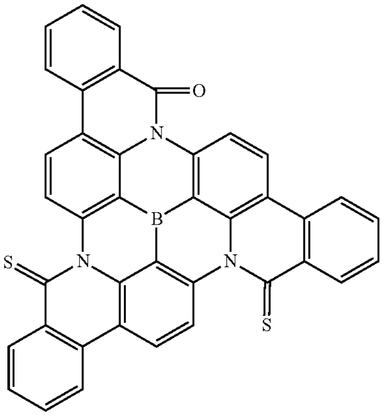
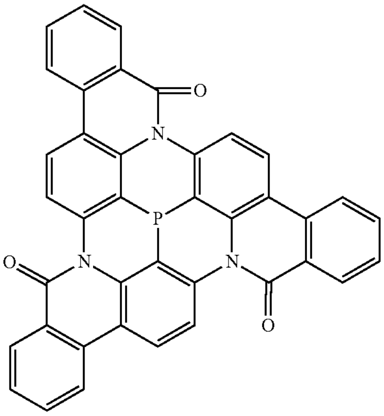
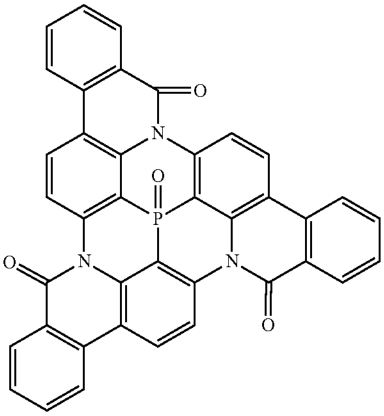
-continued
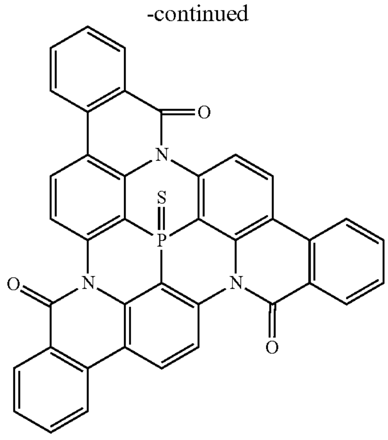
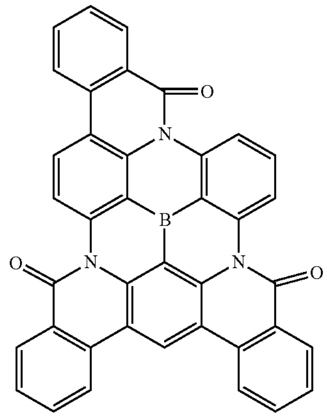
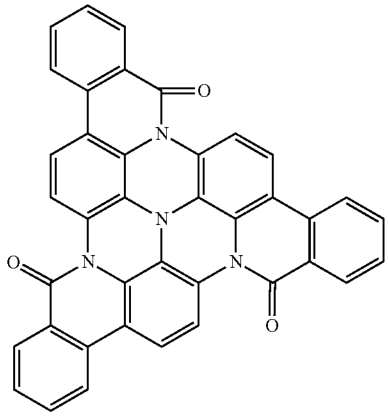
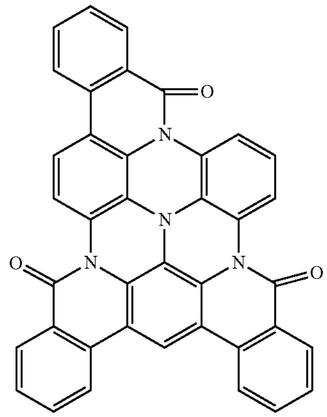

-continued
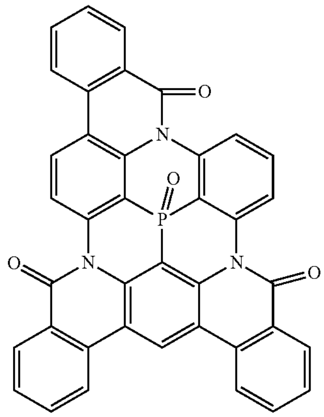
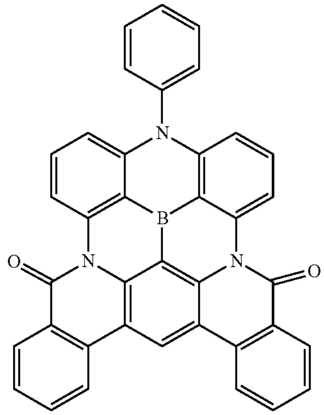
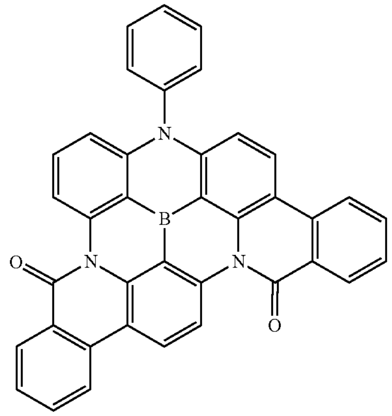
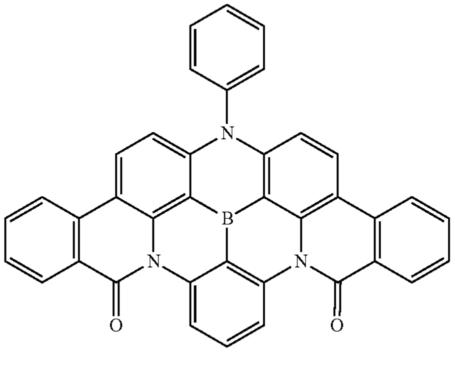
-continued
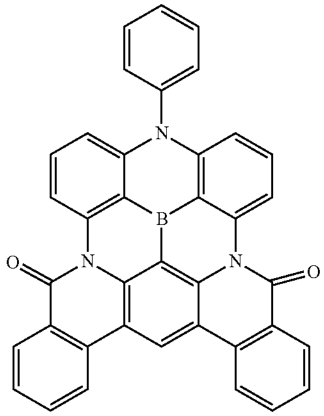
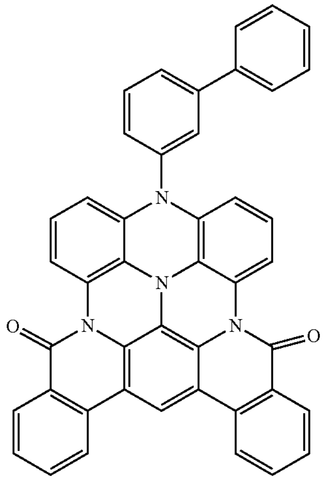
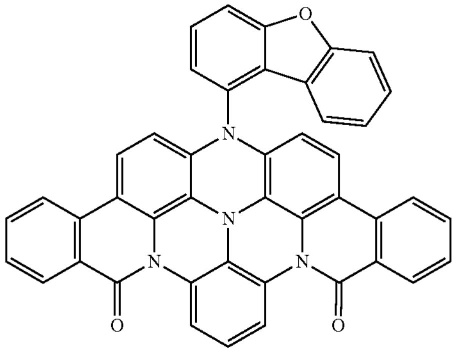
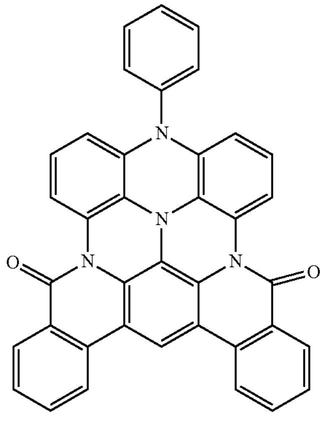

-continued
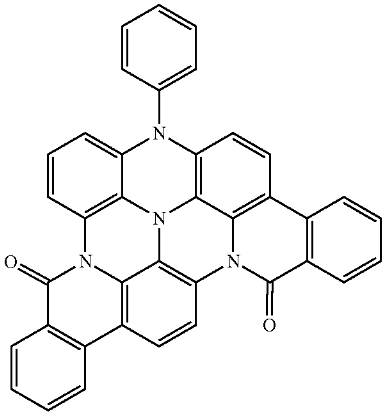
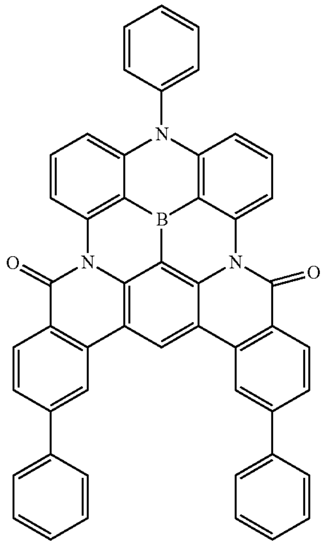
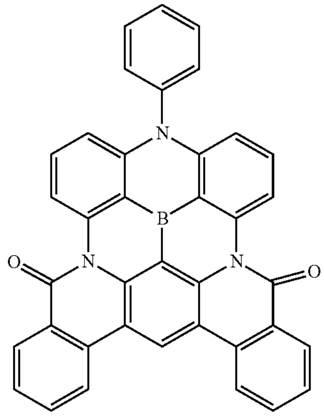
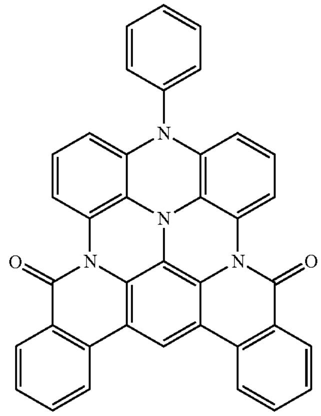
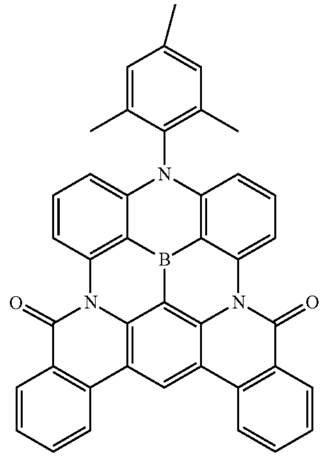
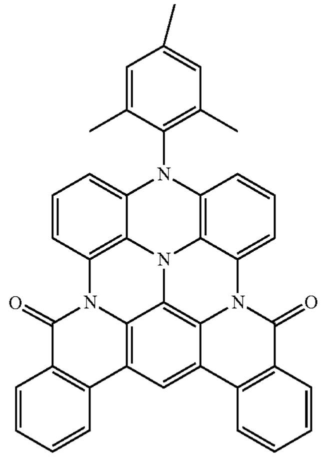
-continued -continued
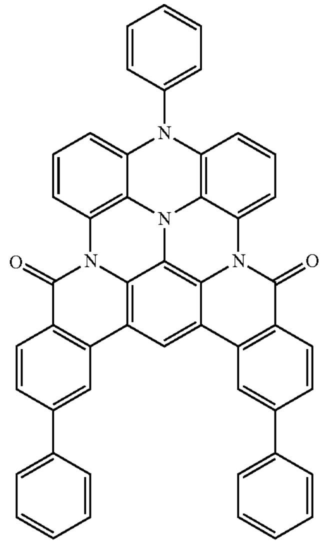
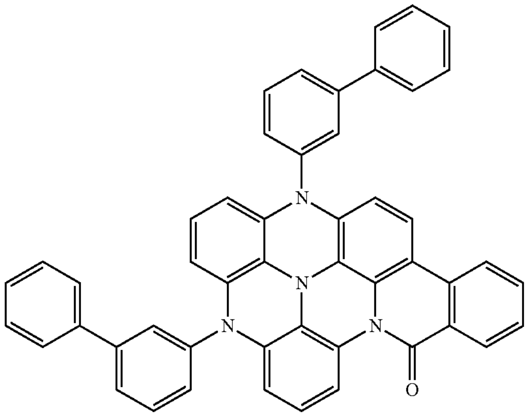
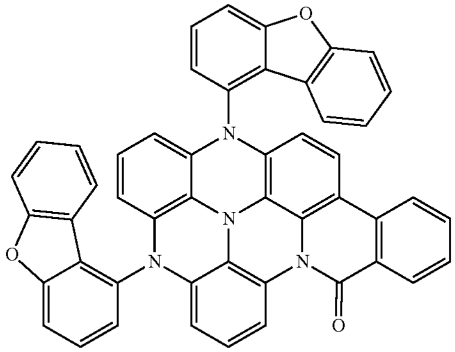
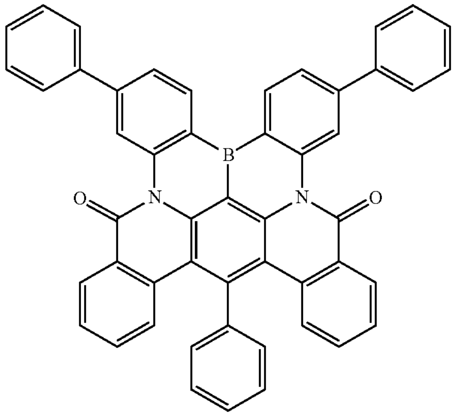
-continued
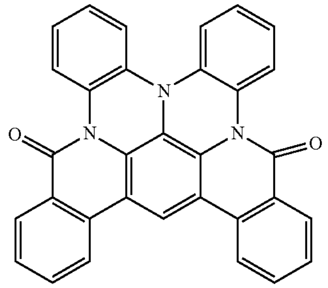
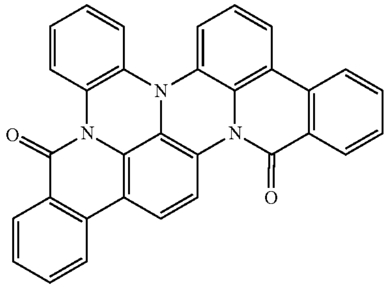
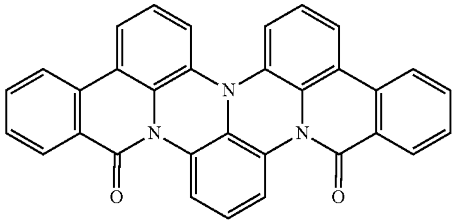
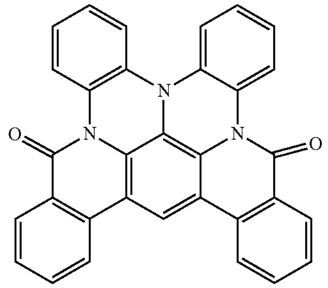
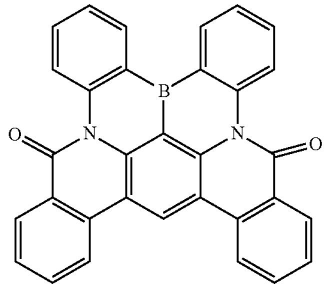
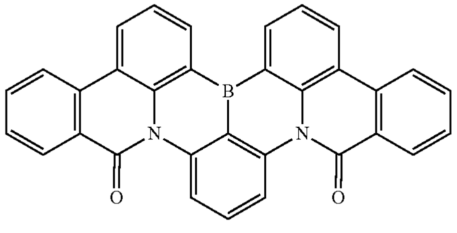

-continued
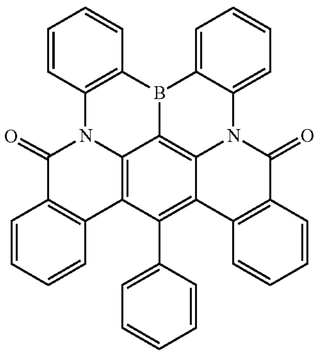
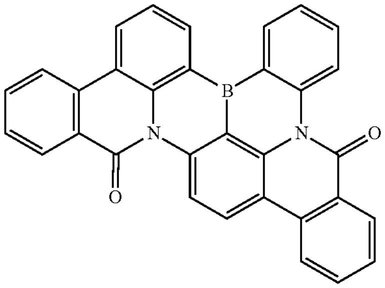
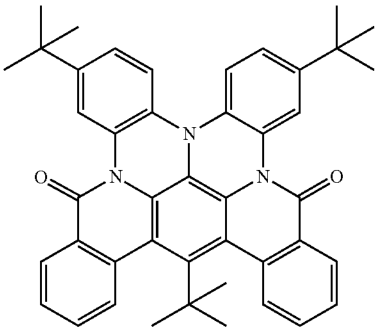
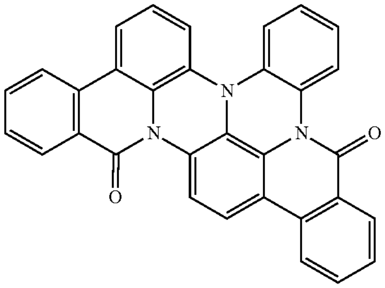
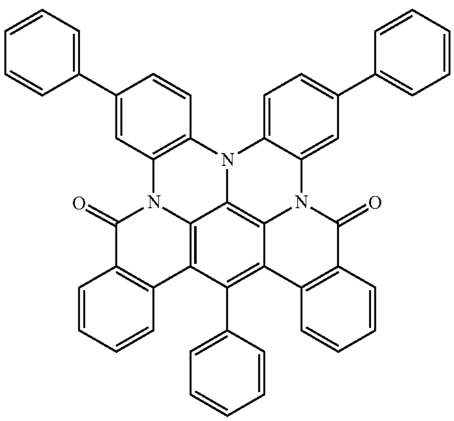
-continued
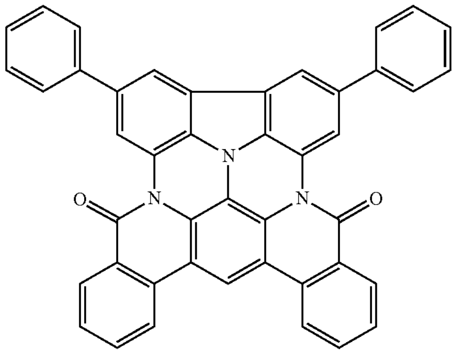
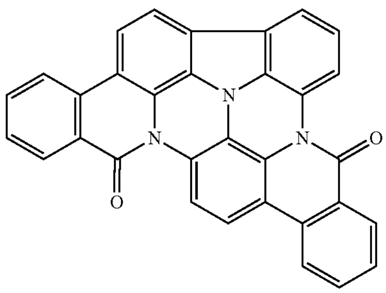
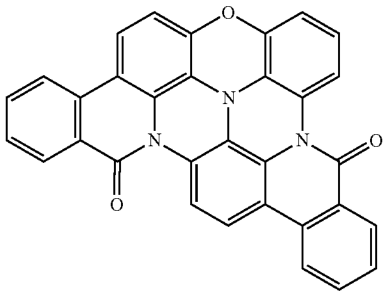
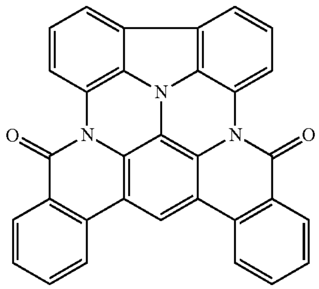
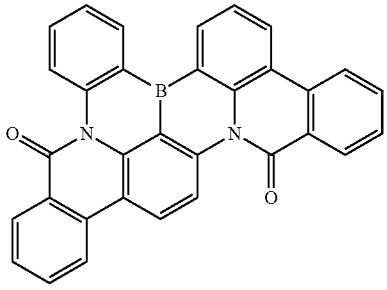

-continued
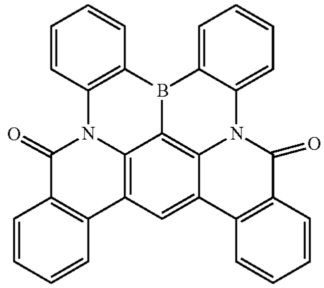
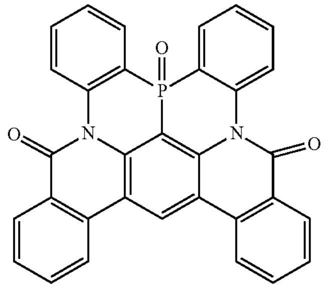
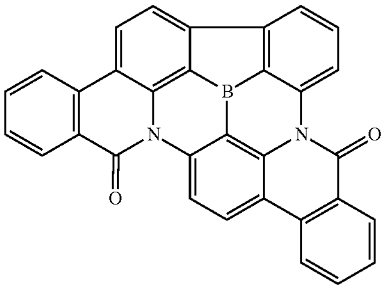
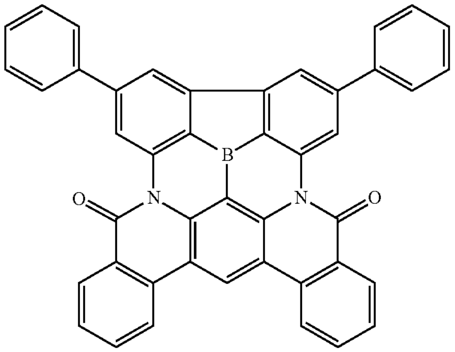
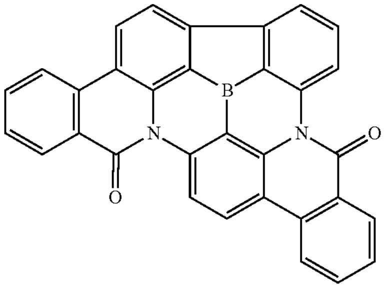
-continued
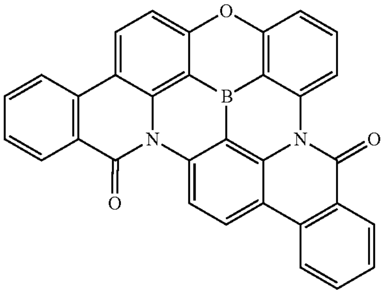
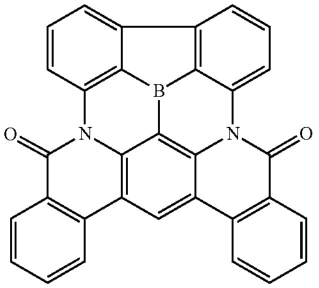
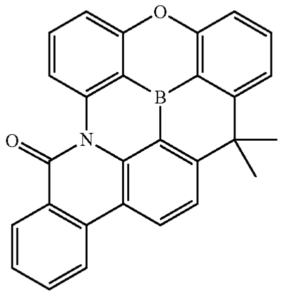
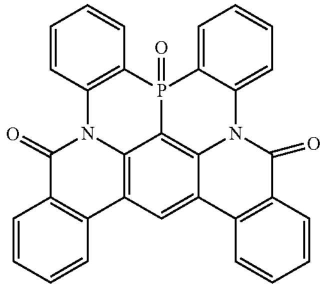
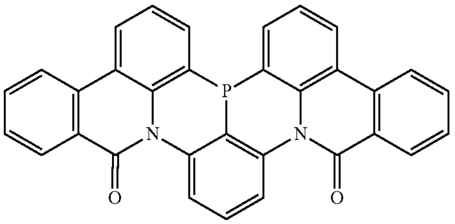
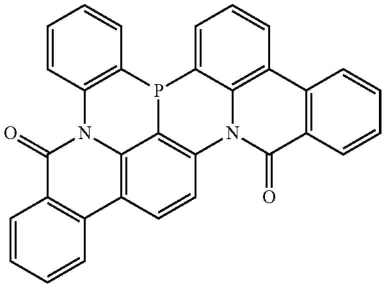

-continued
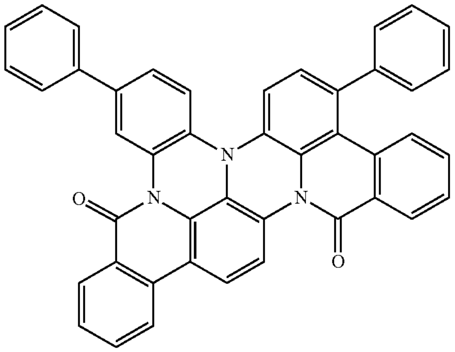
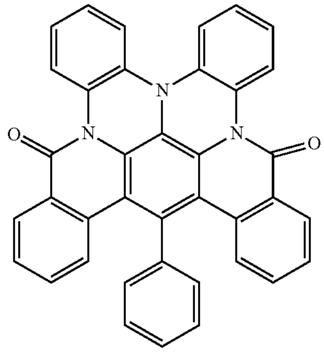
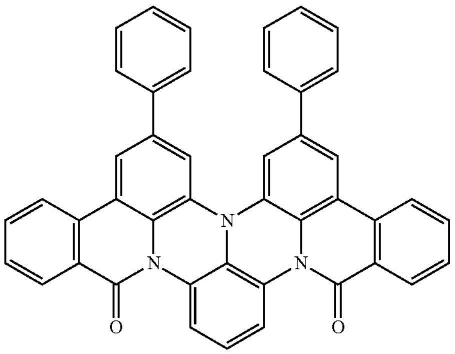
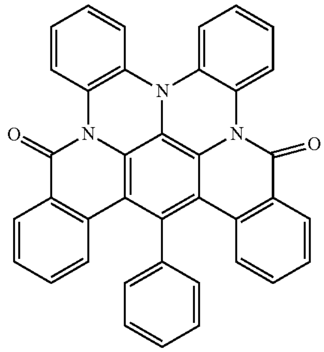
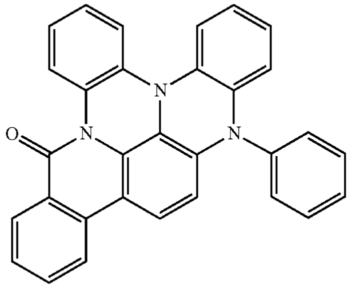
-continued
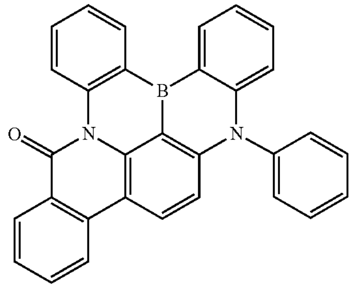
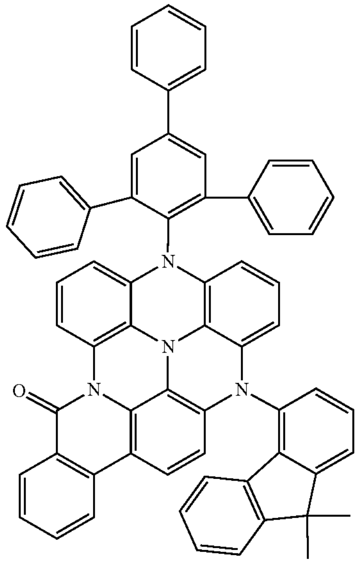
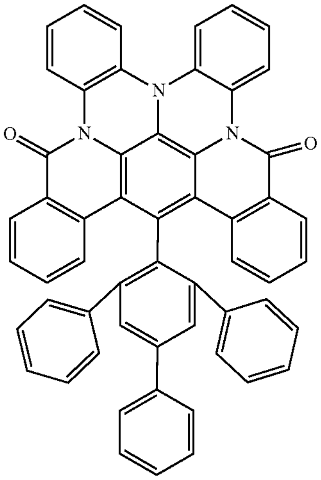

-continued
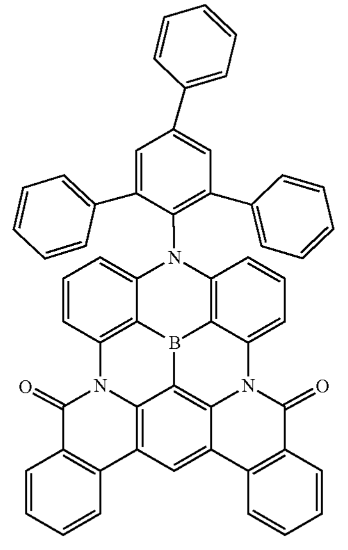
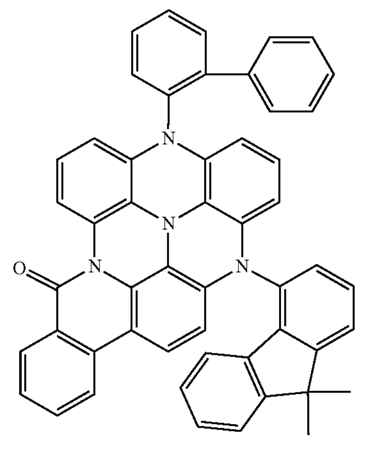
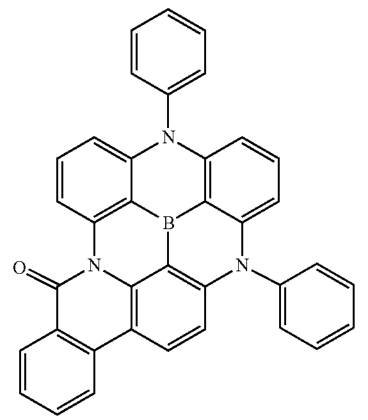
-continued
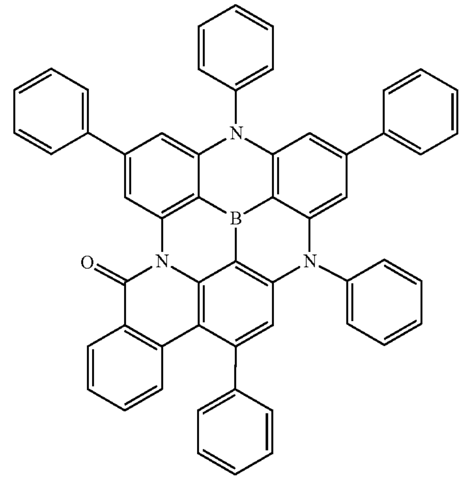
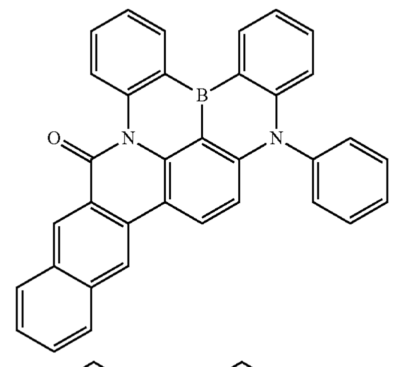
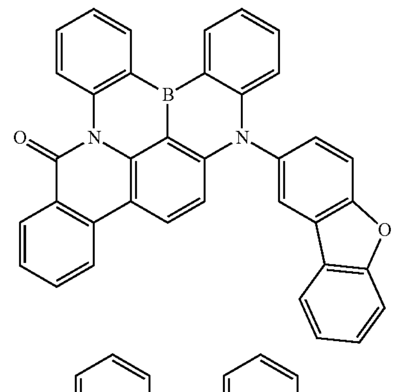
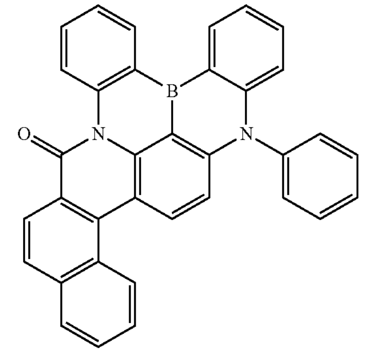

-continued
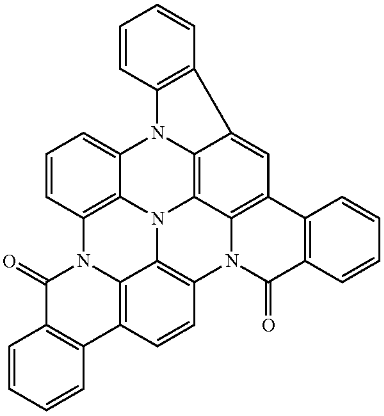
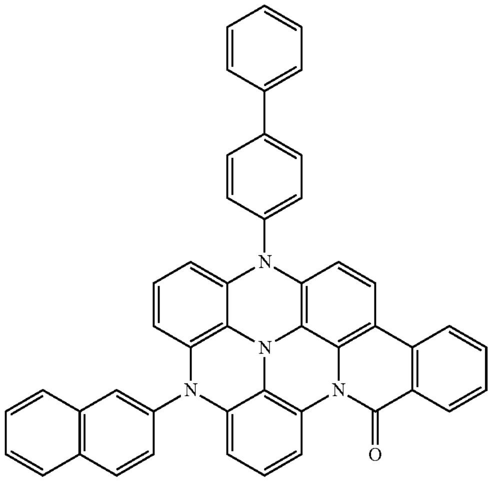
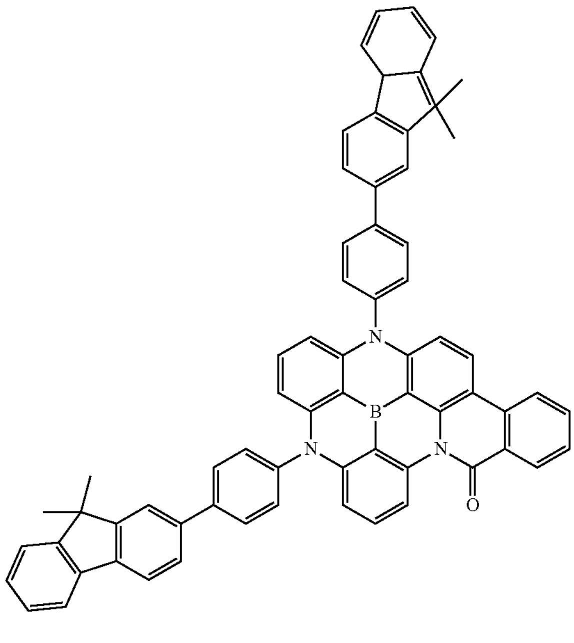
-continued
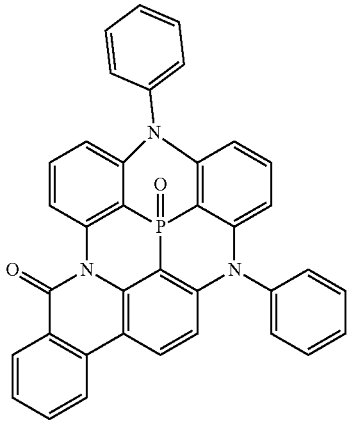
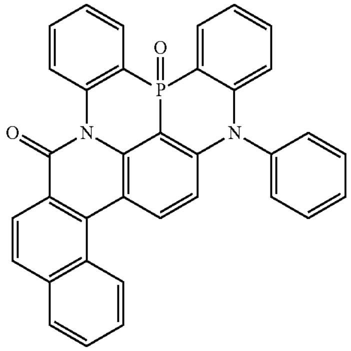
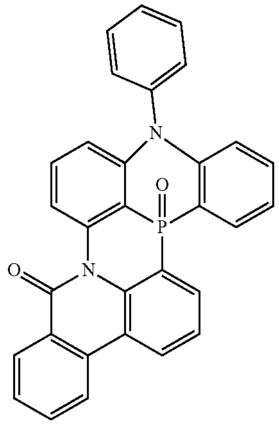
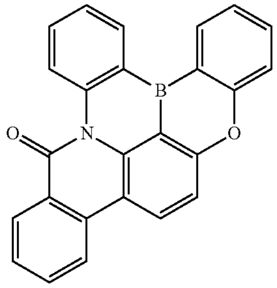
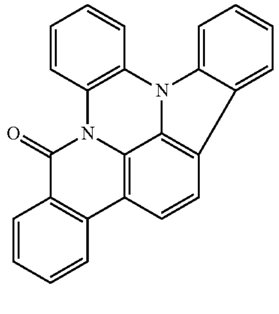
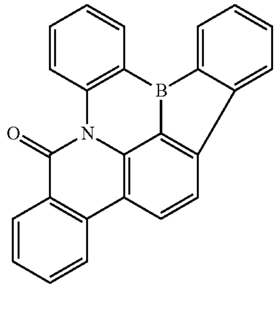

-continued
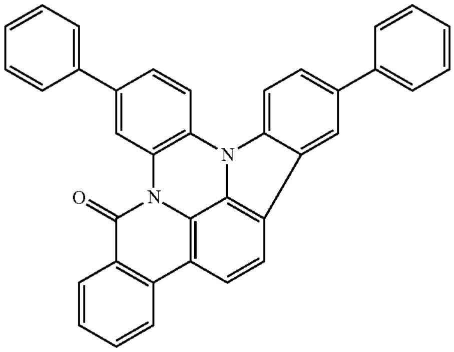
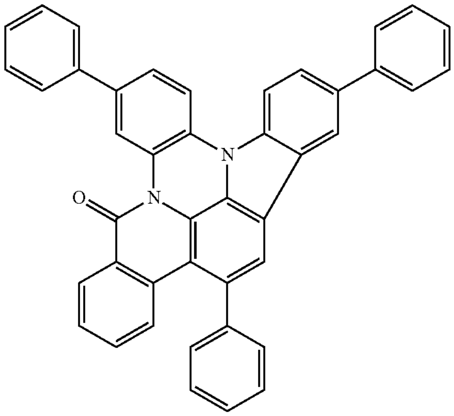
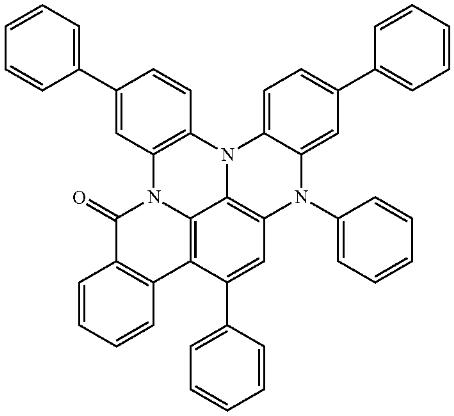
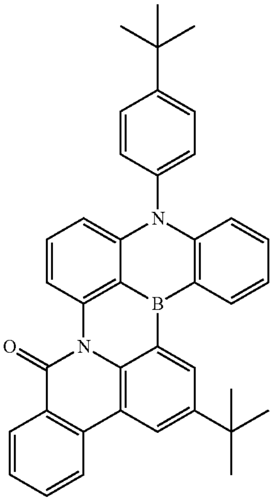
-continued
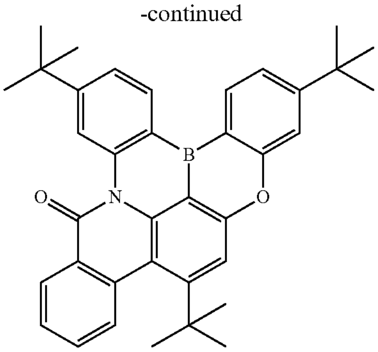
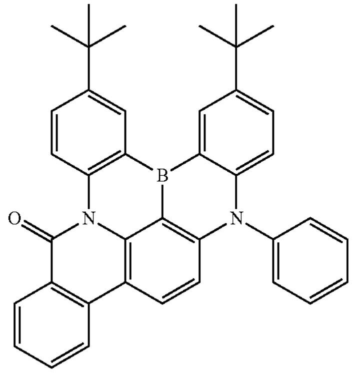
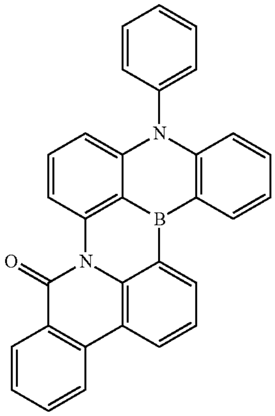
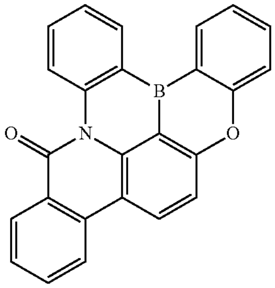
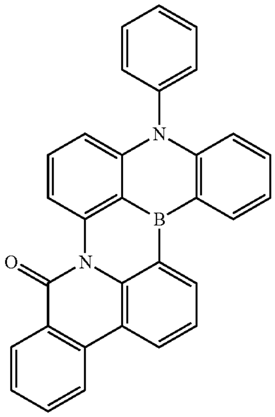
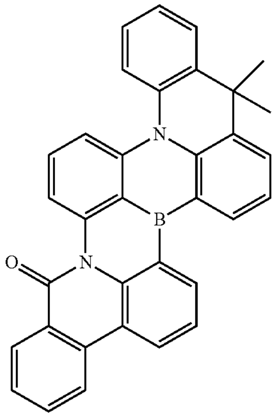

-continued
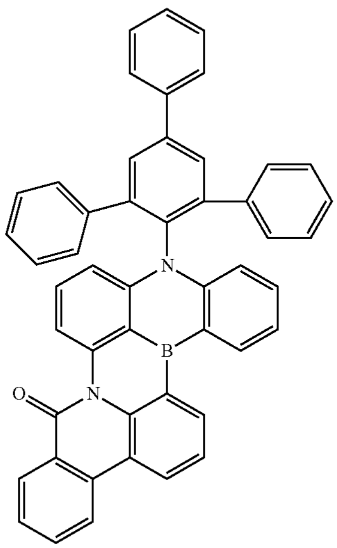
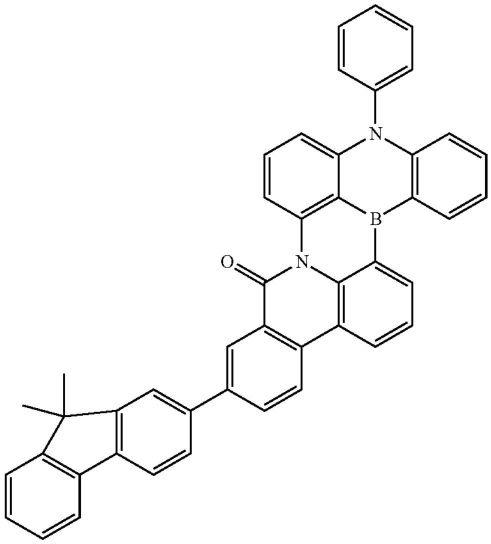
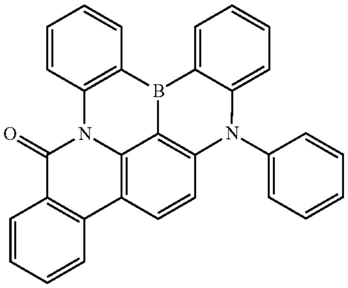
-continued
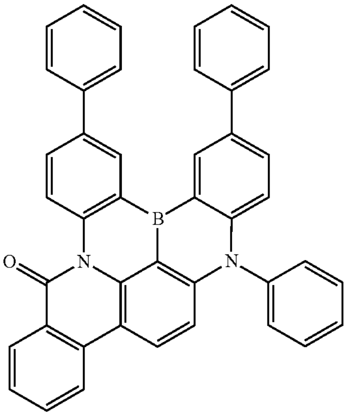
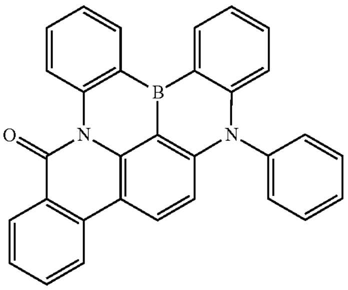
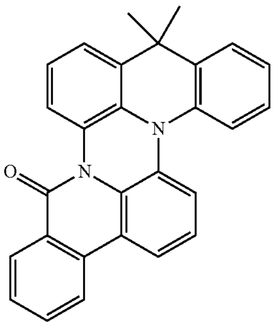
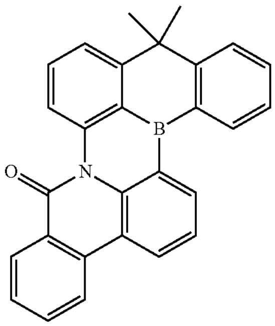
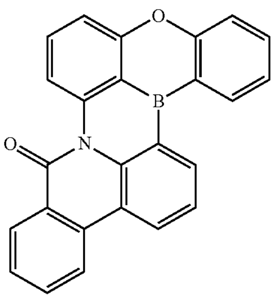
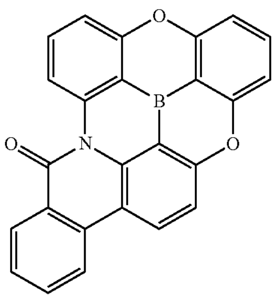
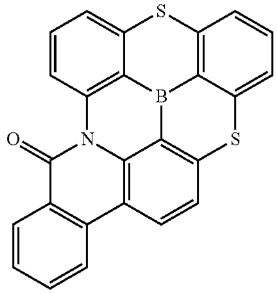

-continued
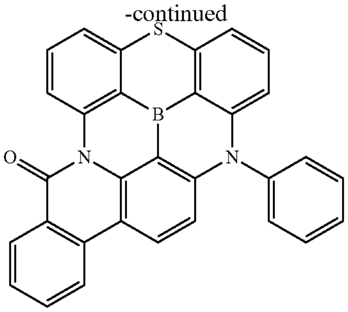
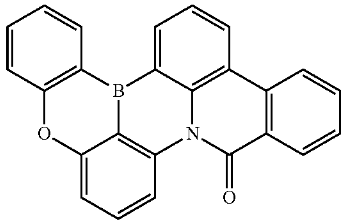
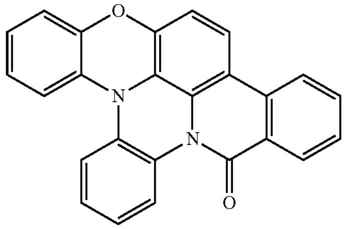
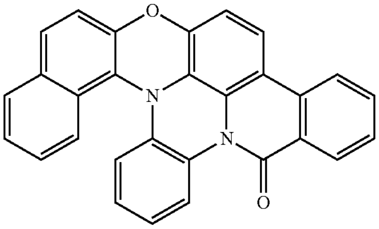
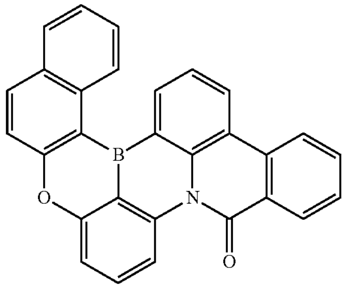
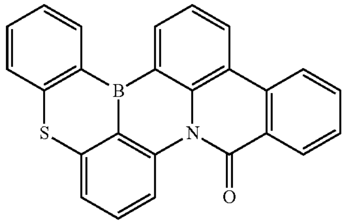
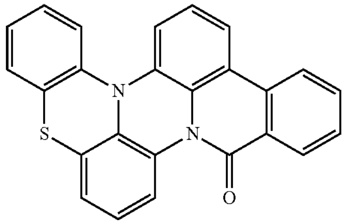
-continued
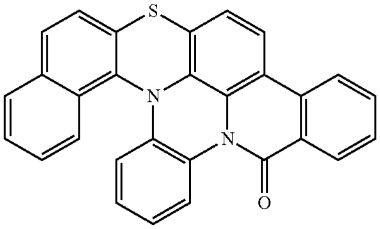
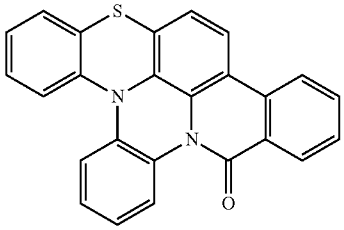
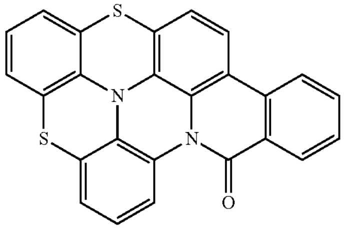
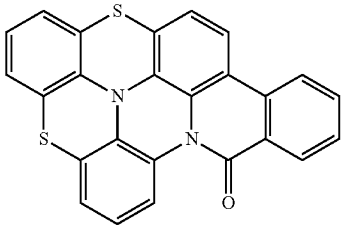
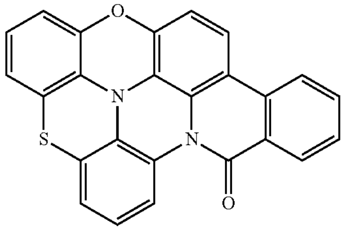
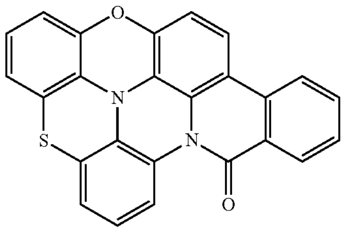
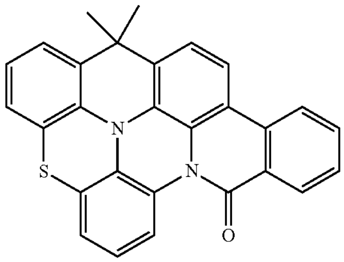

-continued
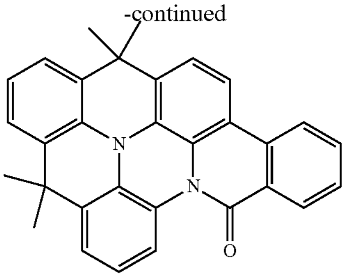
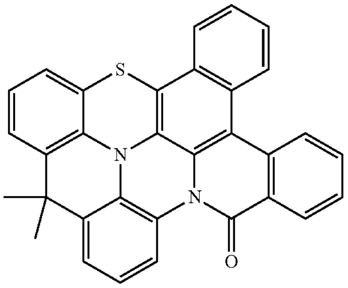
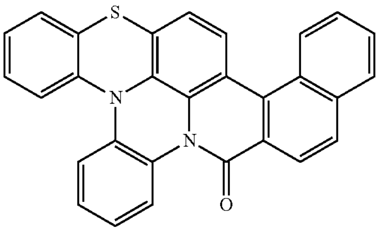
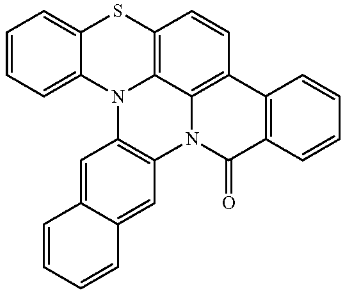
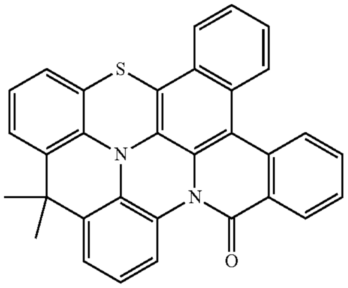
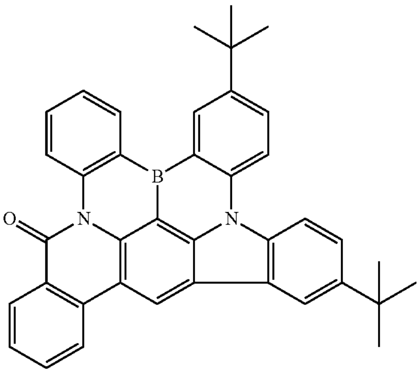
-continued
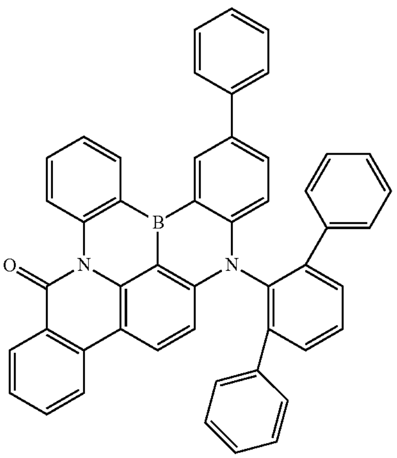
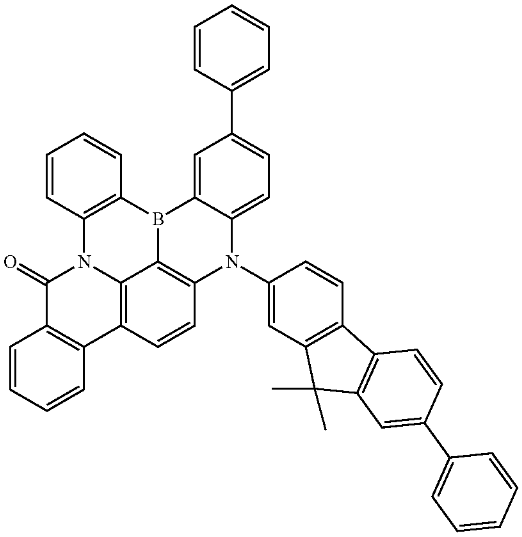
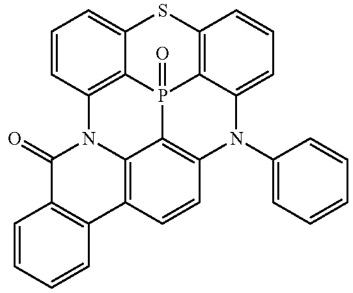
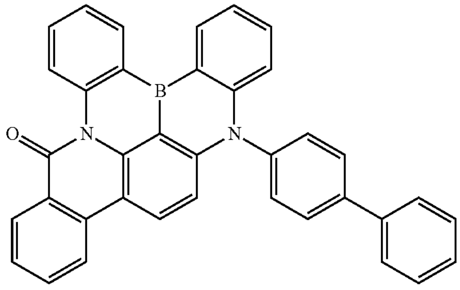

-continued
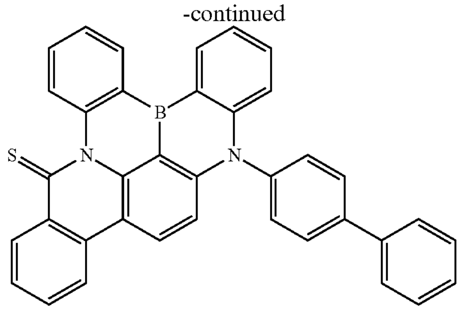
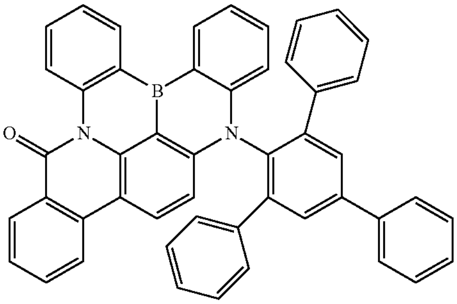
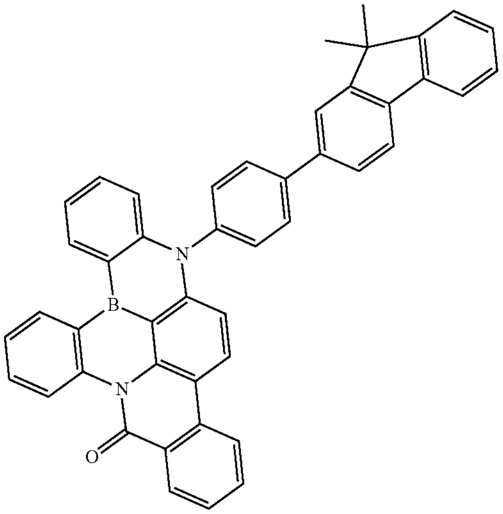
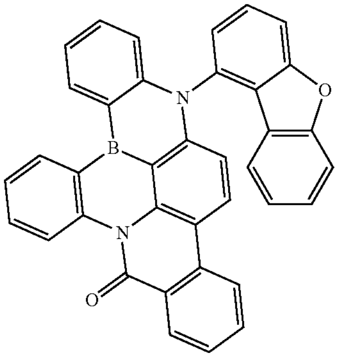
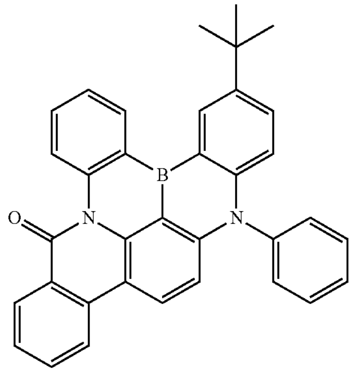
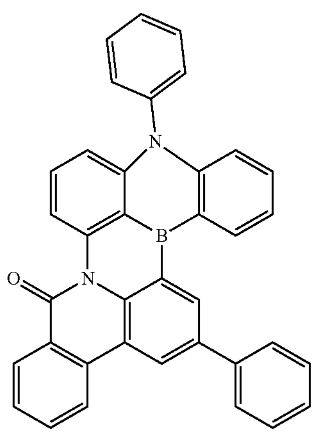
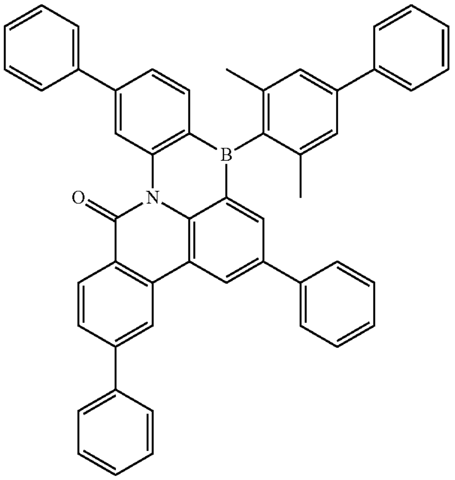
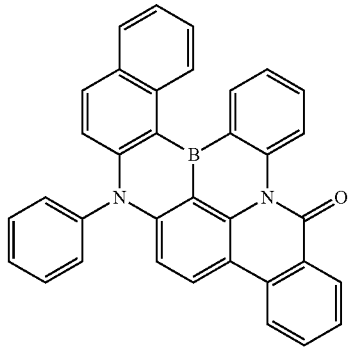
-continued -continued
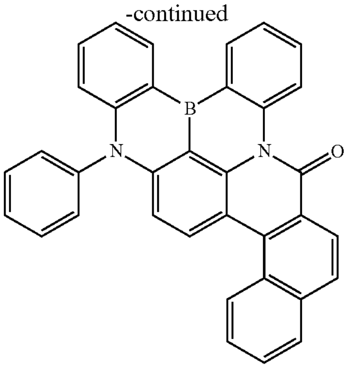
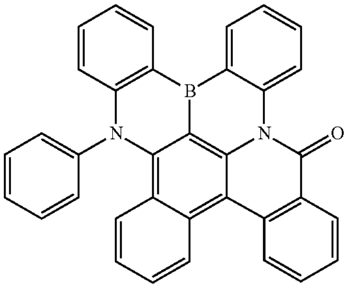
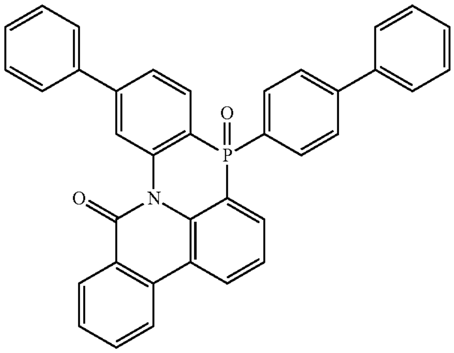
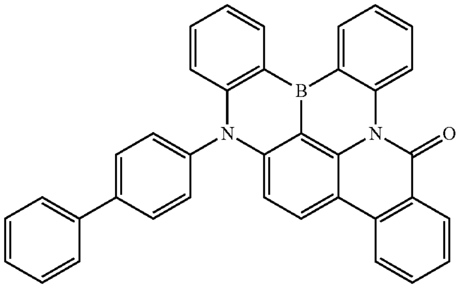
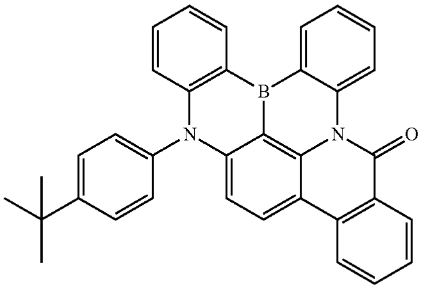
-continued
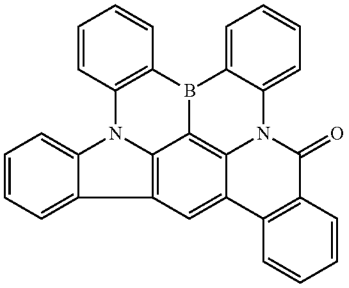
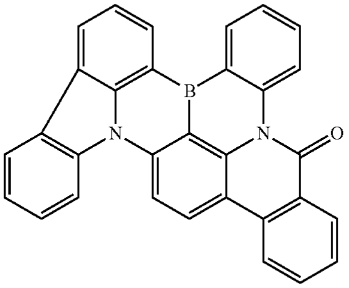
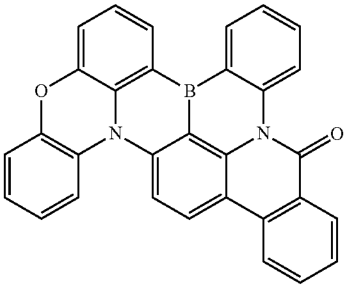
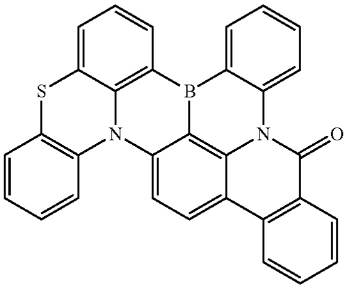
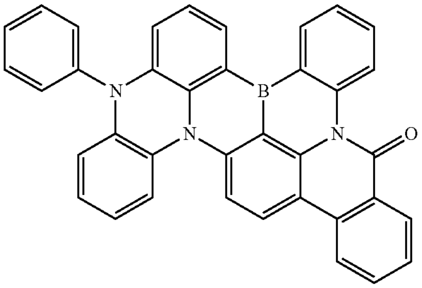
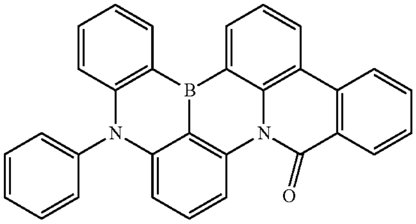

-continued
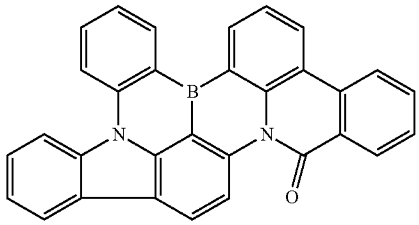
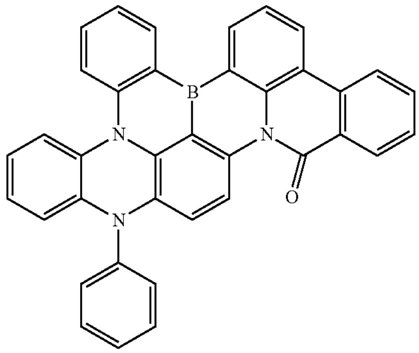
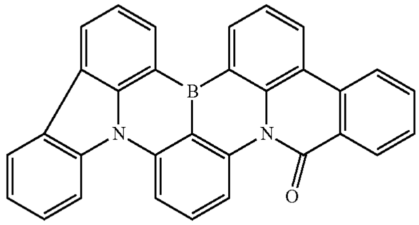
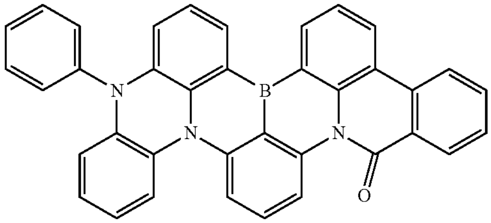
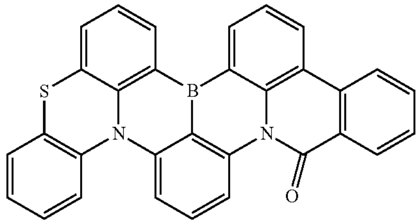
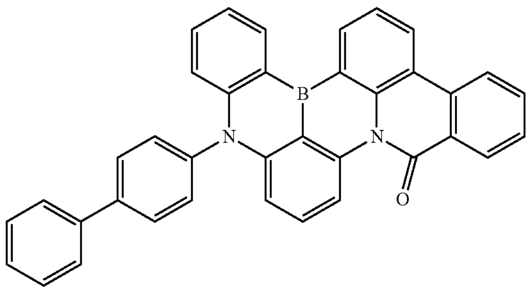
-continued
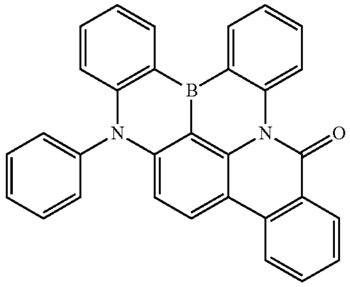
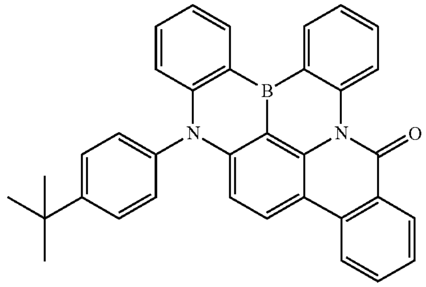
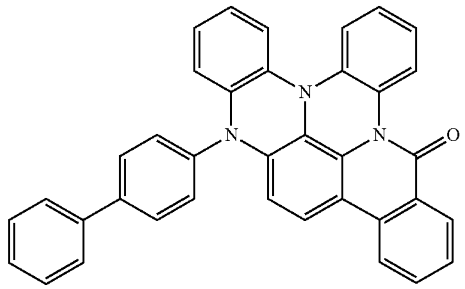
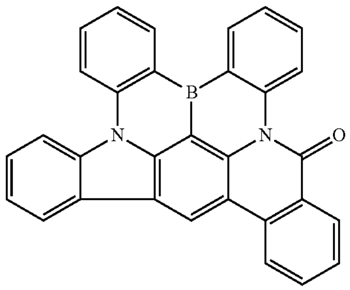
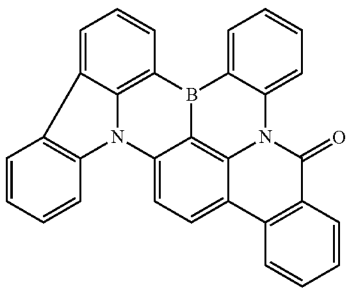

-continued
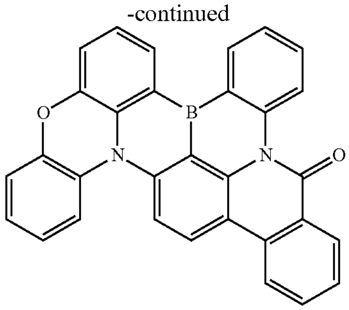
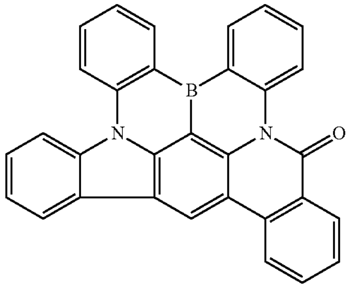
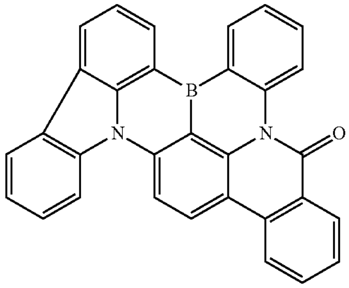
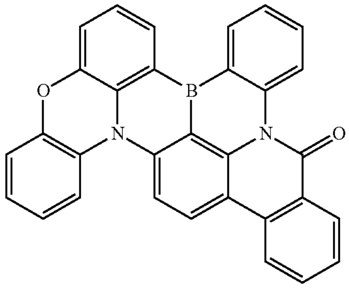
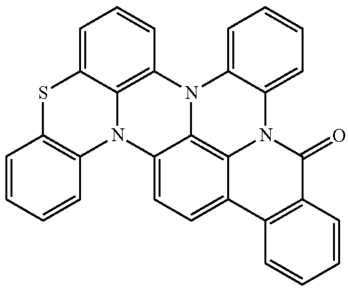
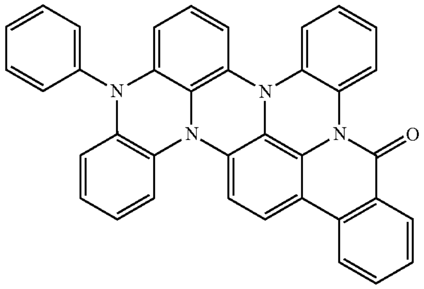
-continued
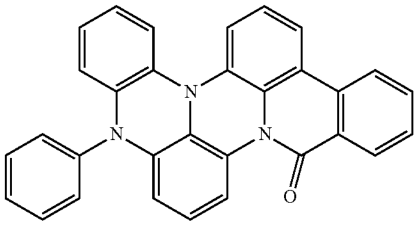
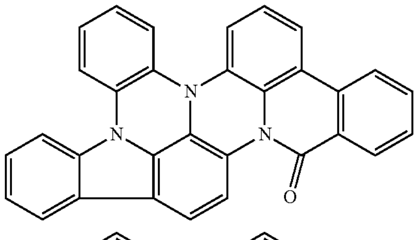
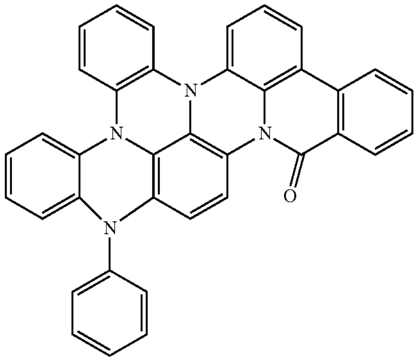
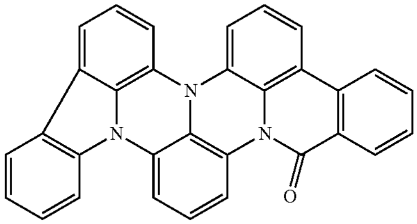
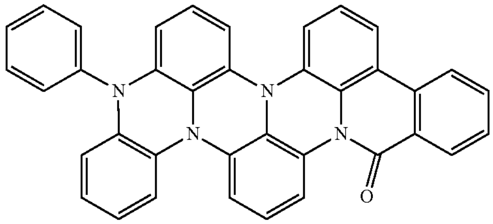
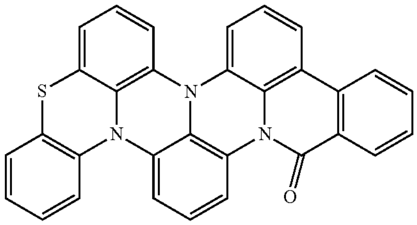

-continued
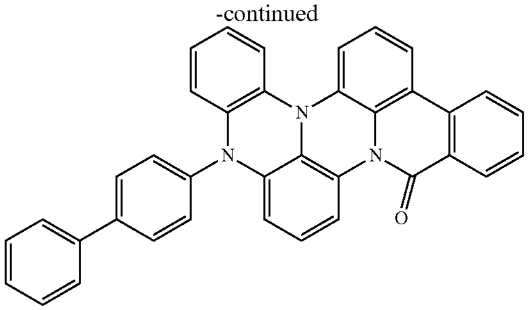
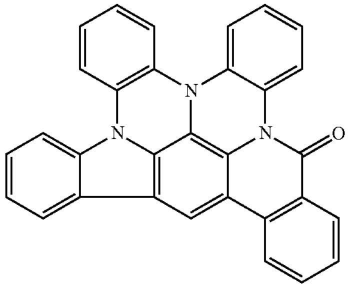
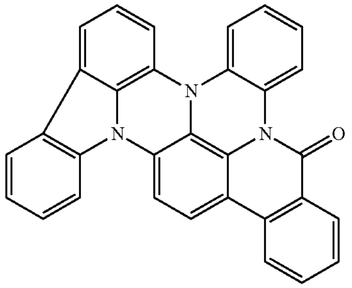
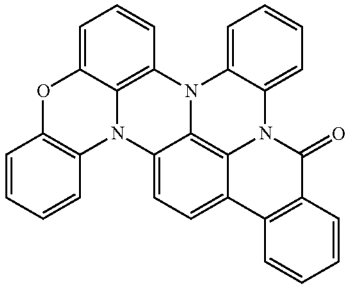
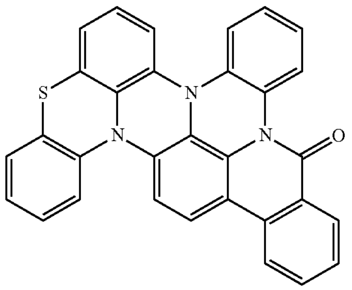
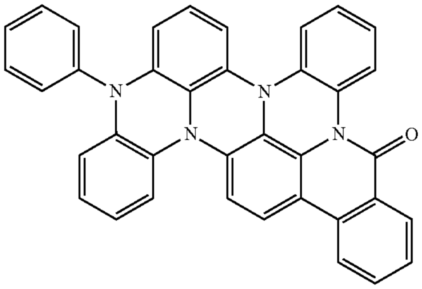
-continued
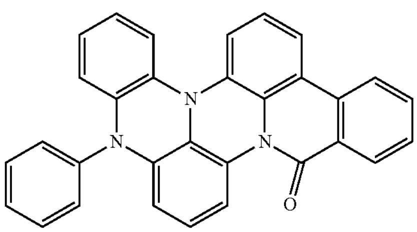
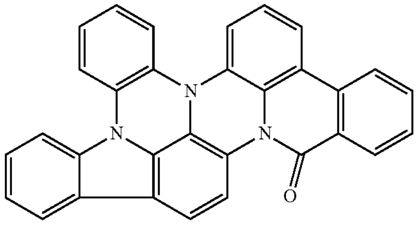
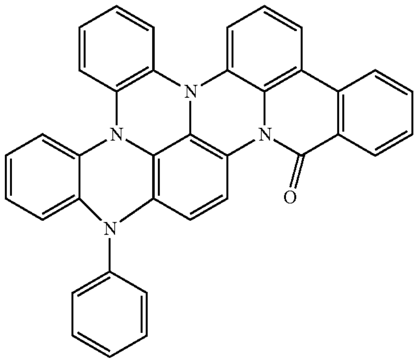
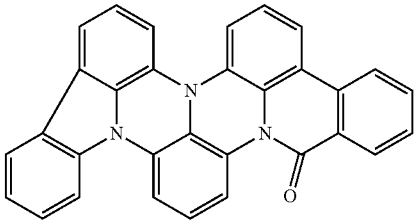
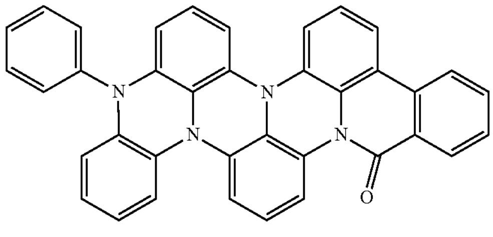
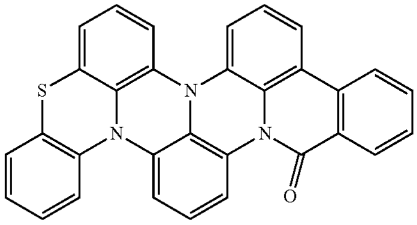

-continued
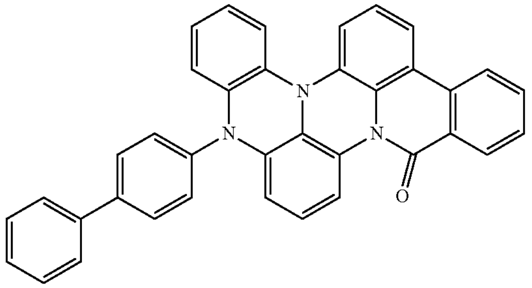
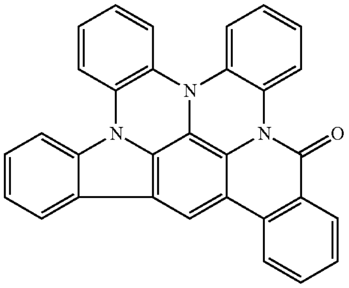
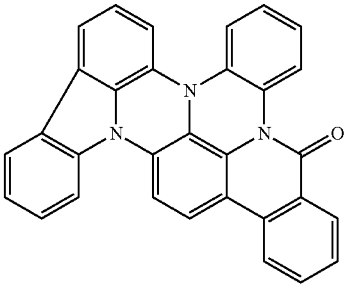
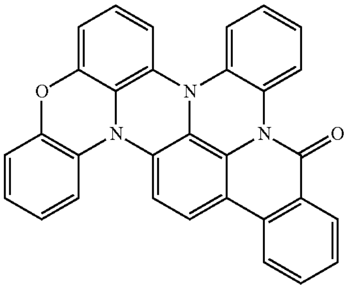
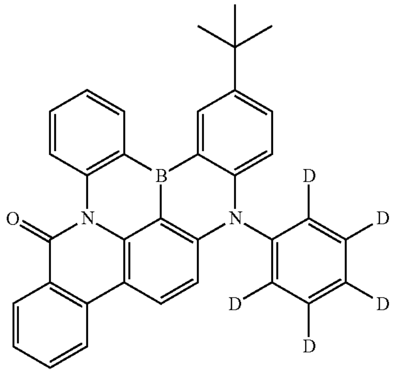
-continued
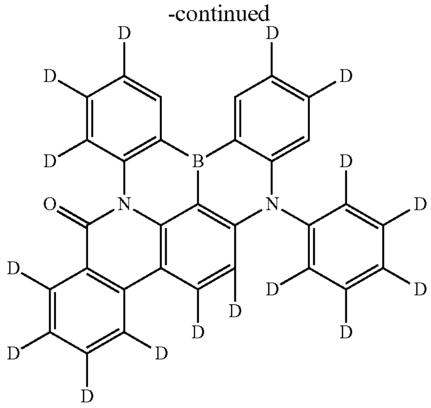
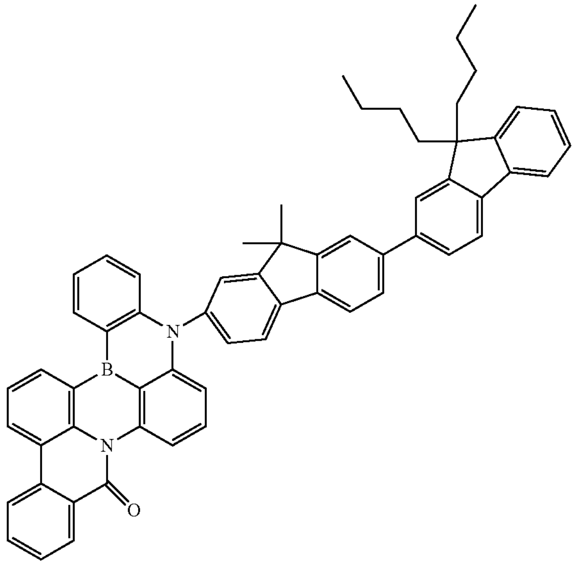
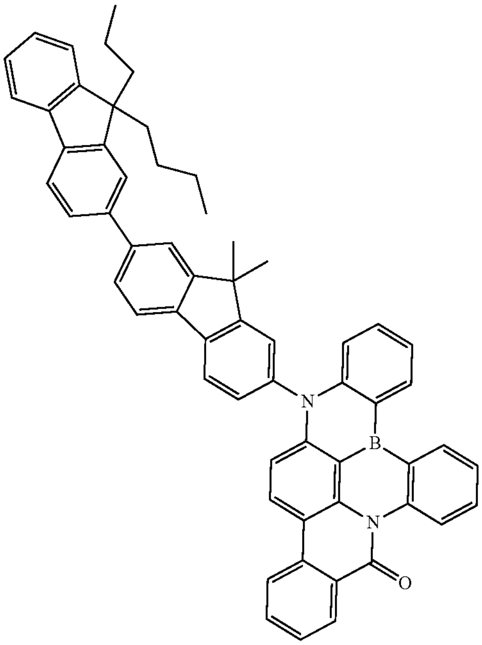

-continued
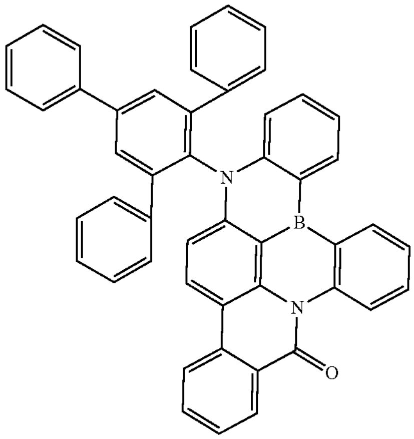
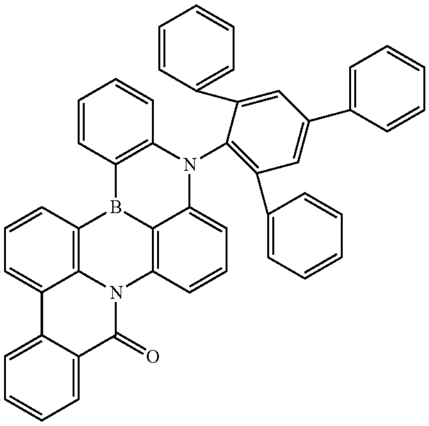
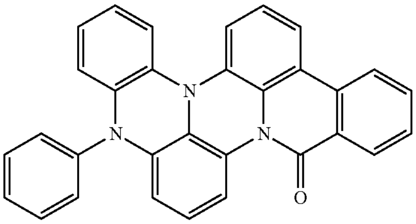
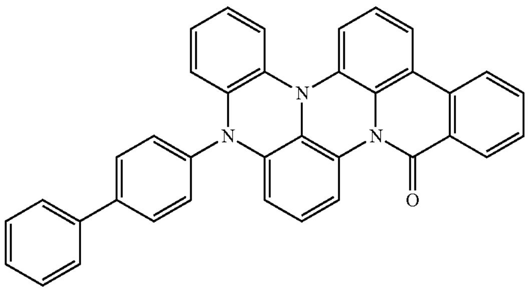
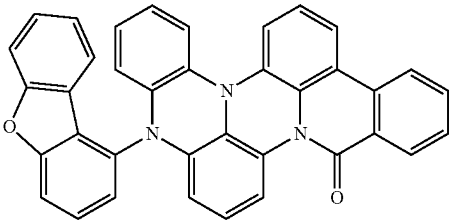
-continued
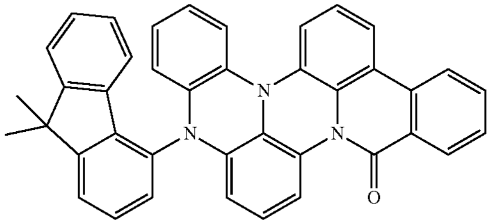
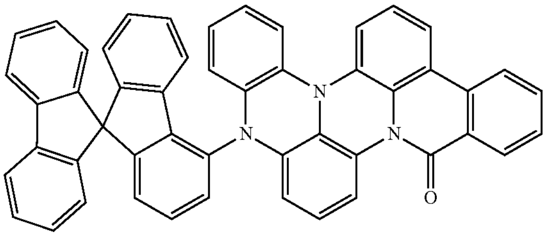
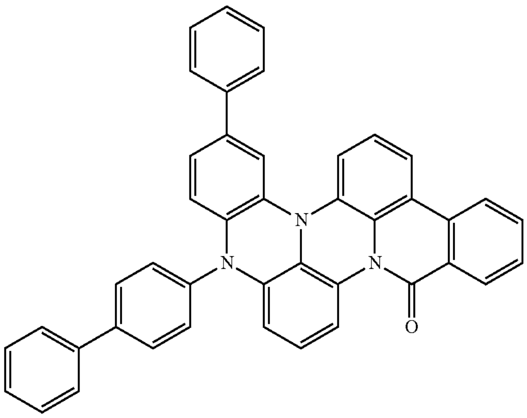
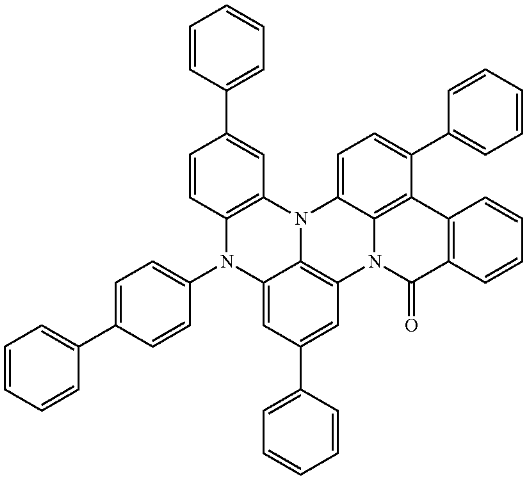
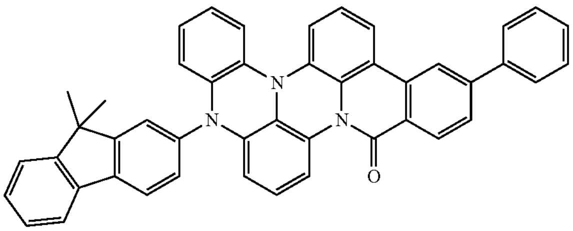

-continued

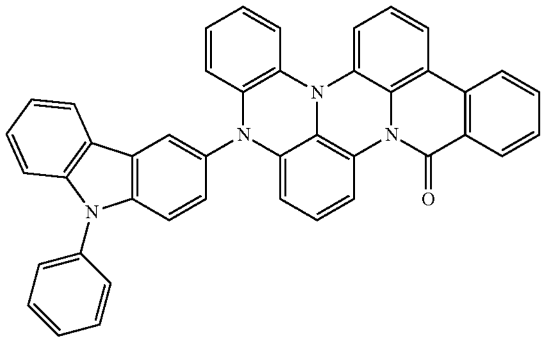

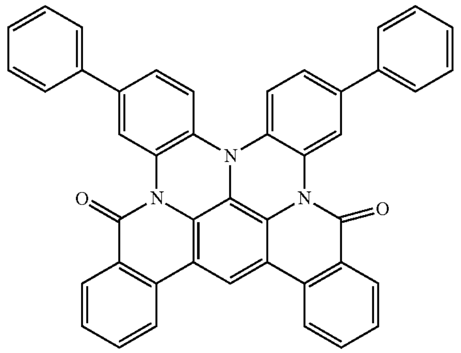

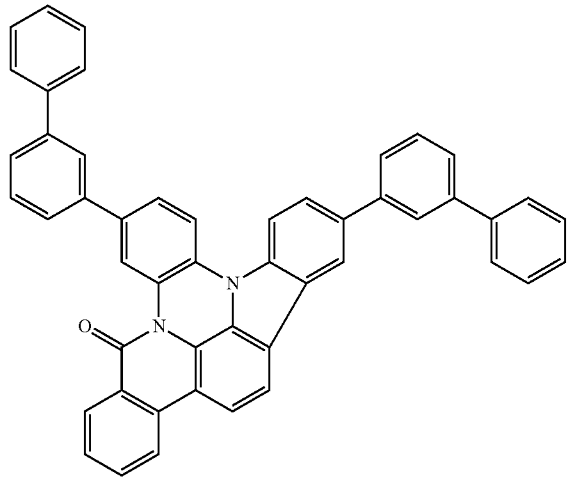

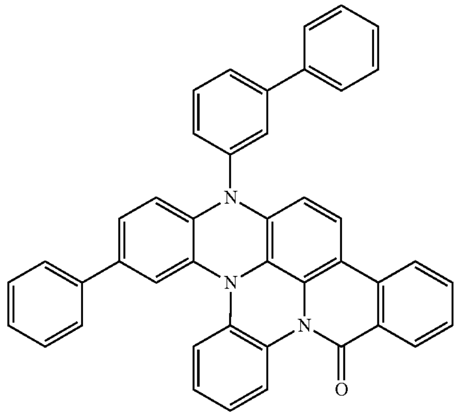

The compounds according to the invention can be prepared by synthesis steps known to the person skilled in the art, such as, for example, bromination, Suzuki coupling, Ullmann coupling, Hartwig-Buchwald coupling, etc. An example of a suitable synthesis process is depicted in general terms in schemes 1 and 6 below.

Scheme 1

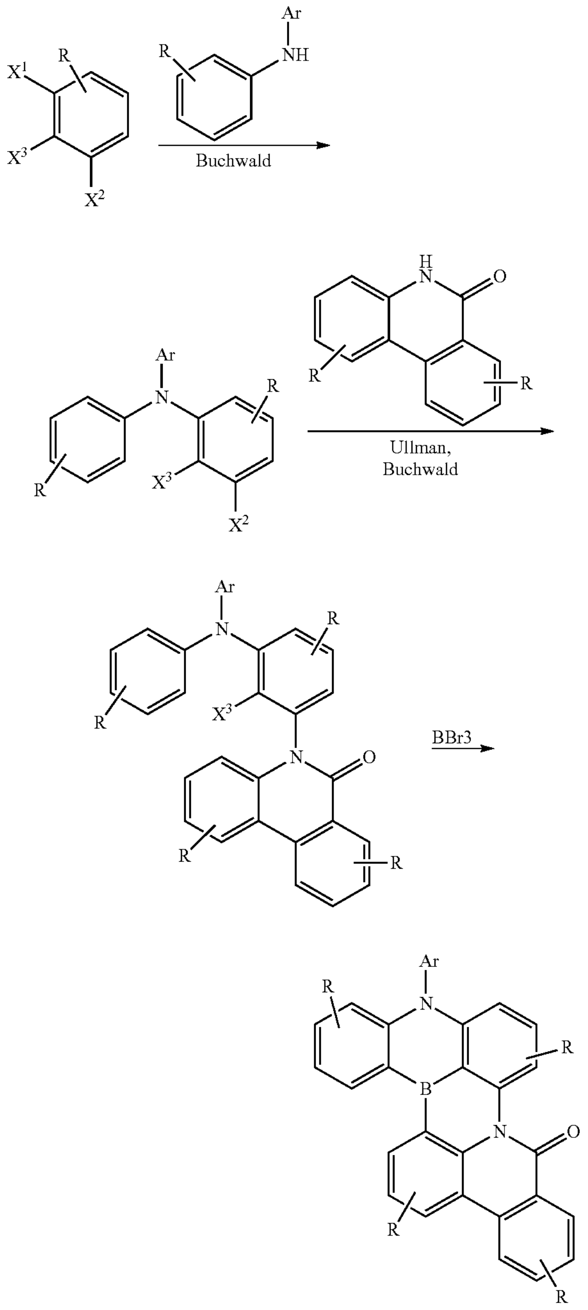

where $X^1$, $X^2$ and $X^3$ are leaving groups, more preferably selected from halogen atoms like, Cl, Br, F and I. More preferably, $X^1$ is I, $X^2$ is Br and $X^3$ is Cl;

Ar is an aromatic or heteroaromatic group; more preferably Ar has the same definition as the group Ar defined above;

R is a substituent, more preferably R has the same definition as the group R defined above;

Scheme 2
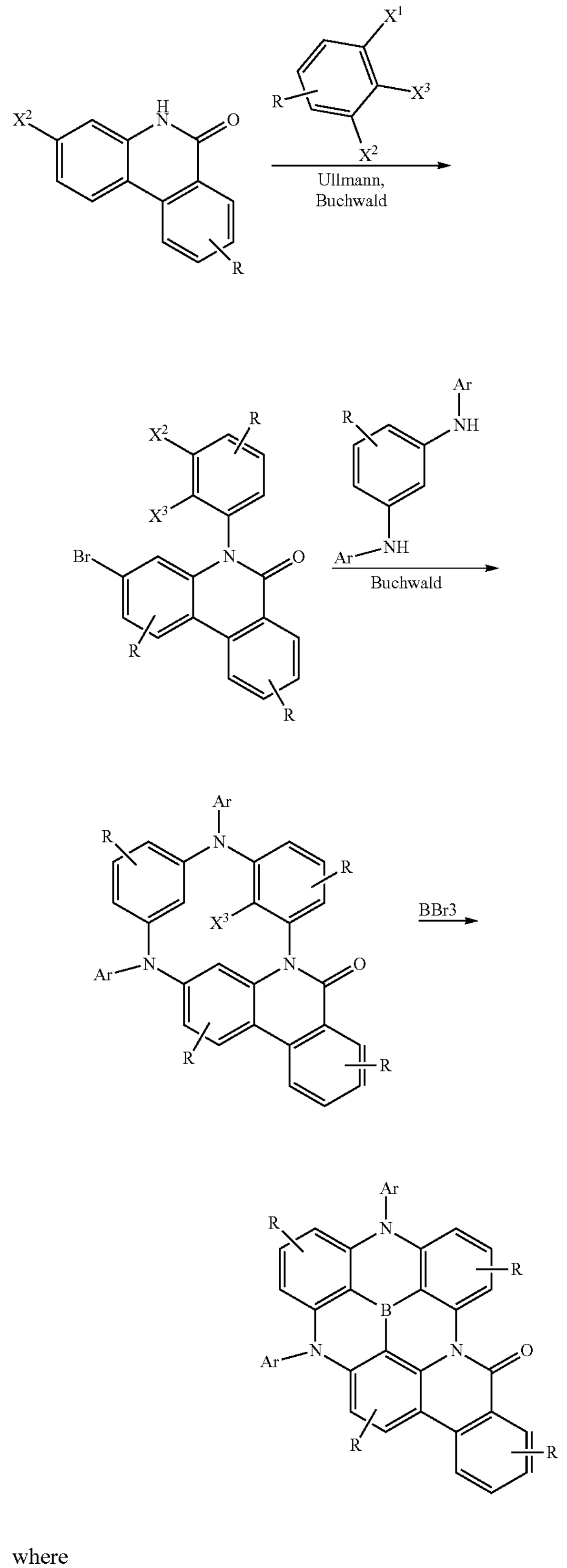
where
X¹, X², X³, Ar and R have the same definition as given in Scheme 1.
Scheme 3
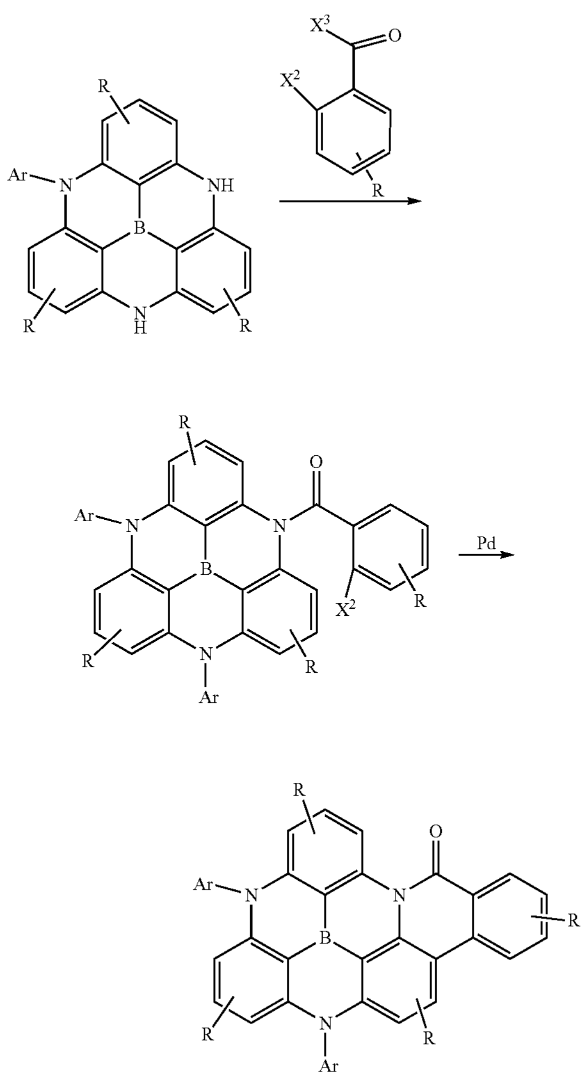
where
X², X³, Ar and R have the same definition as given in Scheme 1.
Scheme 4
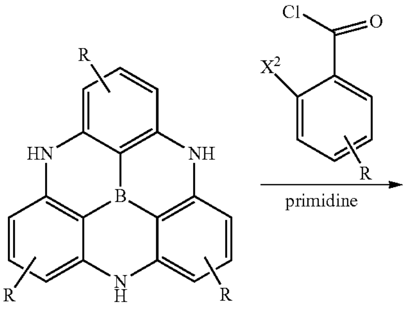

-continued
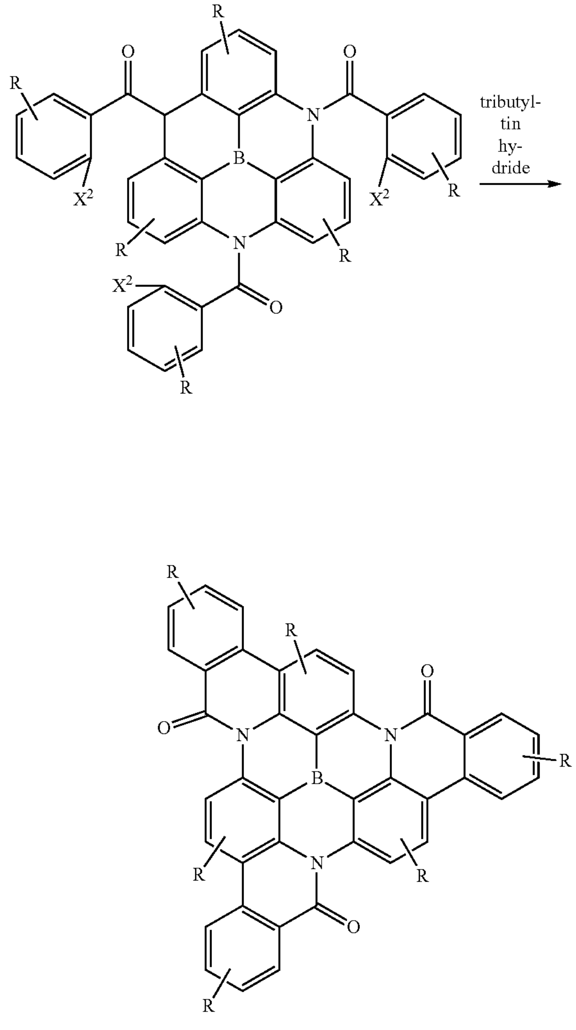
where
$X^2$ and R have the same definition as given in Scheme 1.
Scheme 5
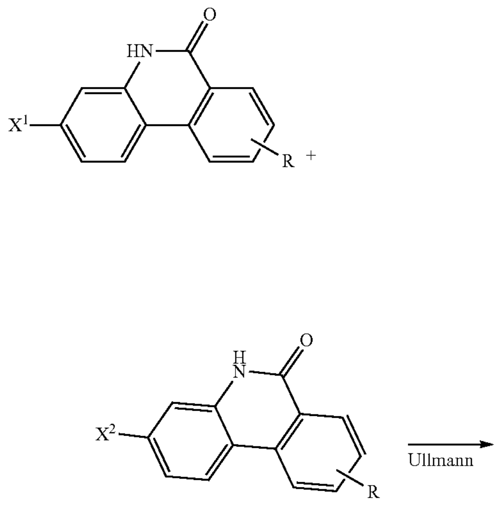
-continued
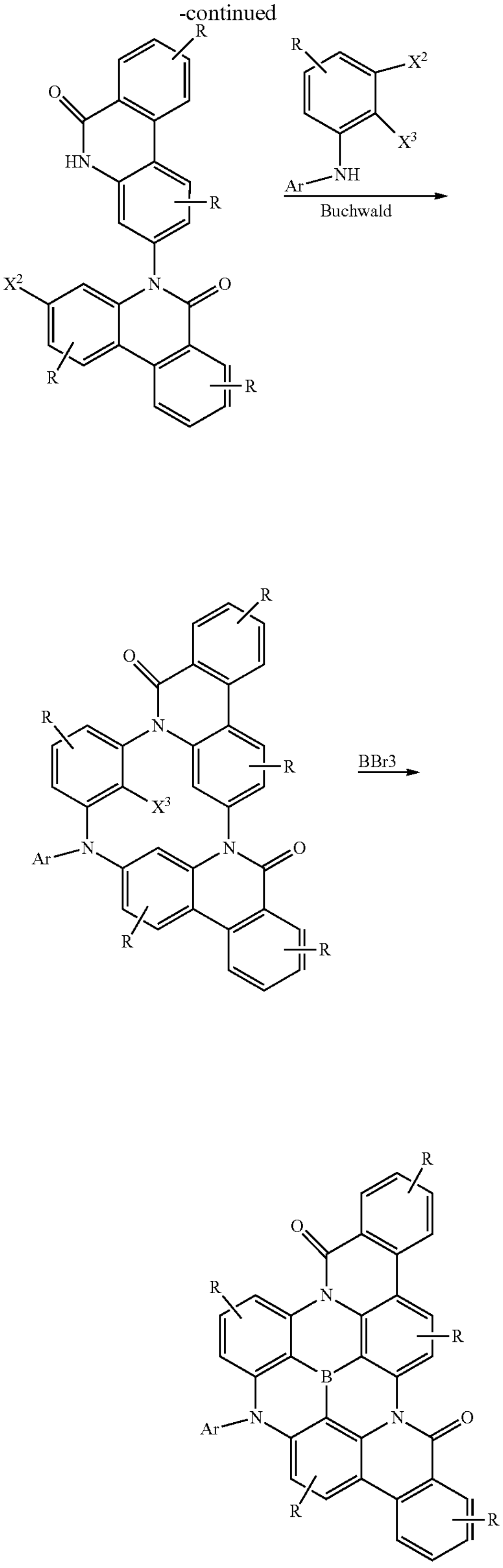
where
$X^1$, $X^2$, $X^3$, Ar and R have the same definition as given in Scheme 1.

Scheme 6

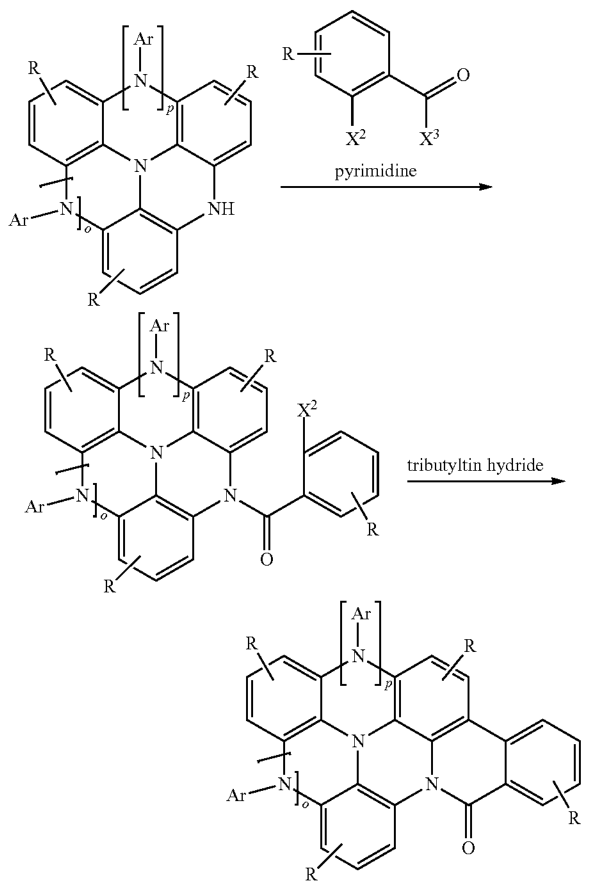

where $X^2$, $X^3$, Ar and R have the same definition as given in Scheme 1 and the indices o and p are, identically or differently, 0 or 1, where p+o=1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example a phosphorescent dopant, a fluorescent dopant, a TADF dopant and/or a matrix material (also called host). Suitable compounds are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure and on the substitution.

Preference is given to an organic electroluminescent device comprising a compound of the formula (1) or in accordance with the preferred embodiments as fluorescent emitters or TADF (Thermally Activated Delayed Fluorescence) emitters. More particularly, the compound of the formula (1) or in accordance with the preferred embodiments is preferably employed as a fluorescent emitter showing prompt fluorescence or as a TADF emitter.

In accordance with another preferred embodiment of the invention, the compound of formula (1) or in accordance with the preferred embodiments is employed in a hyperfluorescent system, as described for example in WO2015/135624, comprising the compound of formula (1) as a fluorescent emitter and a sensitizer compound selected from thermally activated delayed fluorescence compounds (TADF compounds), wherein the energy of the sensitizer is transferred to the fluorescent emitter via Förster resonance energy transfer.

In accordance with still another preferred embodiment of the invention, the compound of formula (1) or in accordance with the preferred embodiments is employed in a hyperphosphorescent system, as described for example in WO2001/08230A1, comprising the compound of formula (1) as a fluorescent emitter, and a sensitizer compound selected from phosphorescent compounds, wherein the energy of the sensitizer is transferred to the fluorescent emitter via Forster resonance energy transfer.

The compounds of formula (1) can also be employed in an electron-transport layer and/or in an electron-blocking or exciton-blocking layer and/or in a hole-transport layer, depending on the precise substitution. The preferred embodiments indicated above also apply to the use of the materials in organic electronic devices.

The compound of formula (1) is particularly suitable for use as a blue emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as a fluorescent emitter or TADF emitter in an emitting layer, it is preferably employed in combination with one or more matrix materials. A matrix material here is taken to mean a material which is present in the emitting layer, preferably as the principal component, and which does not emit light on operation of the device. Preferably, the matrix compound has a glass transition temperature $T_G$ of greater than 70° C., more preferably greater than 90° C., most preferably greater than 110° C.

The proportion of the emitting compound in the mixture of the emitting layer is between 0.1 and 50.0%, preferably between 0.5 and 20.0%, particularly preferably between 1.0 and 10.0%. Correspondingly, the proportion of the matrix material or matrix materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

If the compound of formula (1) or in accordance with the preferred embodiments is employed in an emitting layer as a fluorescent emitter (prompt fluorescence), then the preferred matrix materials for use in combination with the fluorescent emitter are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Particularly preferred matrix materials for use in combination with the compounds of the formula (1) employed as fluorescent emitters in the emitting layer are depicted in the following table:

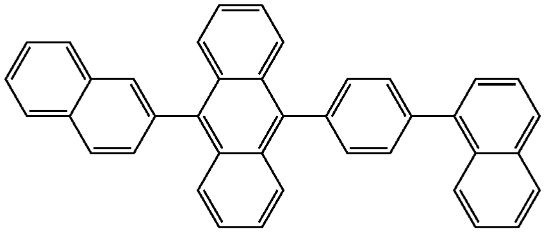

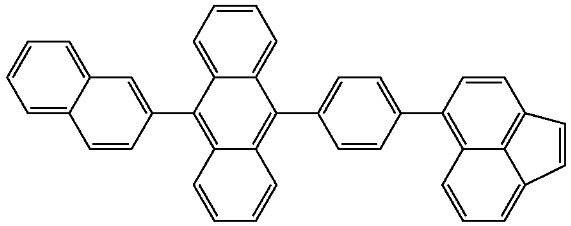

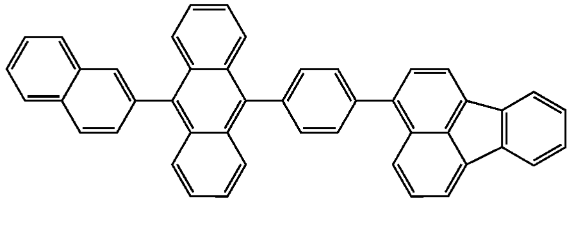

-continued
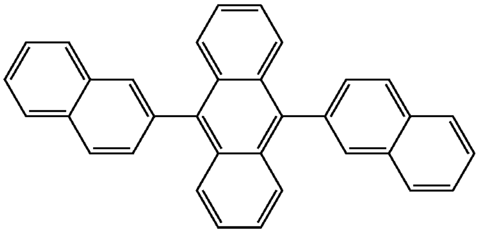
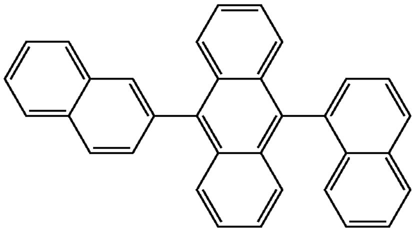
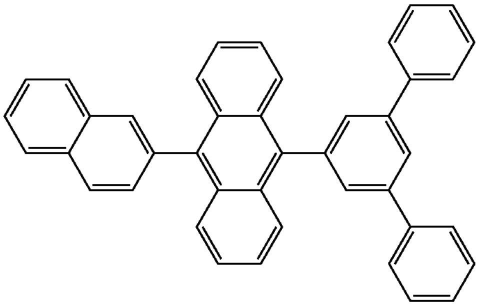
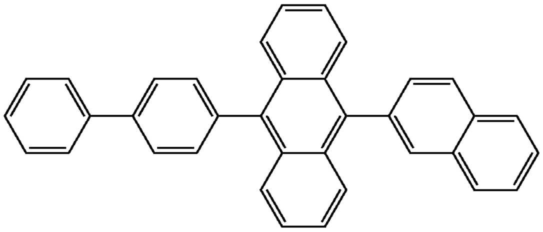
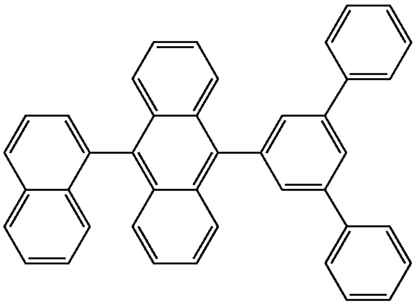
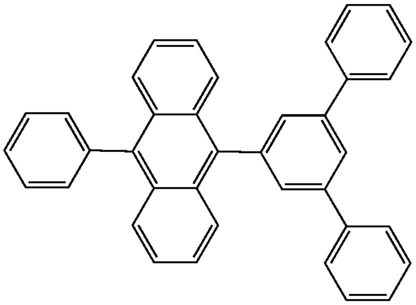
-continued
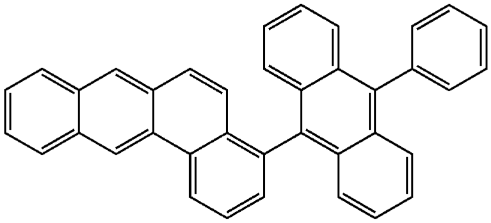
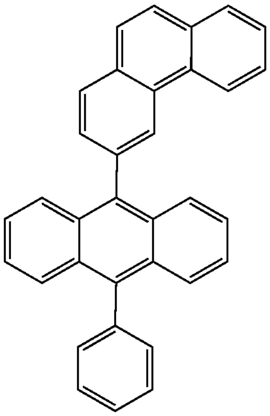
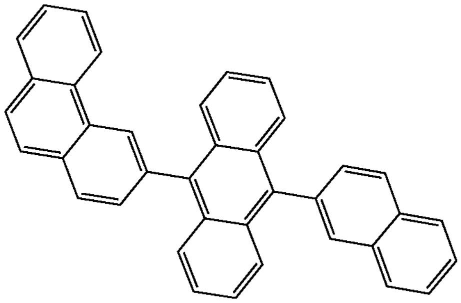
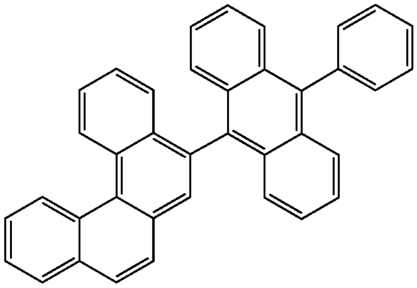
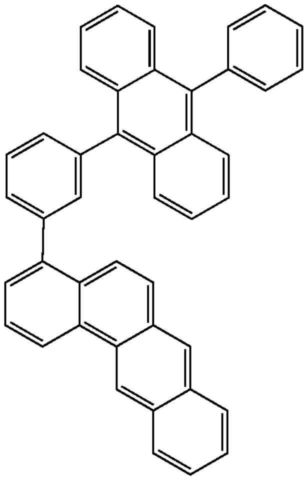

-continued
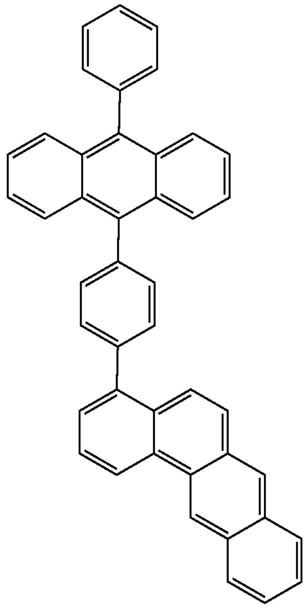
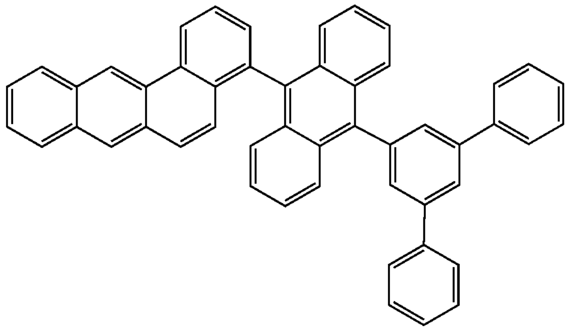
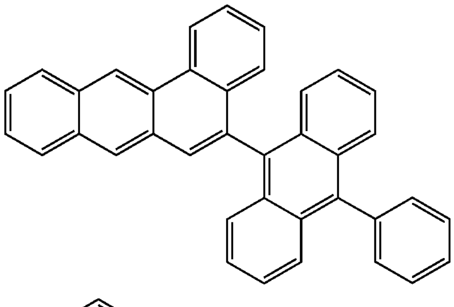
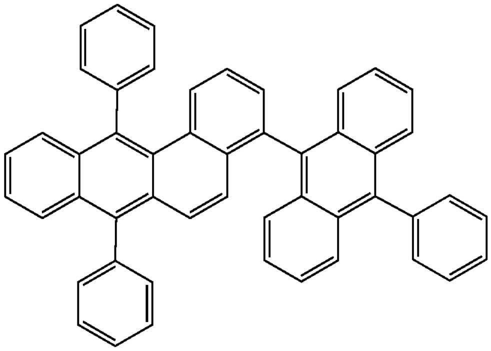
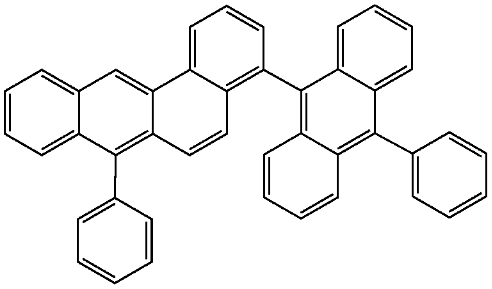
-continued
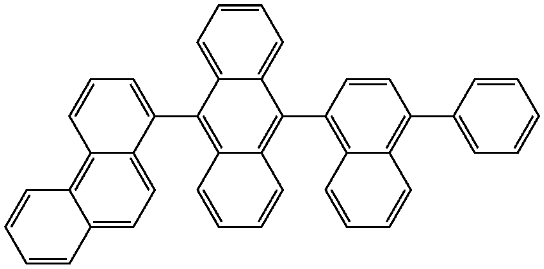
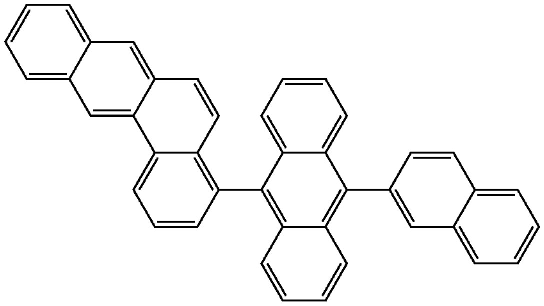
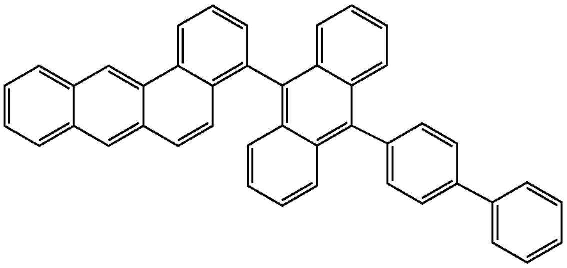
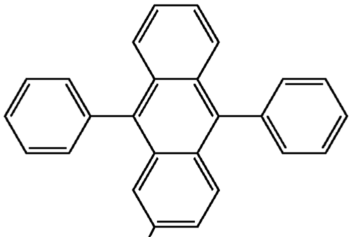
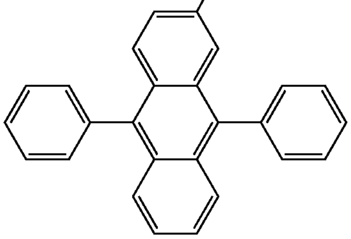

-continued
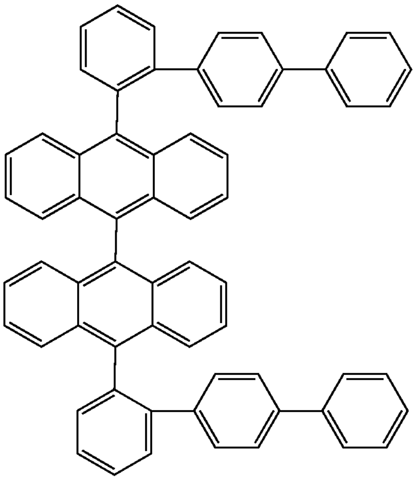
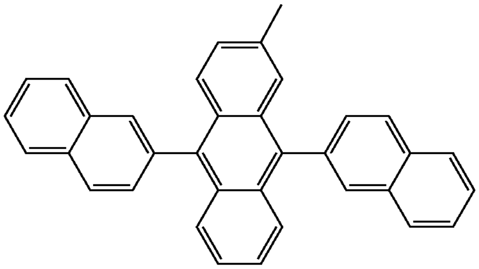
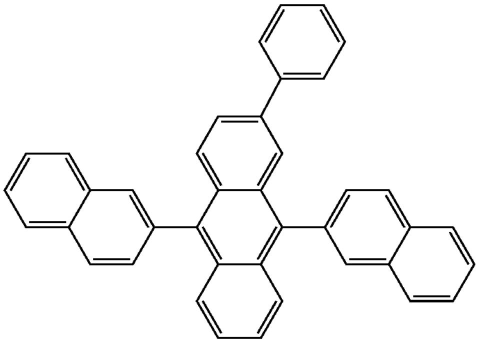
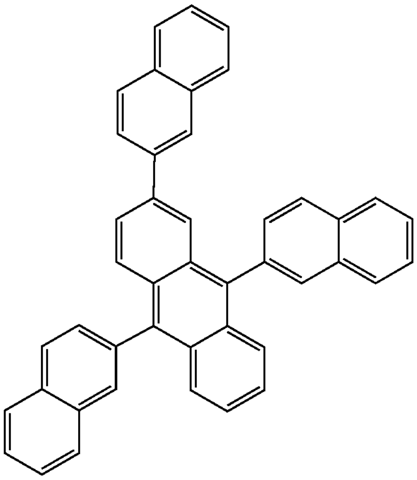
-continued
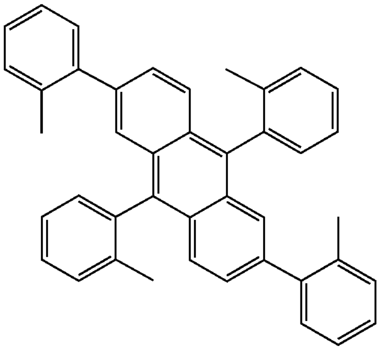
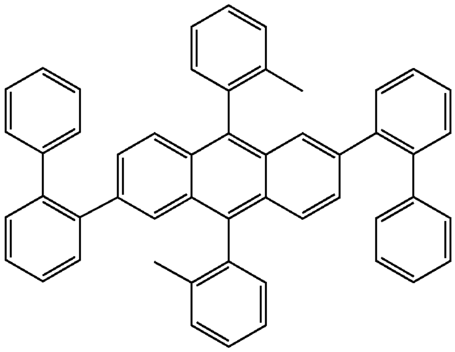
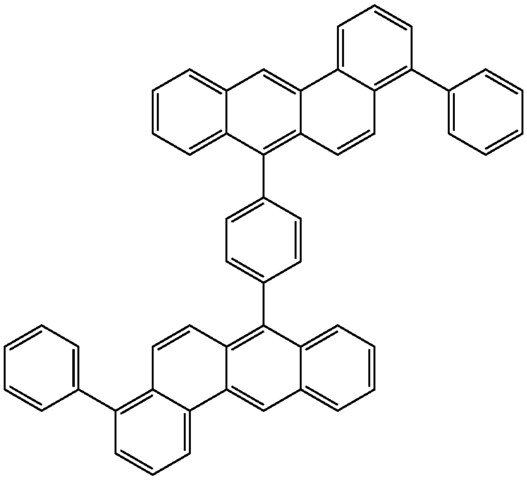
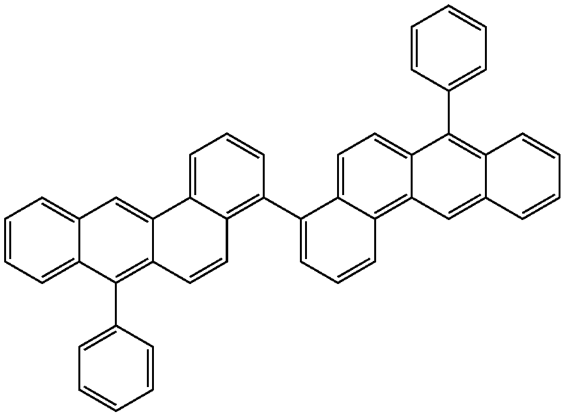

-continued
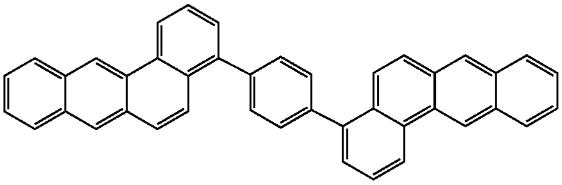
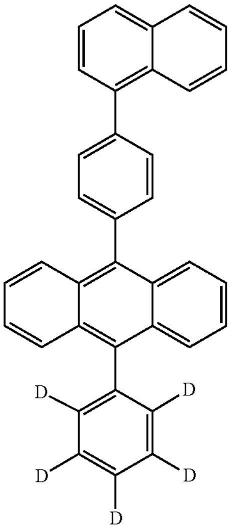
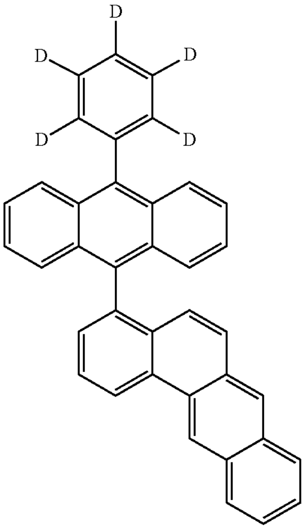
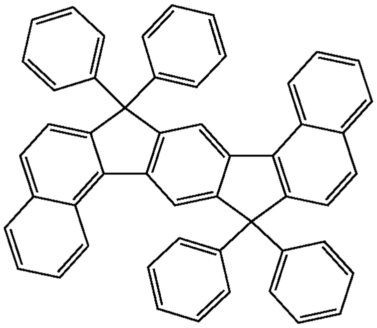
-continued
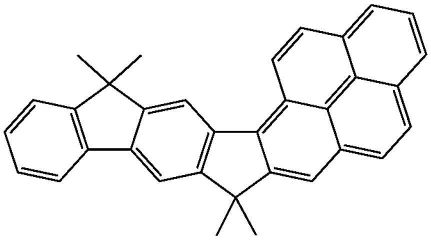
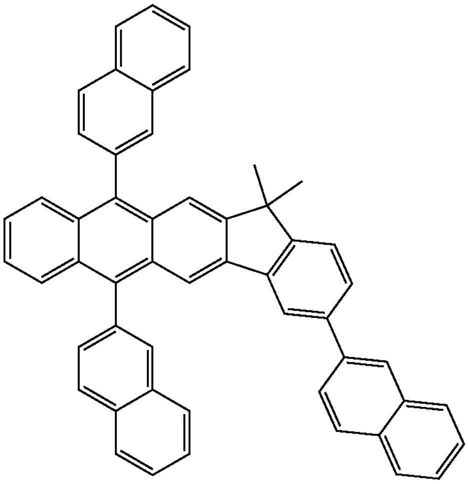
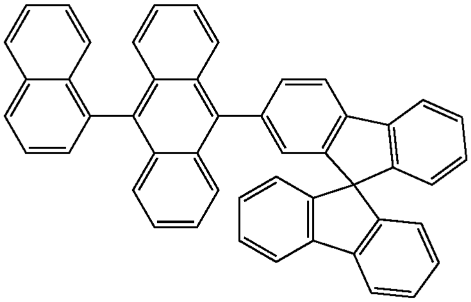
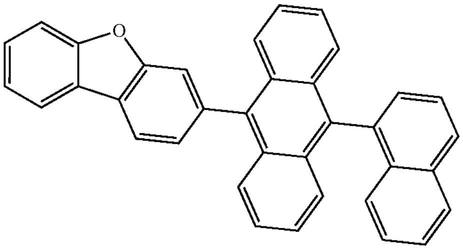
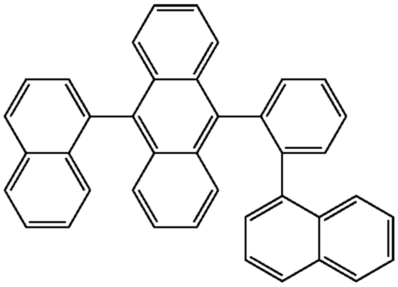

-continued
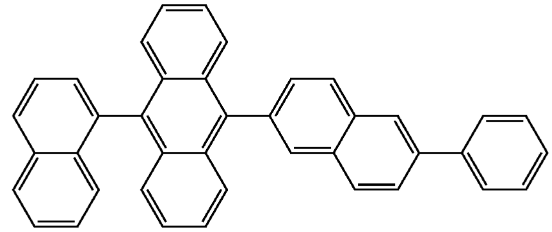
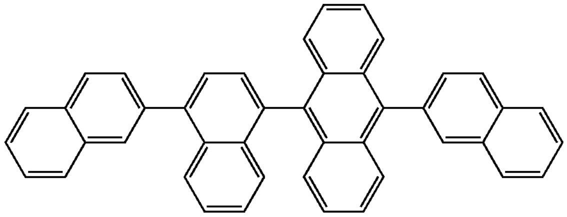
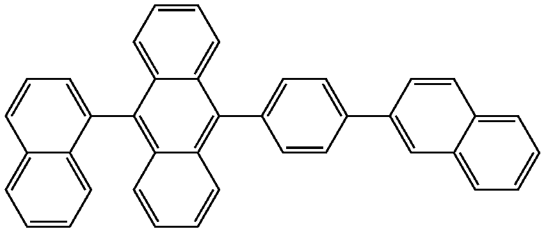
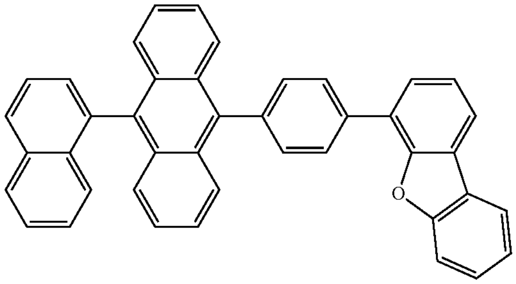
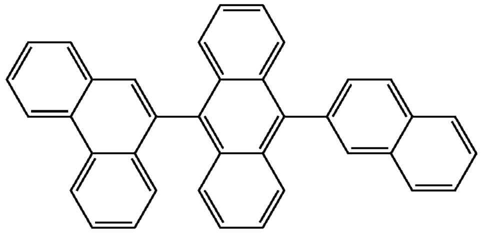
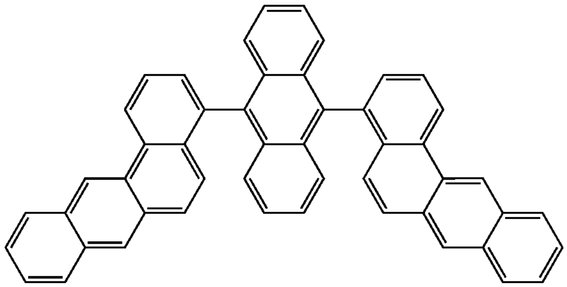
-continued
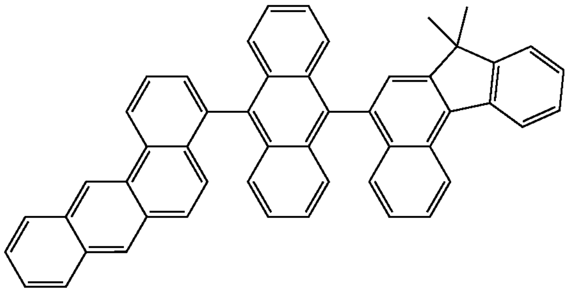
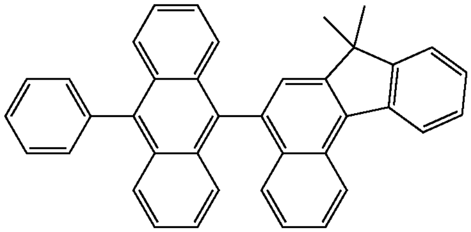
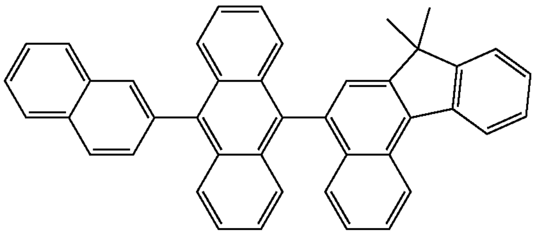
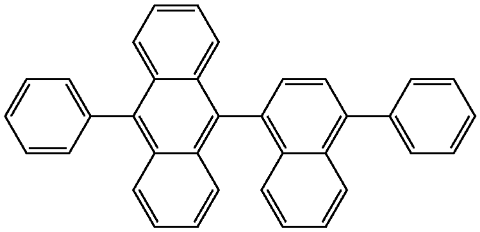
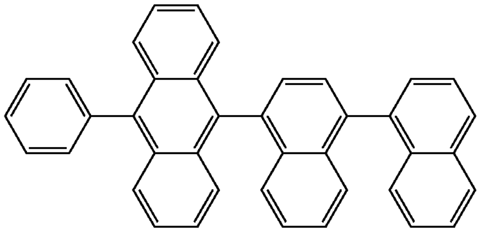
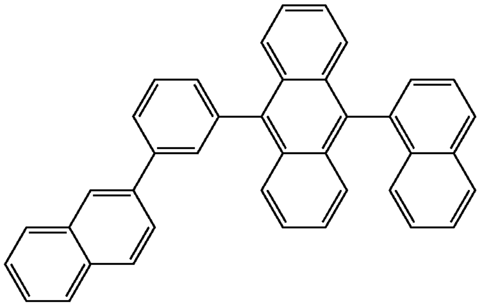

-continued
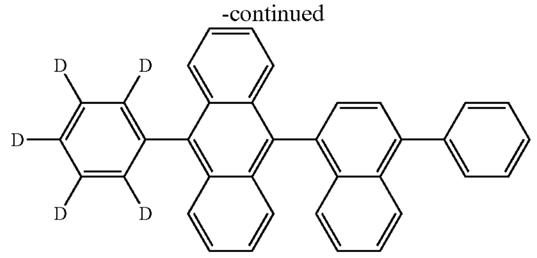
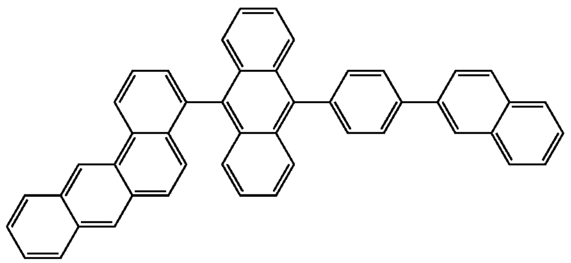
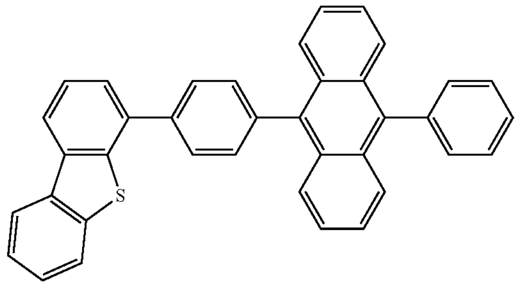
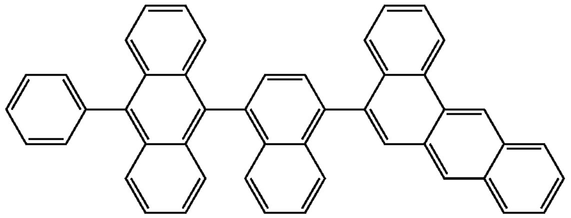
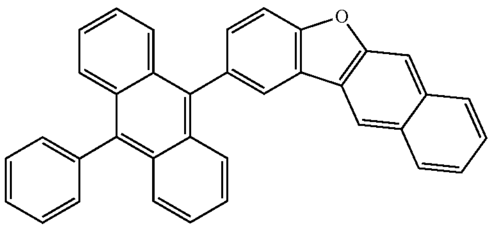
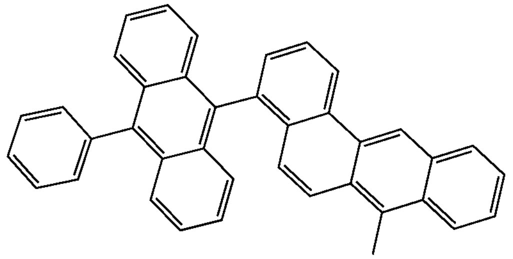
-continued
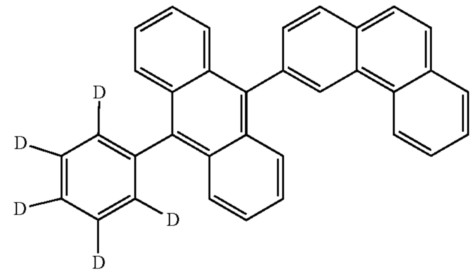
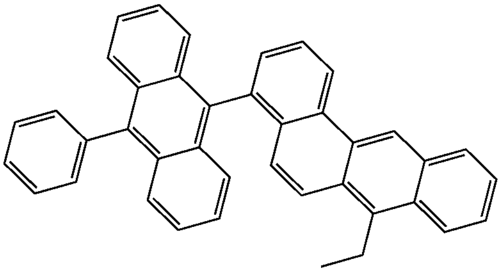
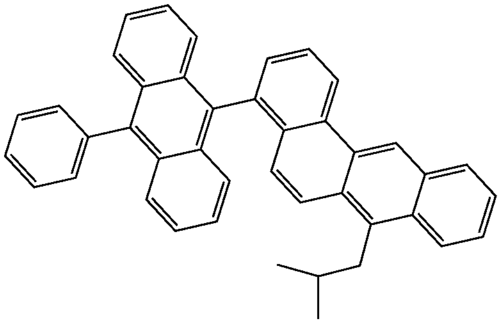
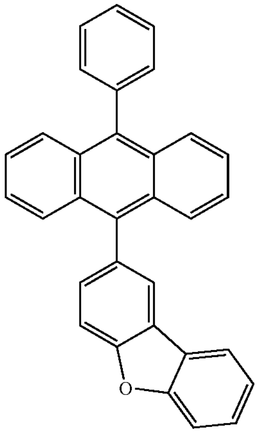

-continued

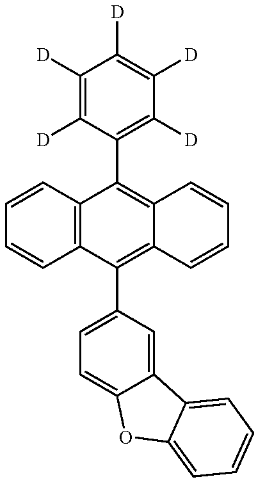

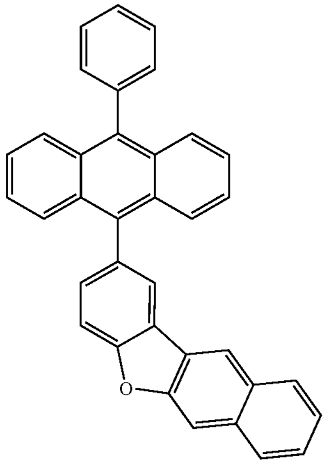

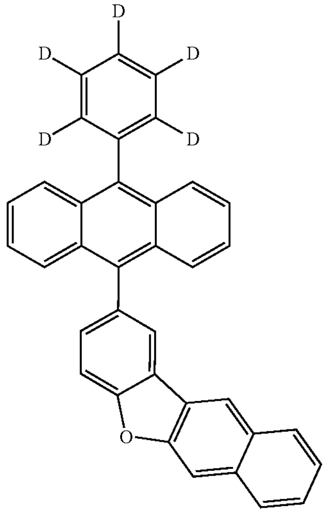

If the compound according to the invention is employed as a fluorescent emitting compound in an emitting layer, it may be employed in combination with one or more other fluorescent emitting compounds.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorene-diamines, for example in accordance with WO 2007/140847, and the indenofluorene derivatives containing condensed aryl groups which are disclosed in WO 2010/012328. Still further preferred emitters are benzanthracene derivatives as disclosed in WO 2015/158409, anthracene derivatives as disclosed in WO 2017/036573, fluorene dimers like in WO 2016/150544 or phenoxazine derivatives as disclosed in WO 2017/028940 and WO 2017/028941. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in WO 2014/106522 and the indenofluorenes disclosed in WO 2014/111269 or WO 2017/036574.

Examples of preferred fluorescent emitting compounds, besides the compounds according to the invention, which can be used in combination with the compounds of the invention in an emitting layer or which can be used in another emitting layer of the same device are depicted in the following table:

105
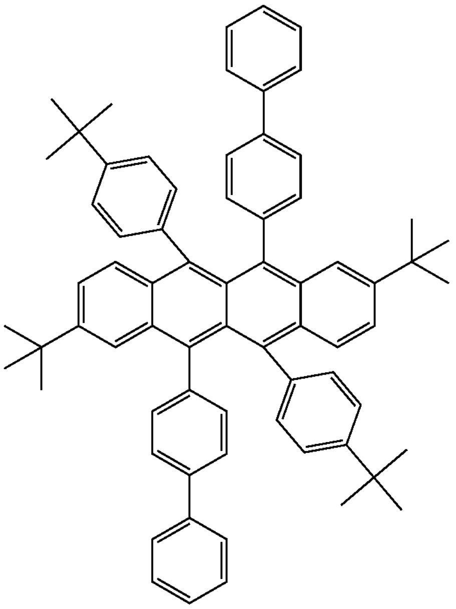
106
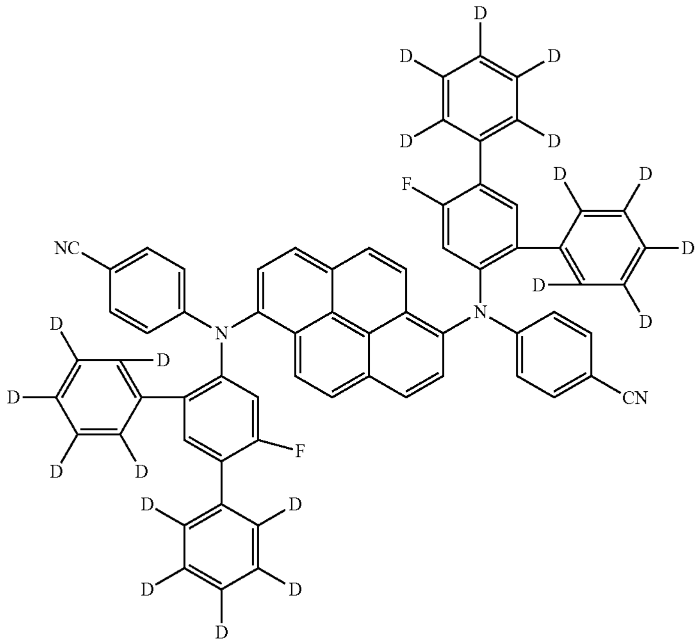
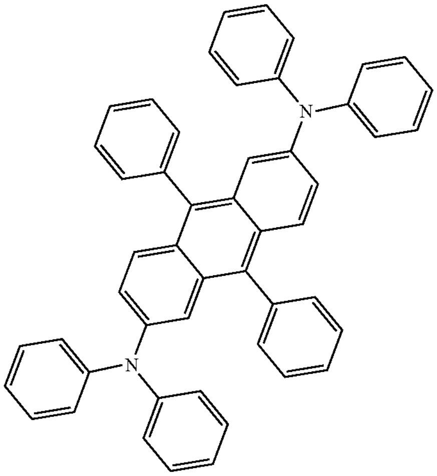
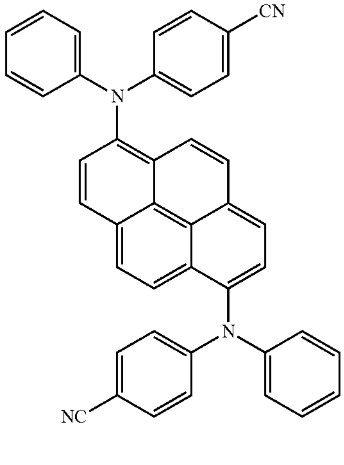
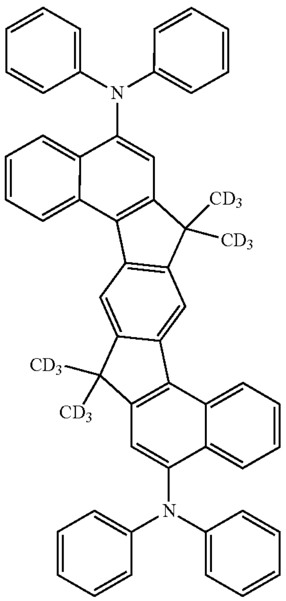

-continued
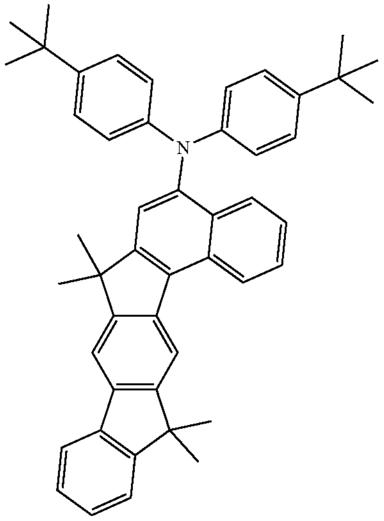
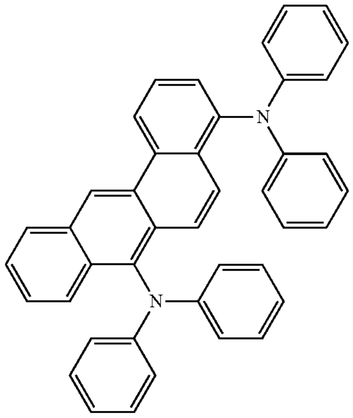
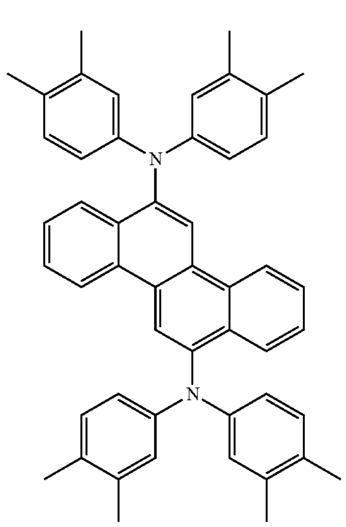
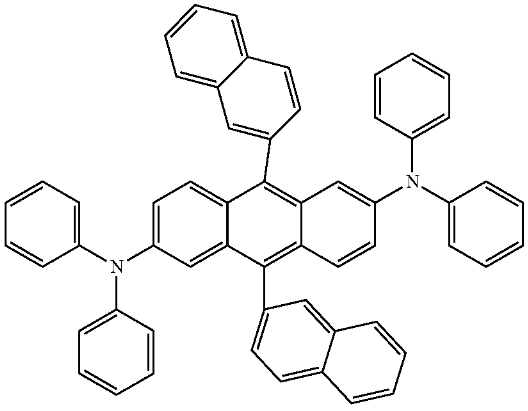
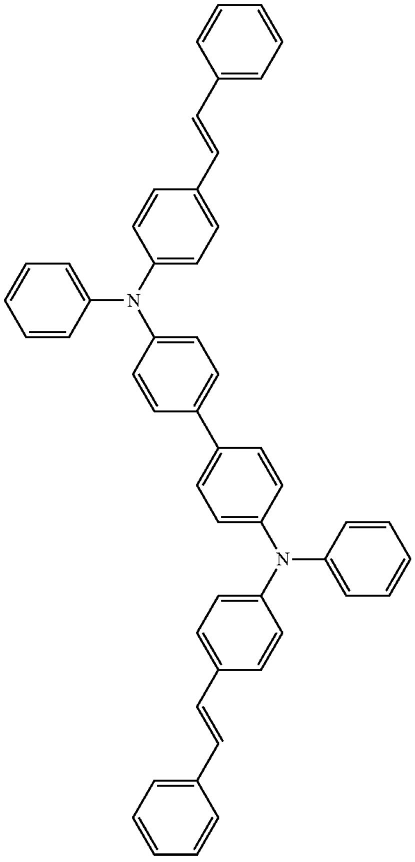
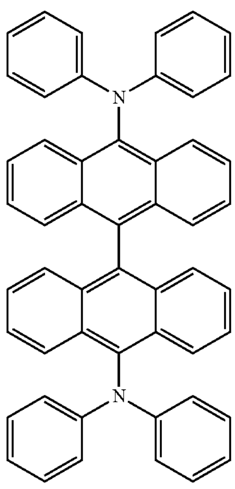

-continued
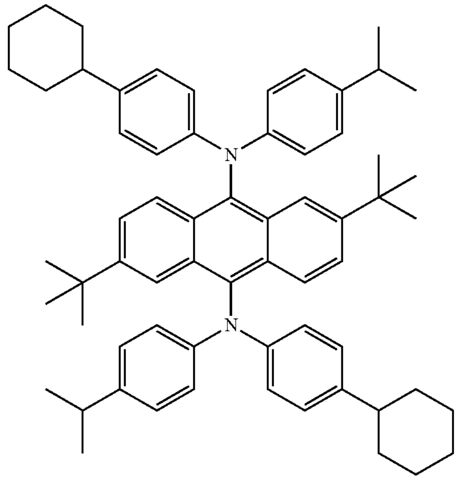
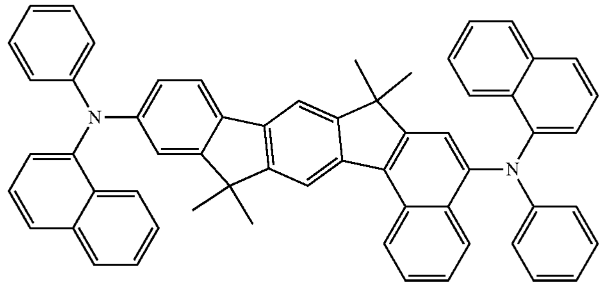
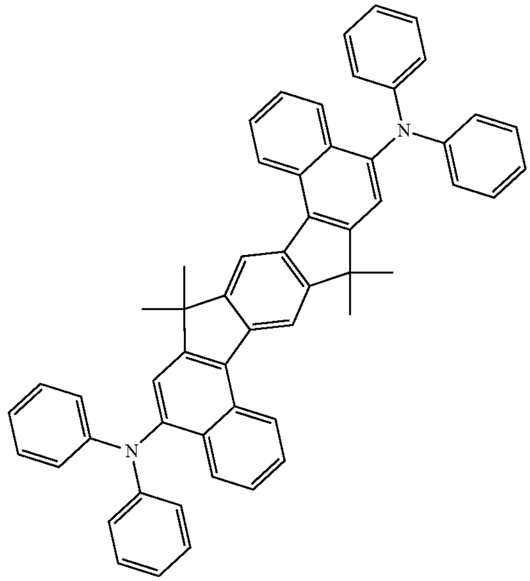
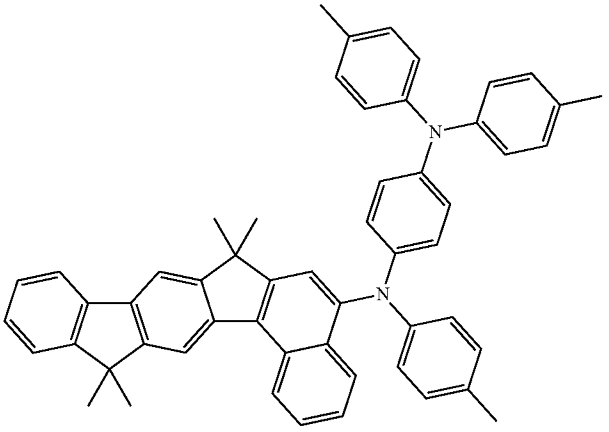
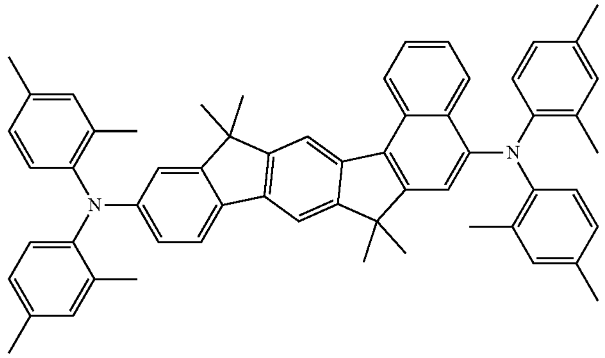
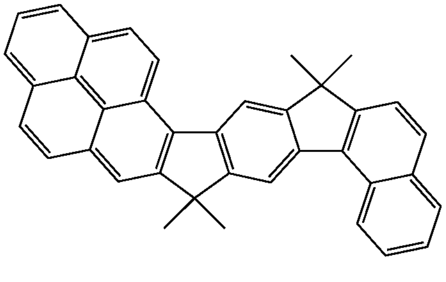

-continued
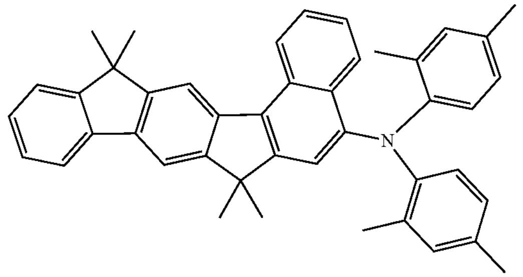
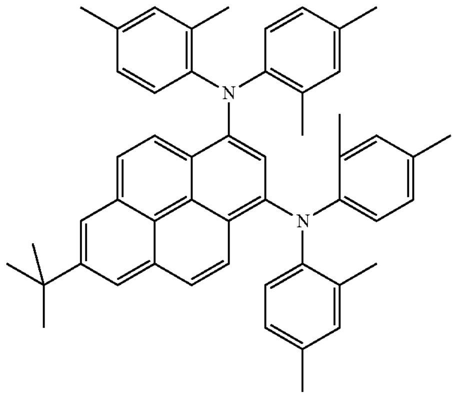
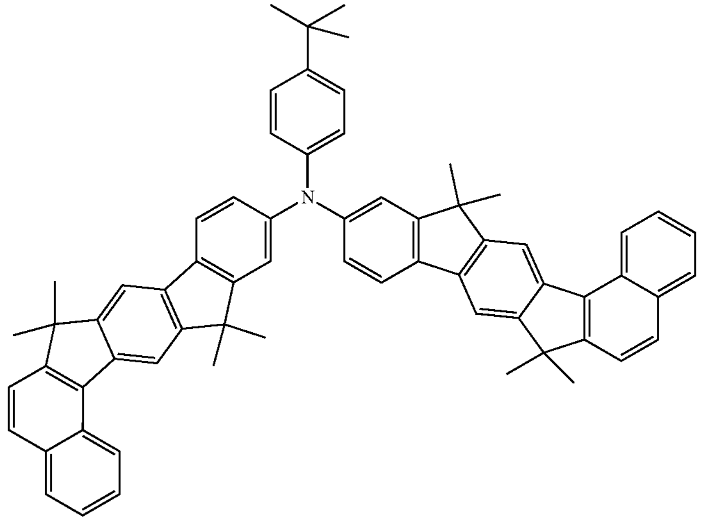
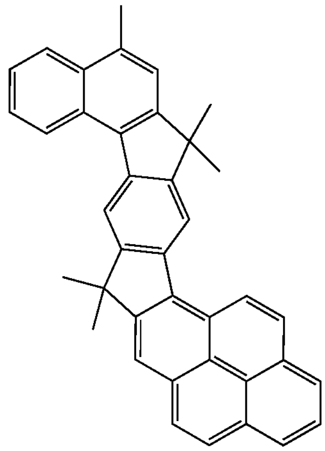
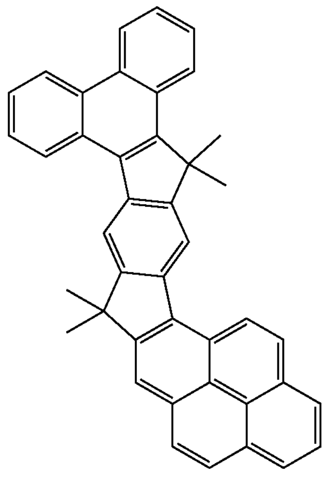
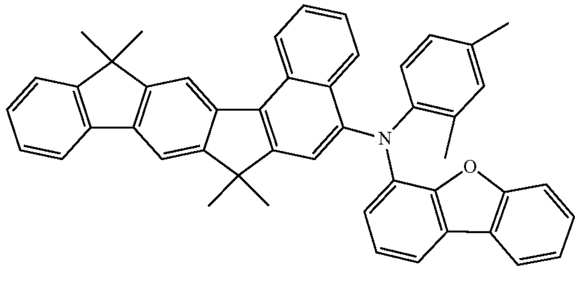

-continued
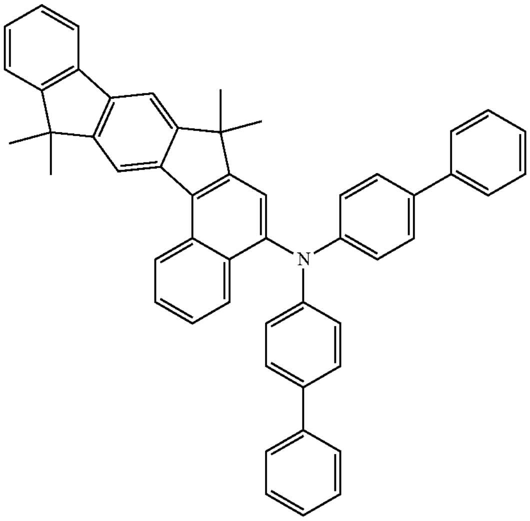
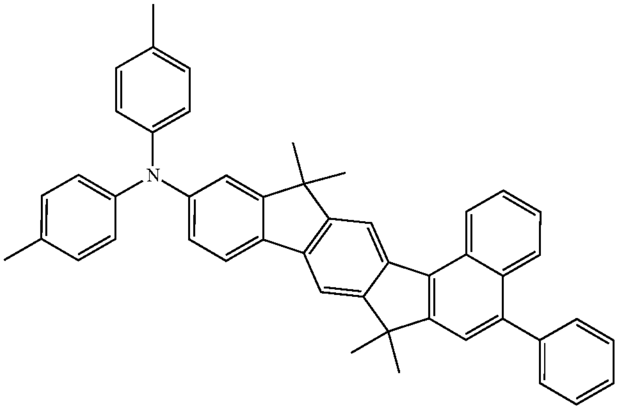
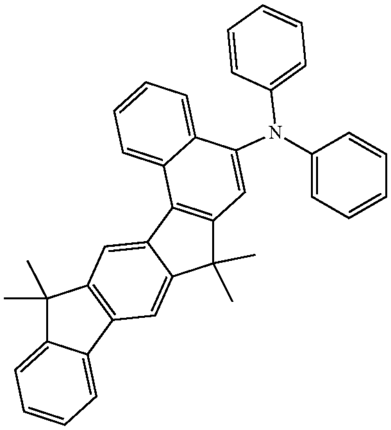
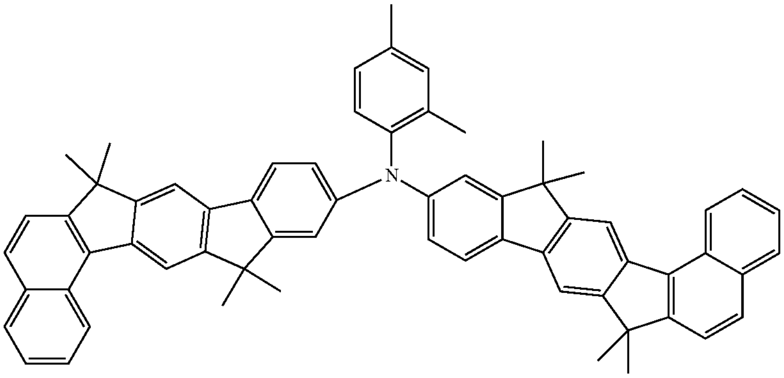
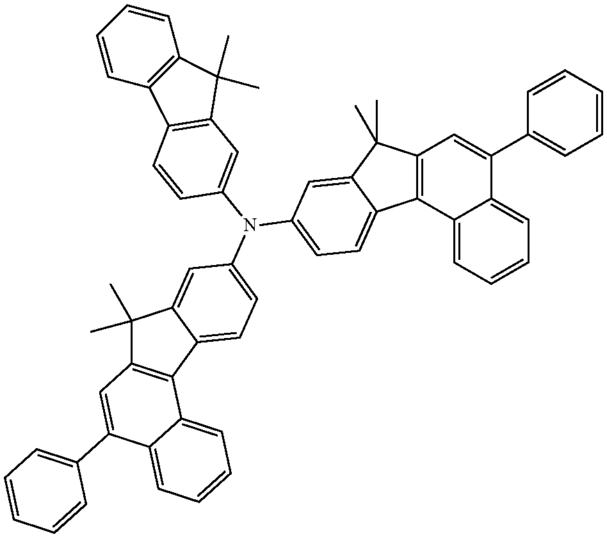

-continued
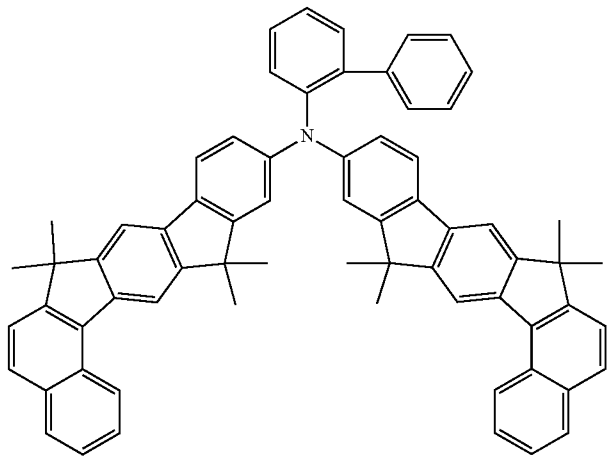
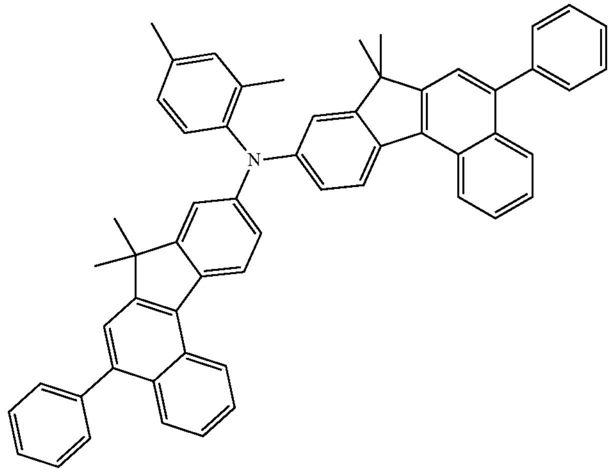
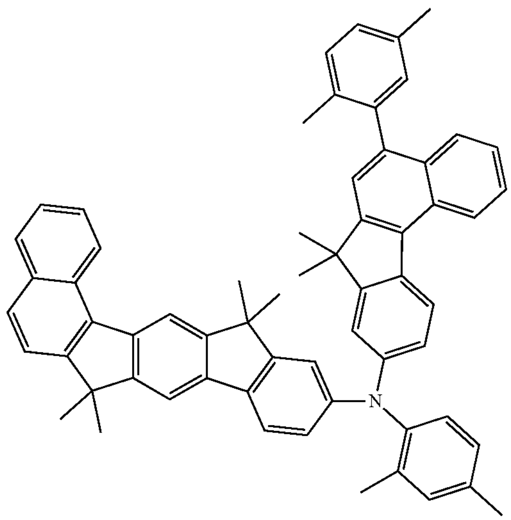
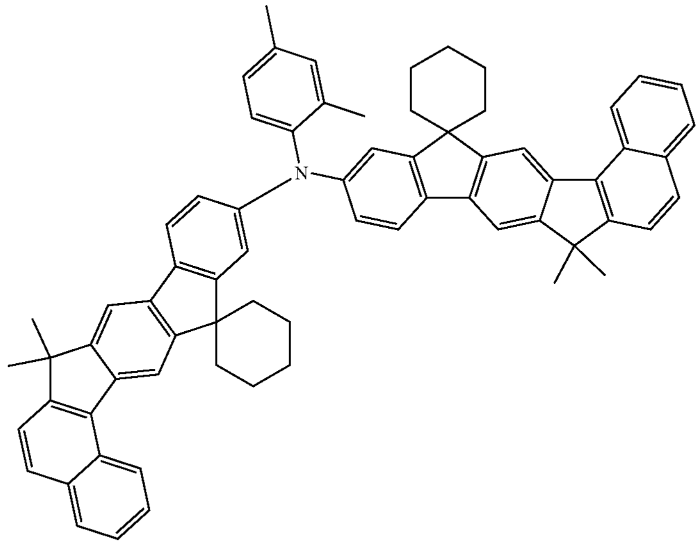

-continued
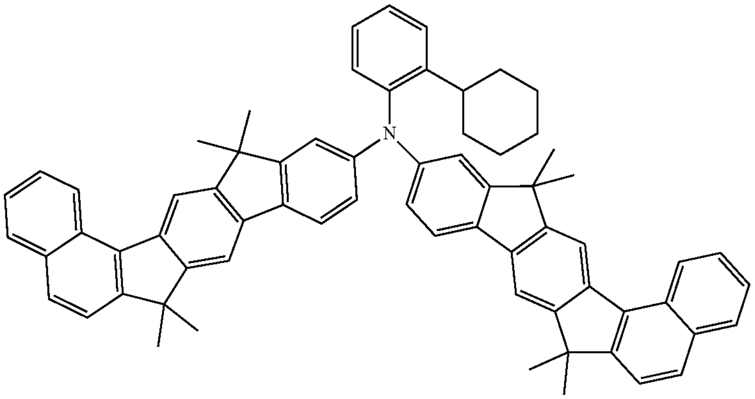
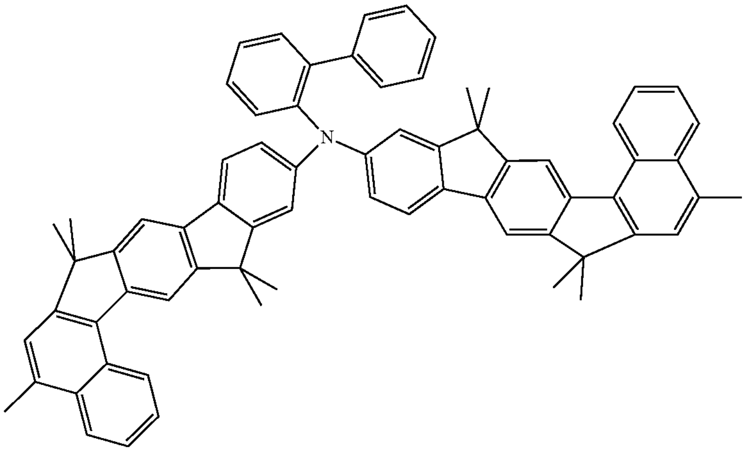
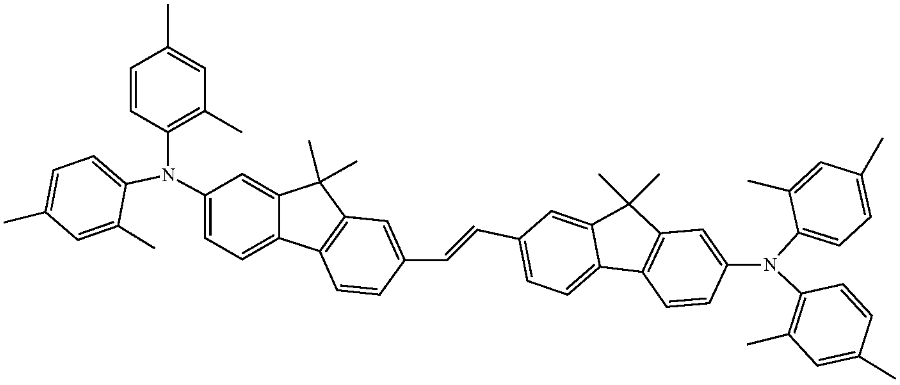
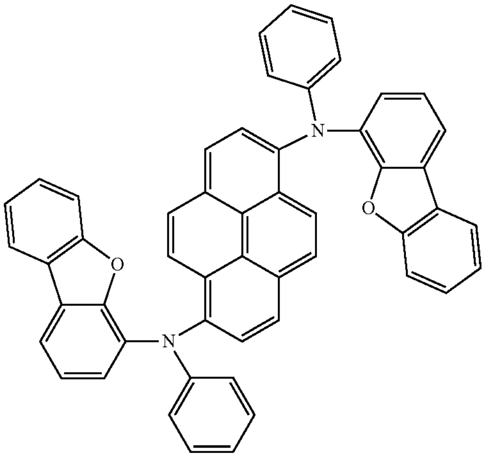
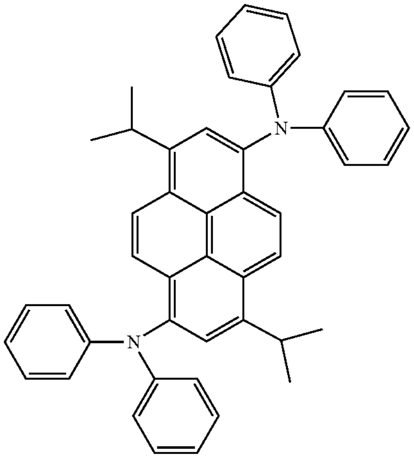

-continued
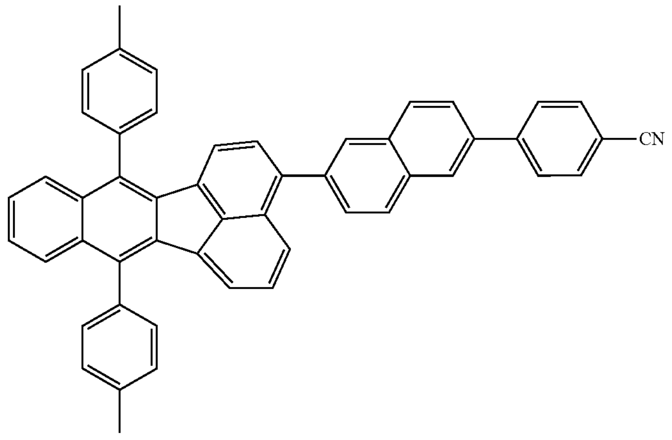
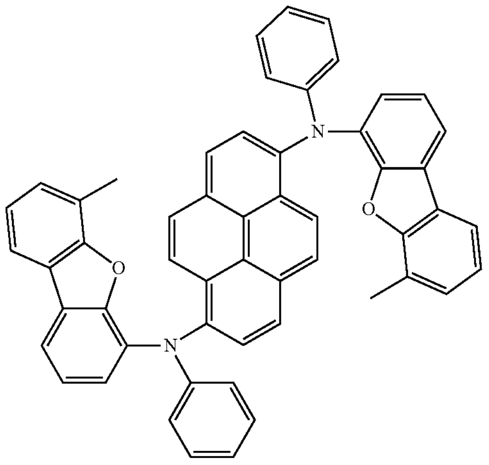
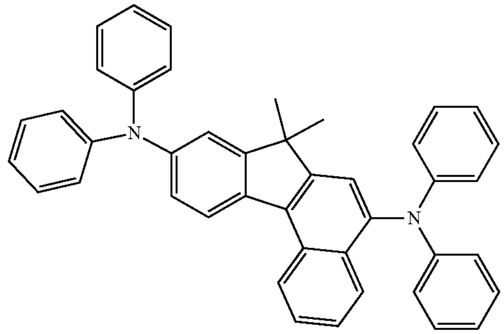
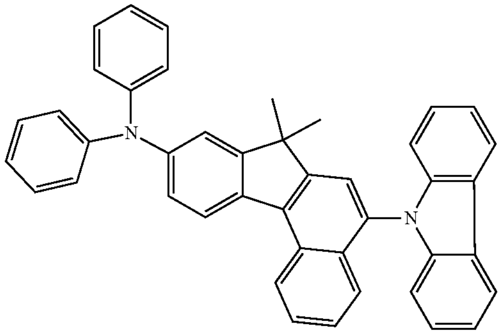
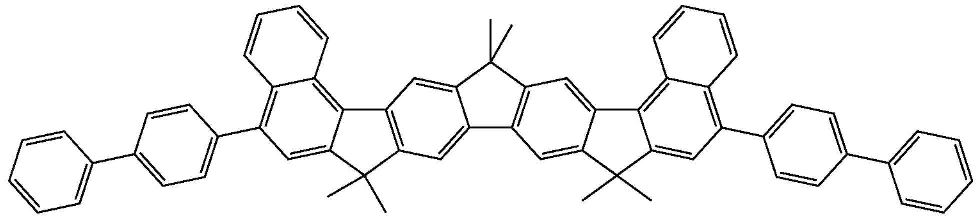
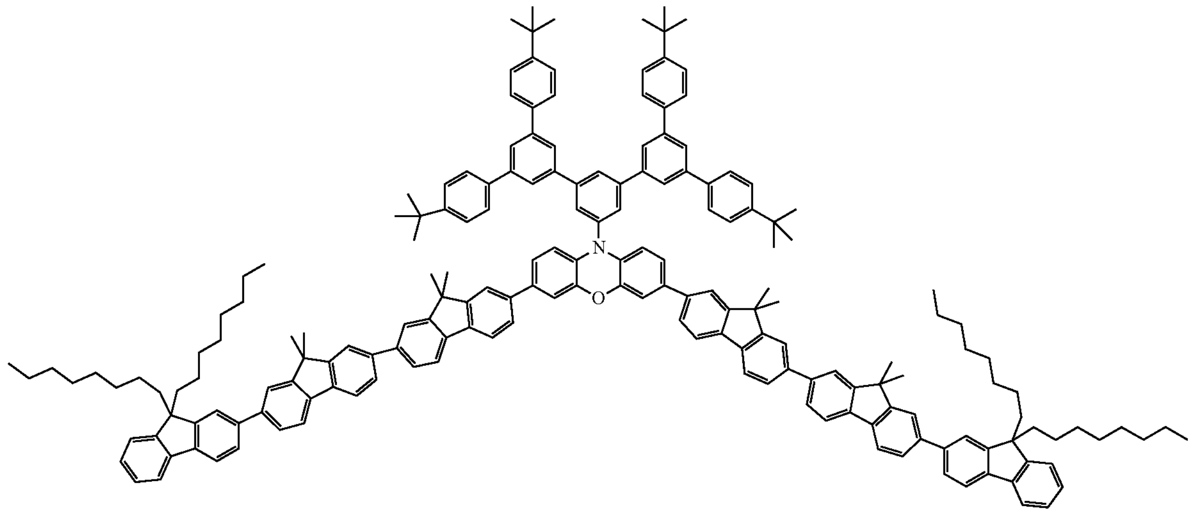

-continued
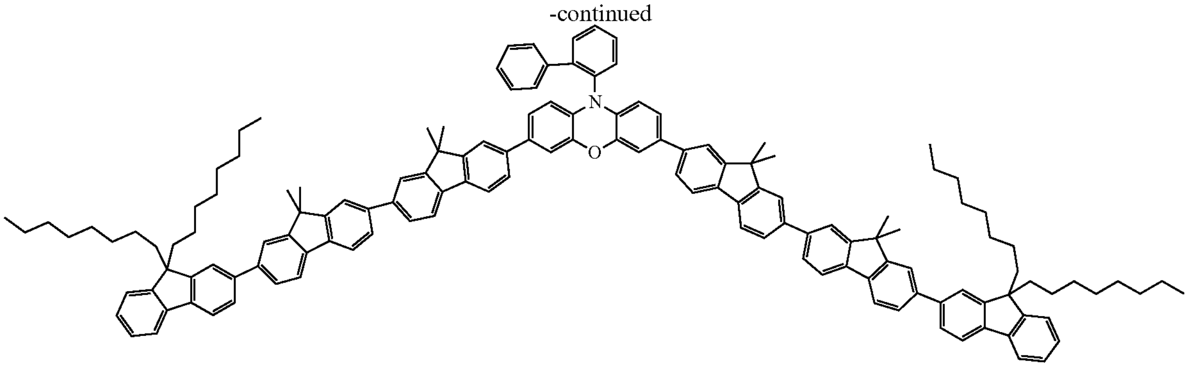
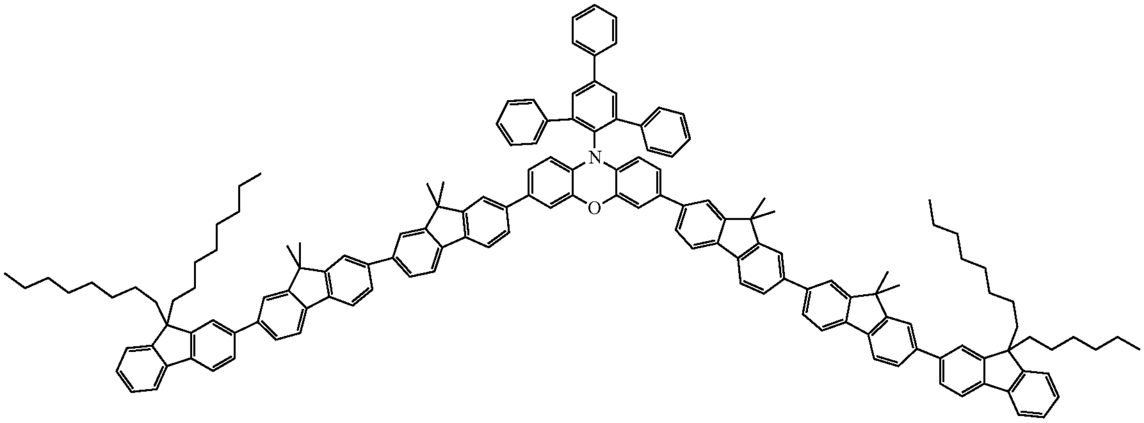
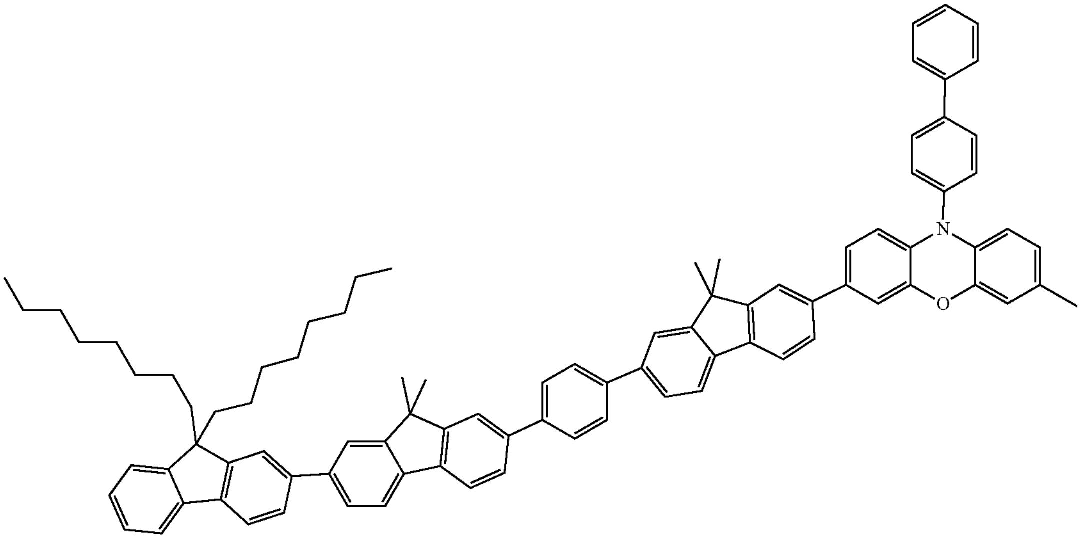

-continued

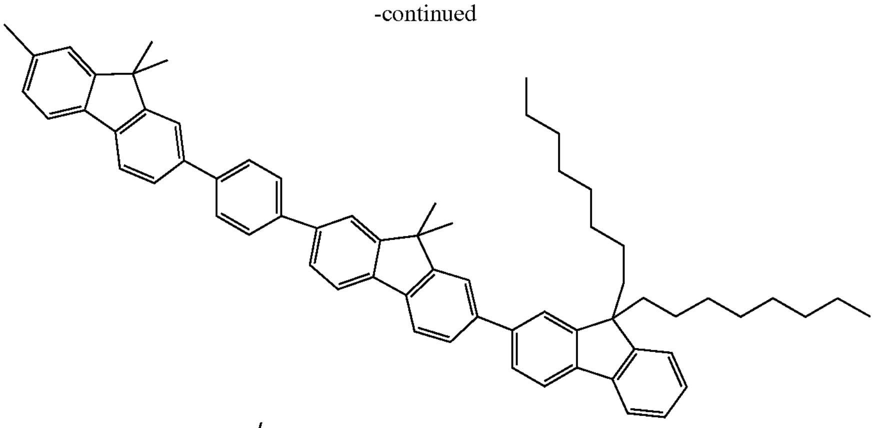

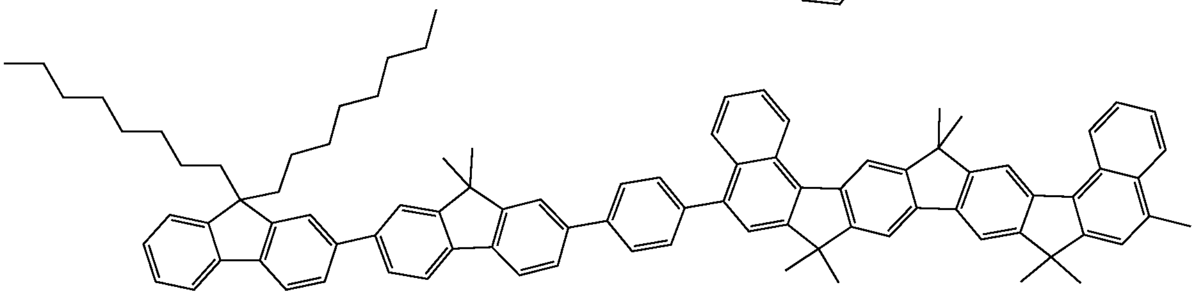

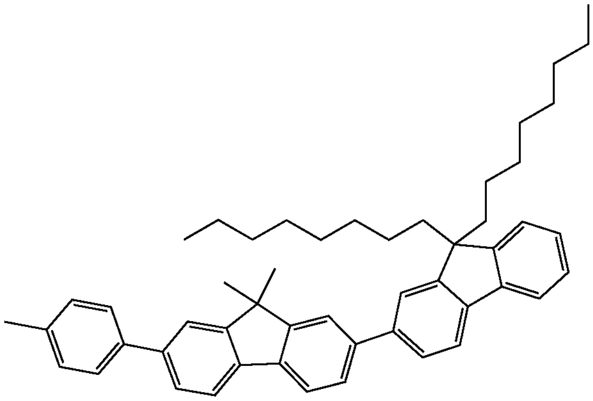

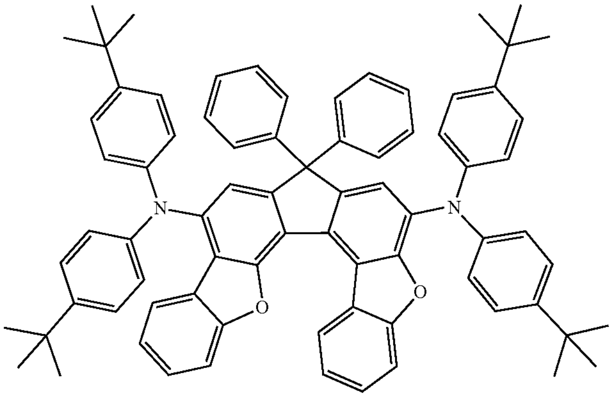

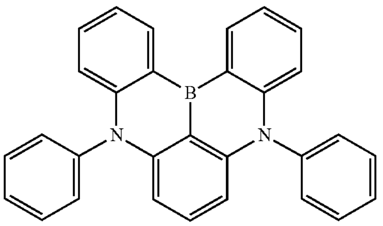

If the compound of formula (1) or in accordance with the preferred embodiments is employed in an emitting layer as a TADF emitter, then the preferred matrix materials for use in combination with the TADF emitter are selected from the classes of the ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, dibenzofuran derivatives, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, pyrimidine derivatives, quinoxaline derivatives, Zn complexes, Al complexes or Be complexes, for example according to EP 652273 or WO 2009/062578, or bridged carbazole derivatives, for example according to US 2009/0136779, WO 2010/050778, WO 2011/042107 or WO 2011/088877. Suitable matrix materials are also those described in WO 2015/135624. These are incorporated into the present invention by reference. It is also possible to use mixtures of two or more of these matrix materials.

The matrix compounds for TADF emitters are preferably charge-transporting, i.e. electron-transporting or hole-transporting, or bipolar compounds. Matrix compounds used may additionally also be compounds which are neither hole-nor electron-transporting in the context of the present application. An electron-transporting compound in the context of the present invention is a compound having a LUMO$\leq$−2.50 eV. Preferably, the LUMO is $\leq$−2.60 eV, more preferably $\leq$−2.65 eV, most preferably $\leq$−2.70 eV. The LUMO is the lowest unoccupied molecular orbital. The value of the LUMO of the compound is determined by quantum-chemical calculation, as described in general terms in the examples section at the back. A hole-transporting compound in the context of the present invention is a compound having a HOMO $\geq$−5.5 eV. The HOMO is preferably $\geq$−5.4 eV, more preferably $\geq$−5.3 eV. The HOMO is the highest occupied molecular orbital. The value of the HOMO of the compound is determined by quantum-chemical calculation, as described in general terms in the examples section at the back. A bipolar compound in the context of the present invention is a compound which is both hole- and electron-transporting.

Suitable electron-conducting matrix compounds for TADF emitters are selected from the substance classes of the triazines, the pyrimidines, the lactams, the metal complexes, especially the Be, Zn and Al complexes, the aromatic ketones, the aromatic phosphine oxides, the azaphospholes, the azaboroles substituted by at least one electron-conducting substituent, and the quinoxalines. In a preferred embodiment of the invention, the electron-conducting compound is a purely organic compound, i.e. a compound containing no metals.

Furthermore, the hyperfluorescent and hyperphosphorescent systems as mentioned above preferably comprise, additionally to the sensitizer and the fluorescent emitter, at least one matrix material. In this case, it is preferable that the lowest triplet energy of the matrix compound is not more than 0.1 eV lower than the triplet energy of the sensitizer compound.

Especially preferably, $T_1$(matrix)$\geq T_1$(sensitizer).

More preferably: $T_1$(matrix)$-T_1$(sensitizer)$\geq$0.1 eV;

most preferably: $T_1$(matrix)$-T_1$(sensitizer)$\geq$0.2 eV.

$T_1$(matrix) here is the lowest triplet energy of the matrix compound and $T_1$(sensitizer) is the lowest triplet energy of the sensitizer compound. The triplet energy of the matrix compound $T_1$(matrix) is determined here from the edge of the photoluminescence spectrum measured at 4 K of the neat film. $T_1$(sensitizer) is determined from the edge of the photoluminescence spectrum measured at room temperature in toluene solution.

Suitable matrix materials for hyperfluorescent or hyperphosphorescent systems are the same matrix materials as mentioned above, more preferred are the matrix materials that are also preferred for TADF materials.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

More particularly, when the phosphorescent compound is employed in a hyperphosphorescent system as described above, the phosphorescent compound is preferably selected from the phosphorescent organometallic complexes, which are described, for example, in WO2015/091716. Also particularly preferred are the phosphorescent organometallic complexes, which are described in WO2000/70655, WO2001/41512, WO2002/02714, WO2002/15645, EP1191612, WO2005/033244, WO2005/019373, US2005/0258742, WO2006/056418, WO2007/115970, WO2007/115981, WO2008/000727, WO2009/050281, WO2009/050290, WO2011/051404, WO2011/073149, WO2012/121936, US2012/0305894, WO2012/170571, WO2012/170461, WO2012/170463, WO2006/121811, WO2007/095118, WO2008/156879, WO2008/156879, WO2010/068876, WO2011/106344, WO2012/172482, EP3126371, WO2015/014835, WO2015/014944, WO2016/020516, US20160072081, WO2010/086089, WO2011/044988, WO2014/008982, WO2014/023377, WO2014/094961, WO2010/069442, WO2012/163471, WO2013/020631, US20150243912, WO2008/000726, WO2010/015307, WO2010/054731, WO2010/054728, WO2010/099852, WO2011/032626, WO2011/157339, WO2012/007086, WO2015/036074, WO2015/104045, WO2015/117718, WO2016/015815, which are preferably iridium and platinum complexes.

Particularly preferred are also the phosphorescent organometallic complexes having polypodal ligands as described, for example, in WO2004/081017, WO2005/042550, US2005/0170206, WO2009/146770, WO2010/102709, WO2011/066898, WO2016124304, WO2017/032439, WO2018/019688, EP3184534 and WO2018/011186.

Particularly preferred are also the phosphorescent binuclear organometallic complexes as described, for example, in WO2011/045337, US20150171350, WO2016/079169, WO2018/019687, WO2018/041769, WO2018/054798, WO2018/069196, WO2018/069197, WO2018/069273.

Particularly preferred are also the copper complexes as described, for example, in WO2010/031485, US2013150581, WO2013/017675, WO2013/007707, WO2013/001086, WO2012/156378, WO2013/072508, EP2543672.

Explicit examples of phosphorescent sensitizers are $Ir(ppy)_3$ and its derivatives as well as the structures listed below:

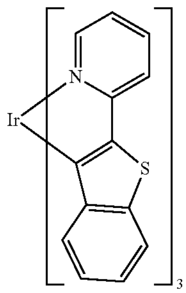
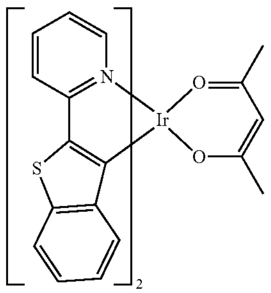
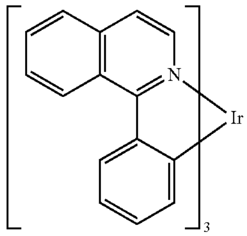
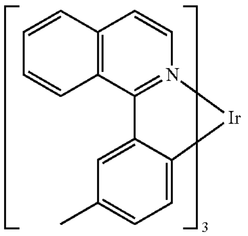

-continued

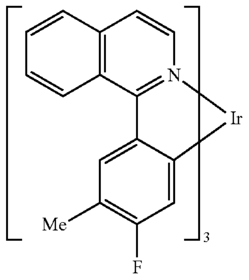
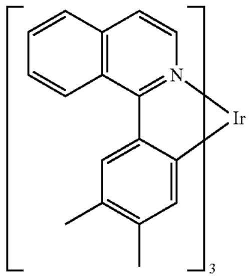
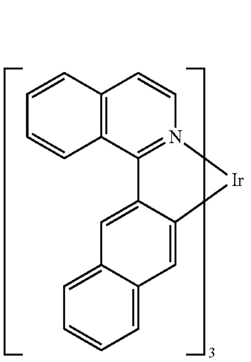
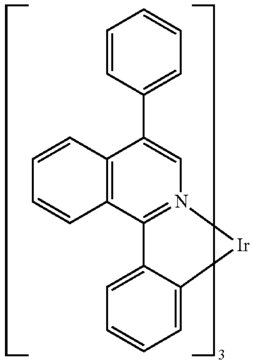
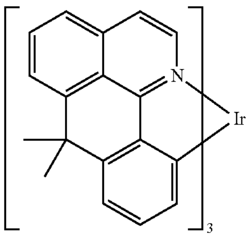
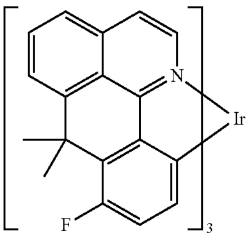
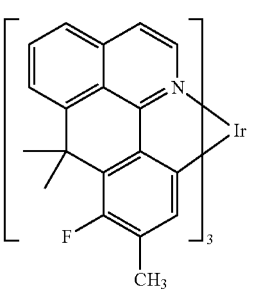
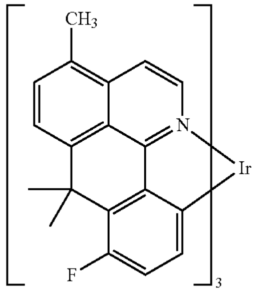
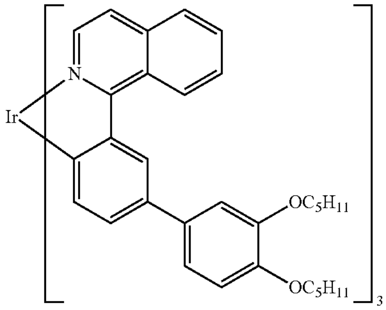

-continued
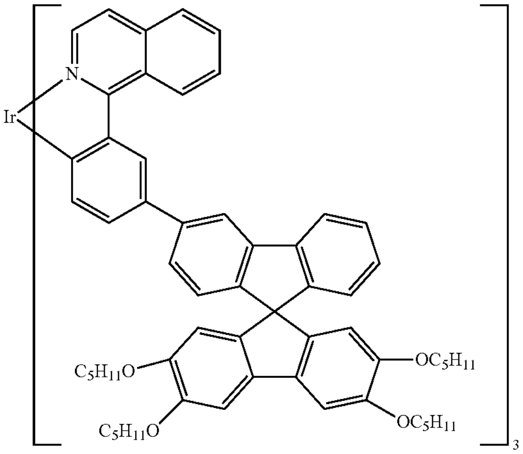
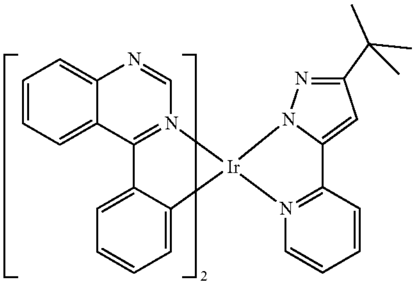
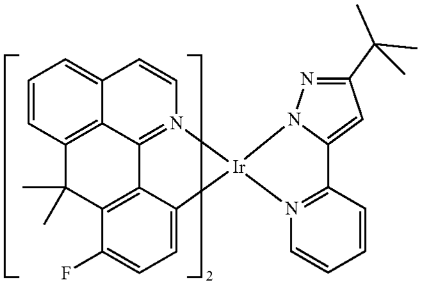
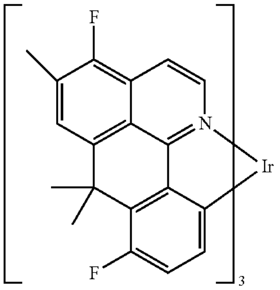
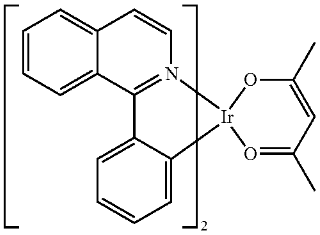
-continued
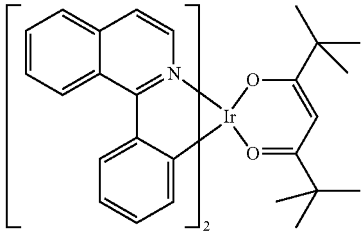
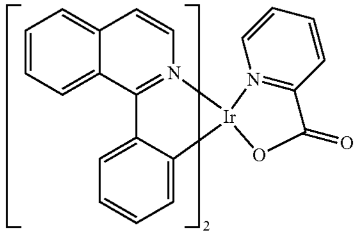
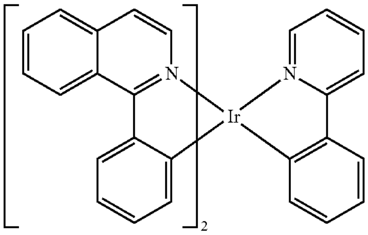
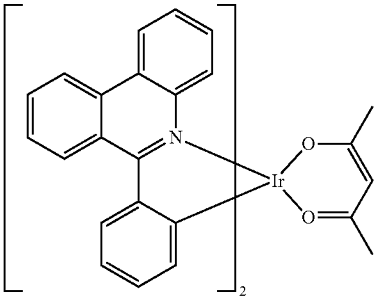
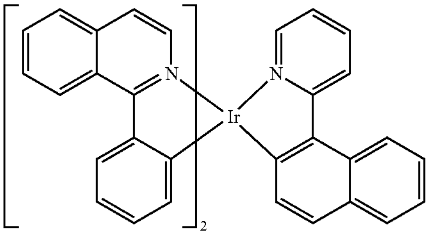
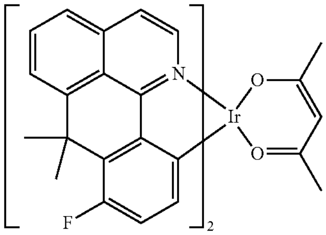

-continued
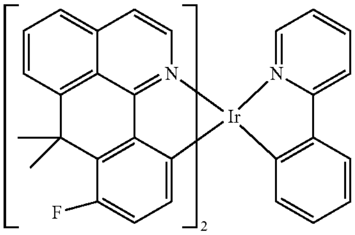
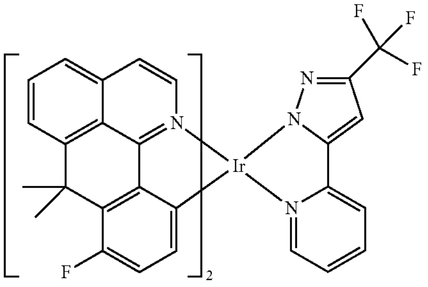
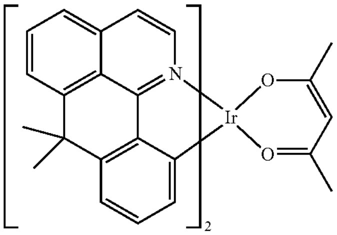
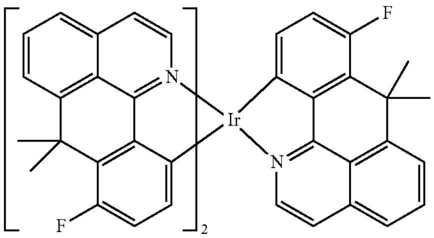
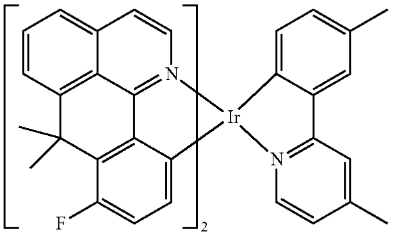
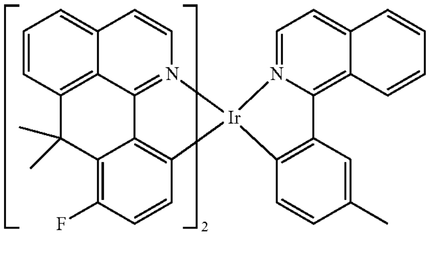
-continued
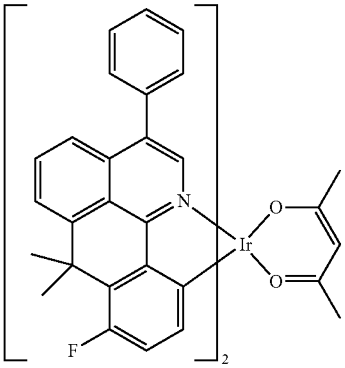
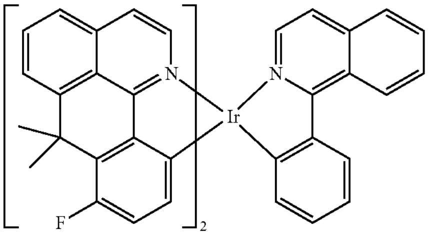
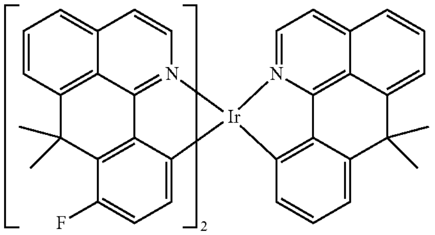
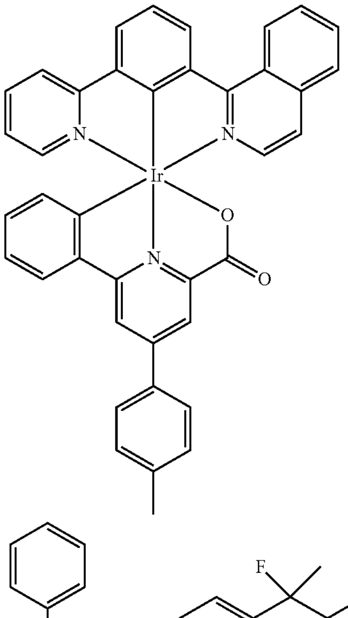
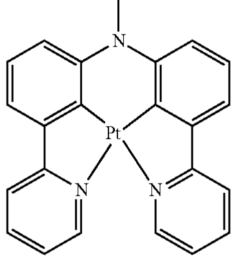
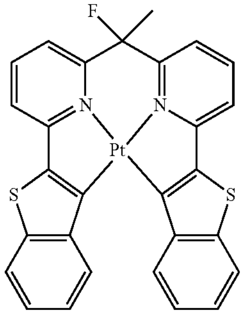

-continued
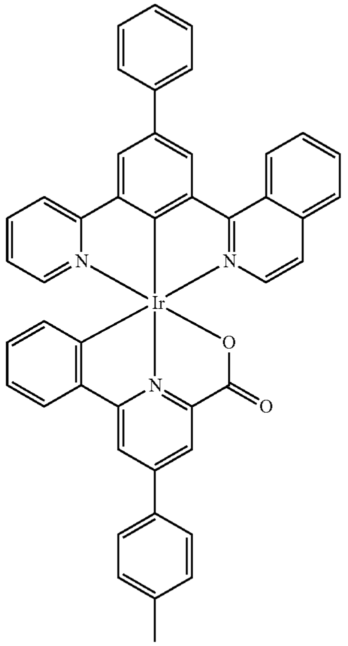
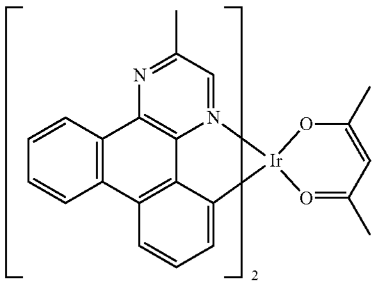
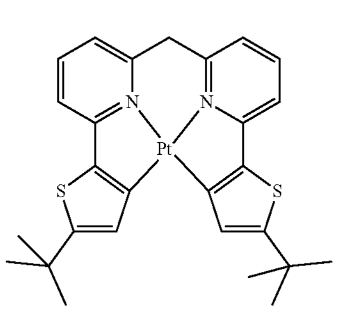
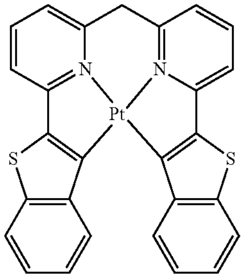
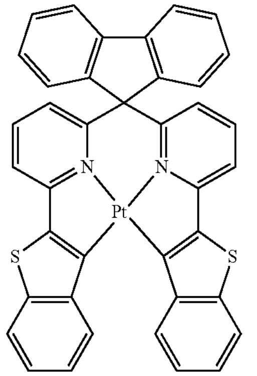
-continued
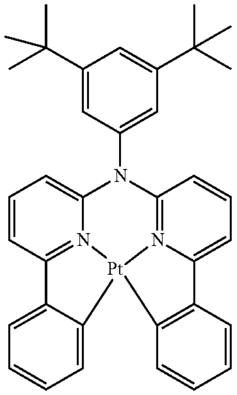
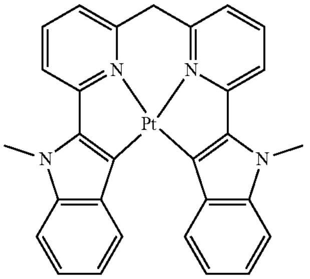
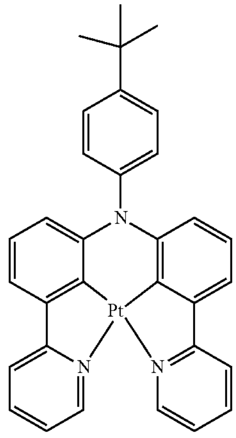
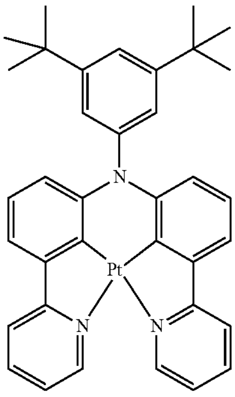
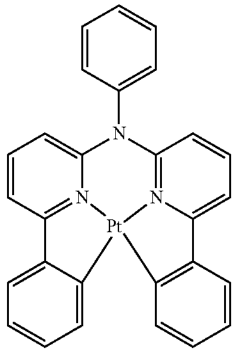
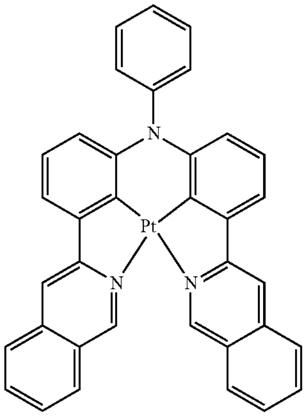
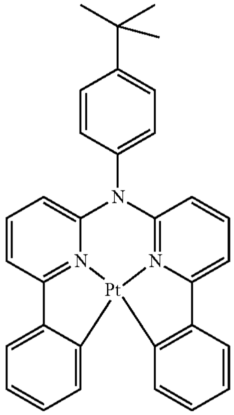
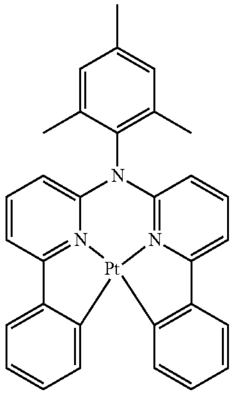

-continued
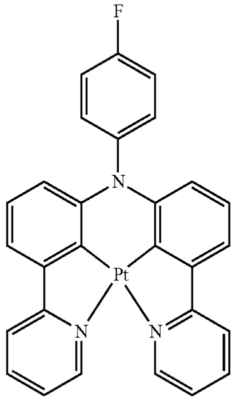
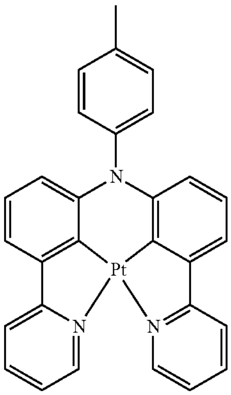
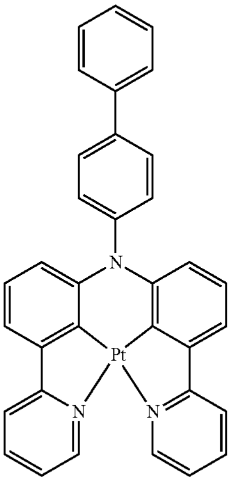
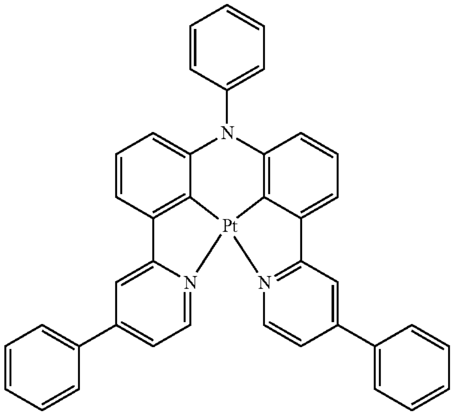
-continued
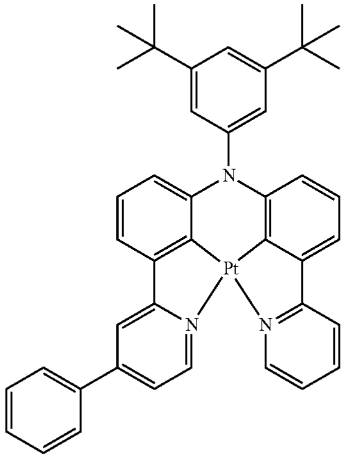
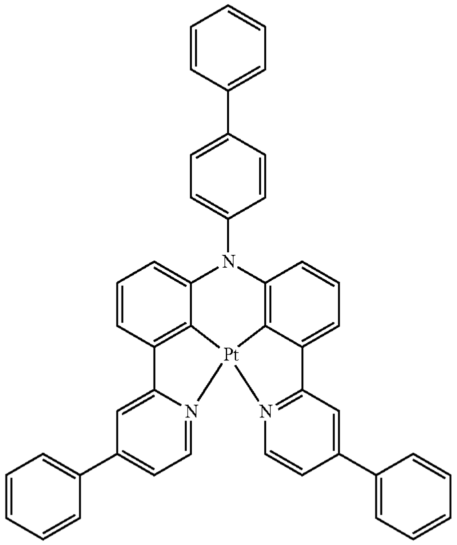
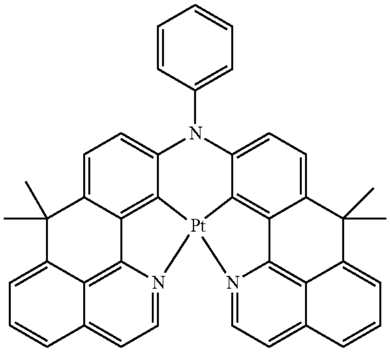

-continued
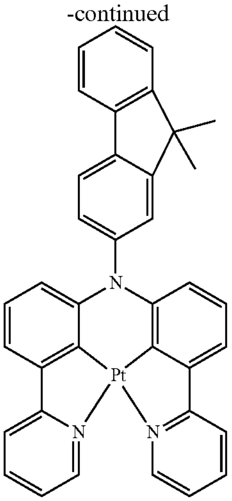
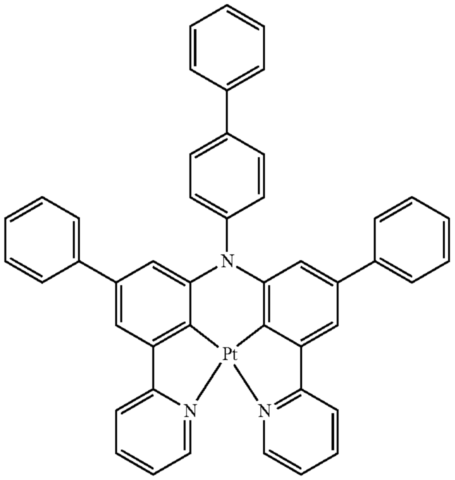
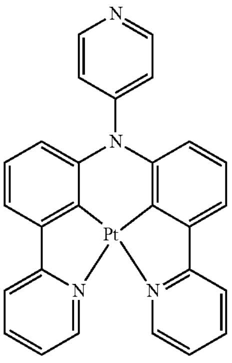
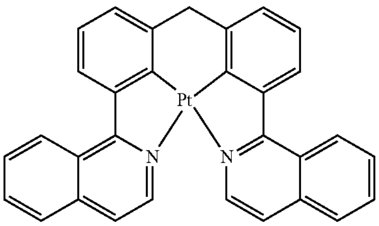
-continued
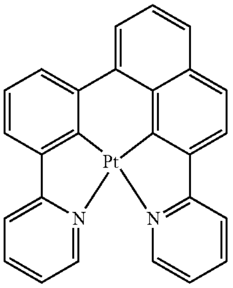
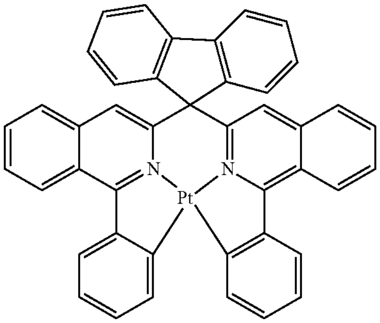
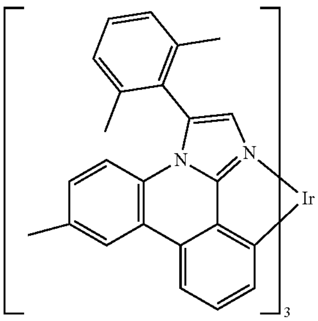
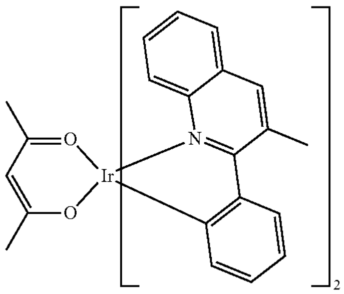
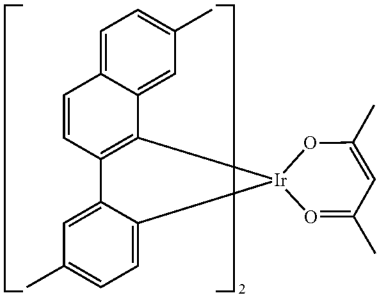

-continued
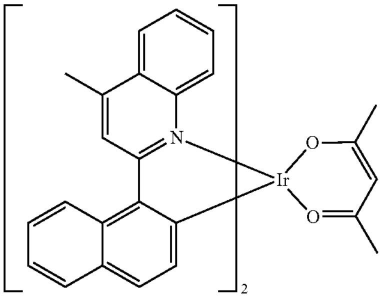
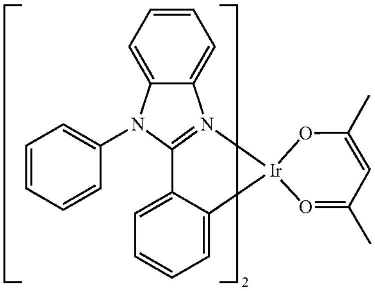
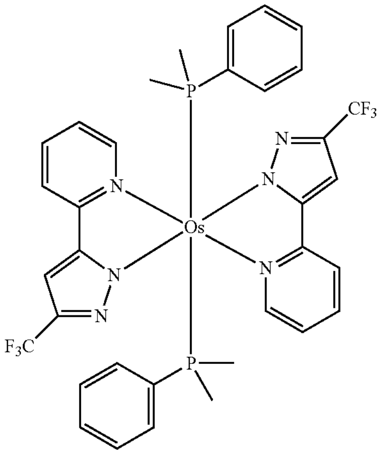
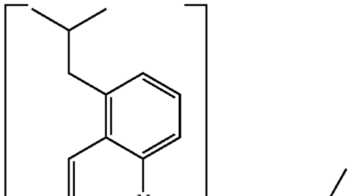
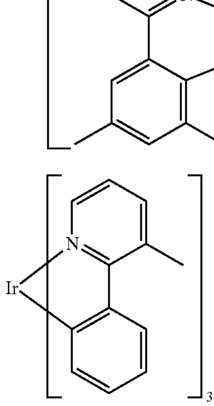
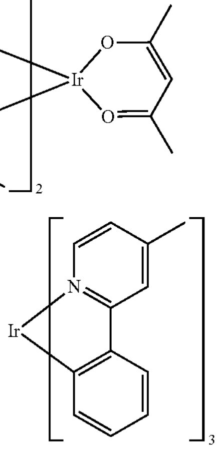
-continued
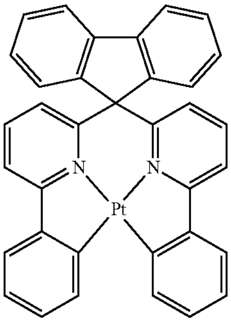
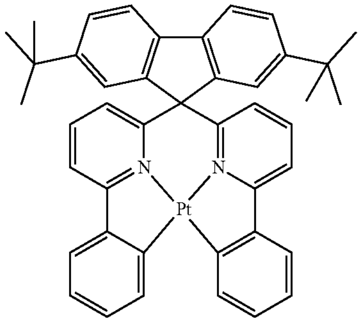
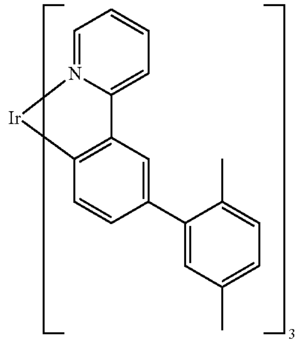
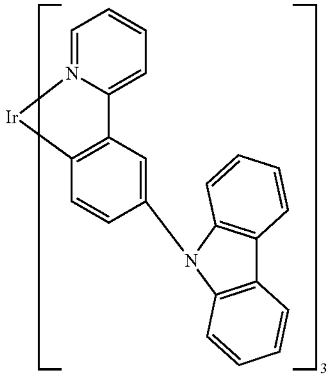
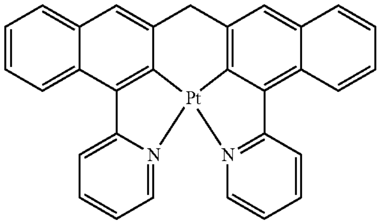

-continued
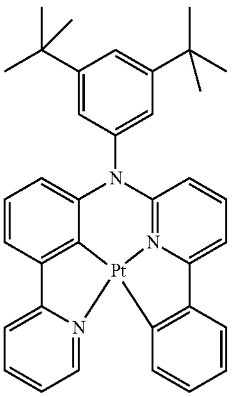
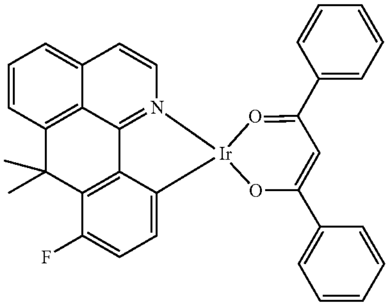
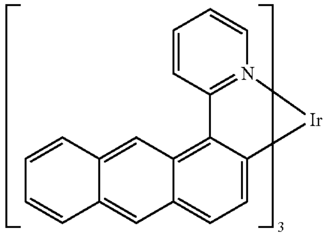
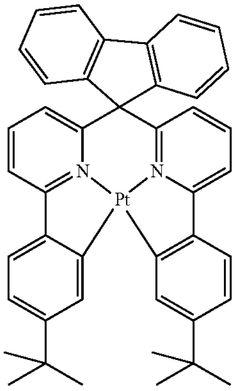
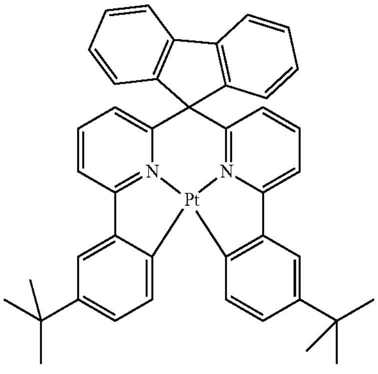
-continued
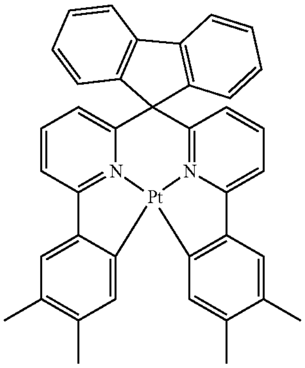
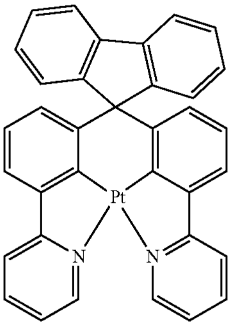
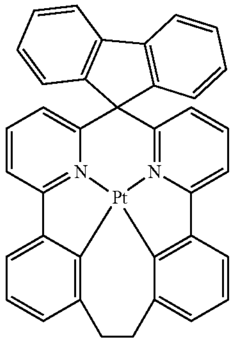
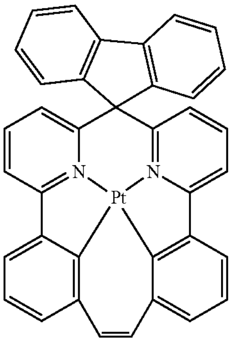
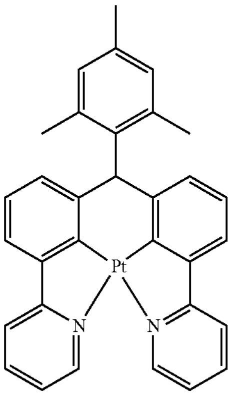
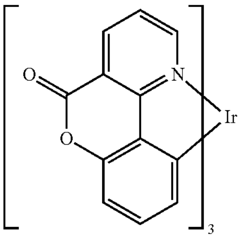
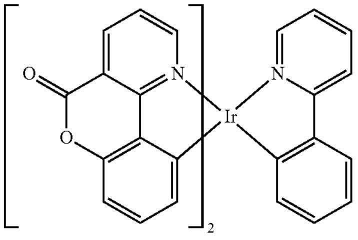

-continued
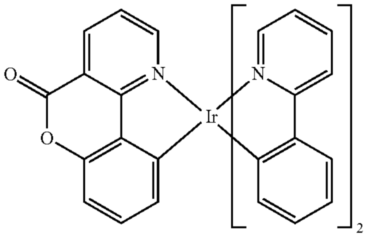
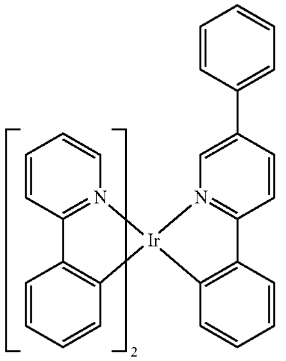
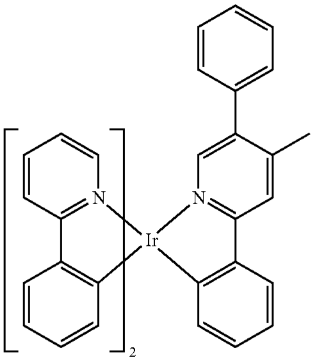
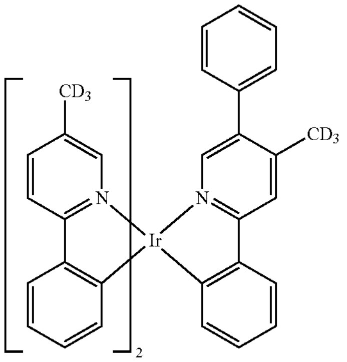
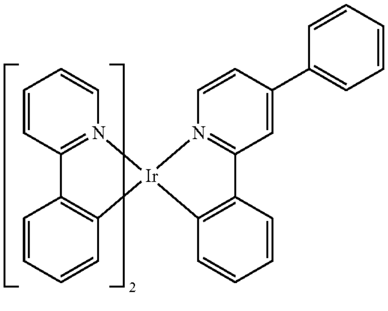
-continued
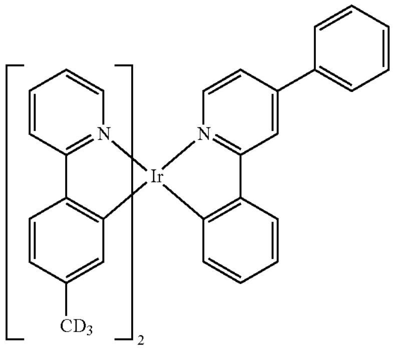
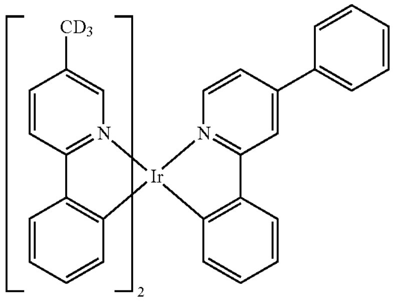
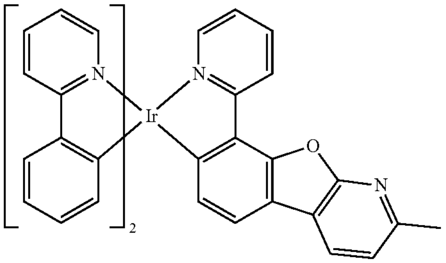
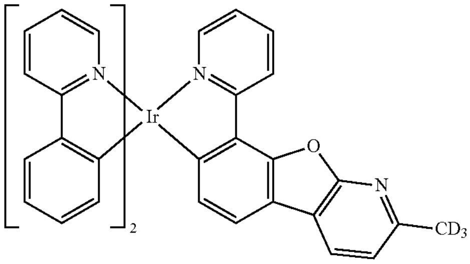
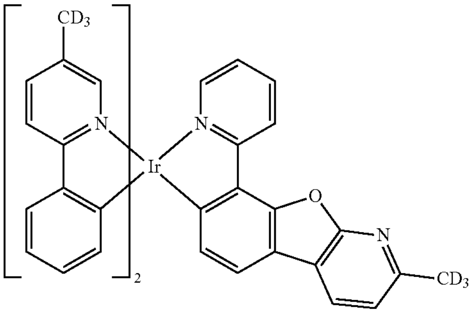

-continued
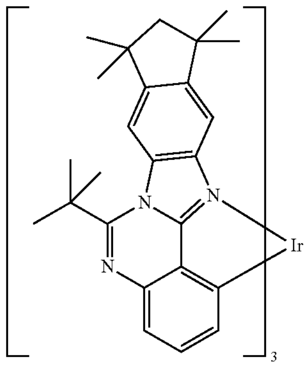
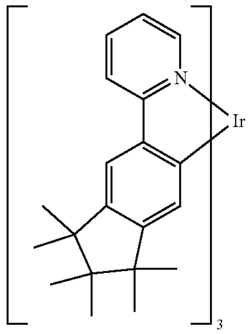
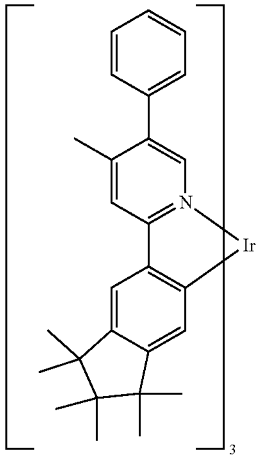
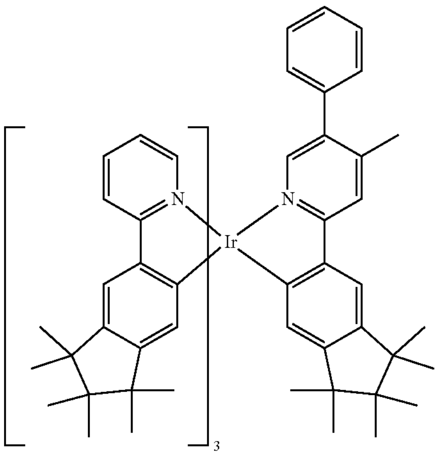
-continued
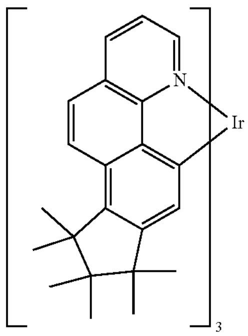
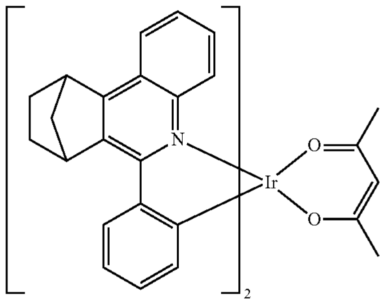
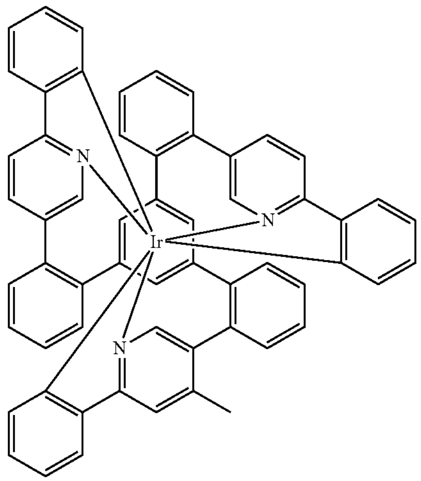
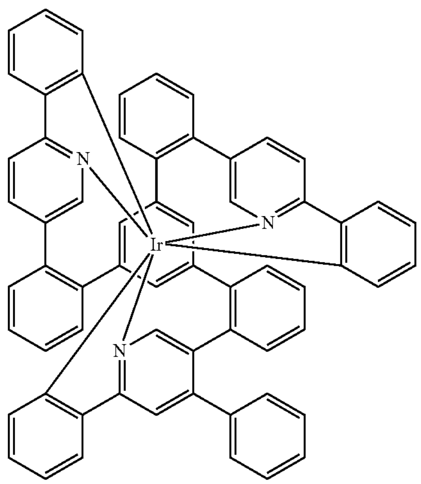

-continued
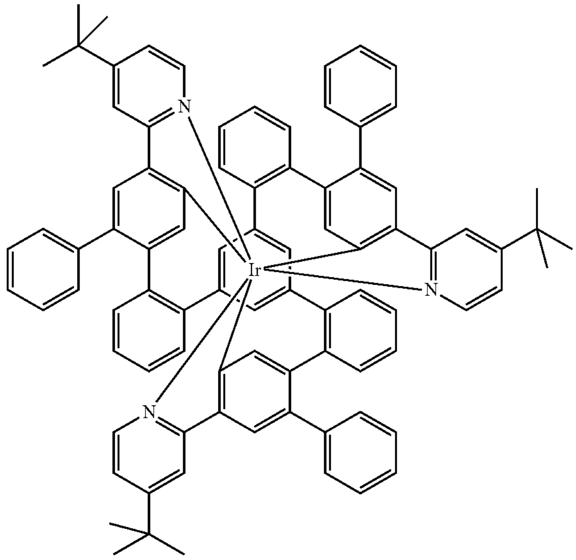
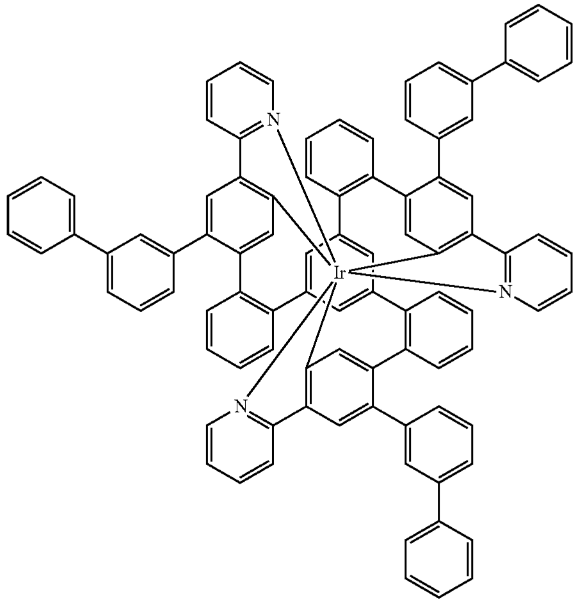
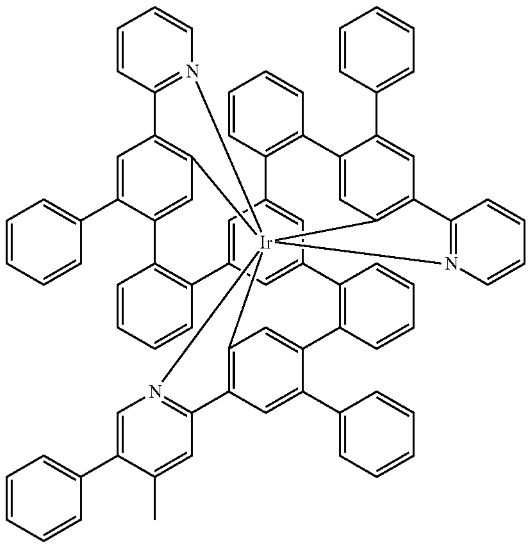
-continued
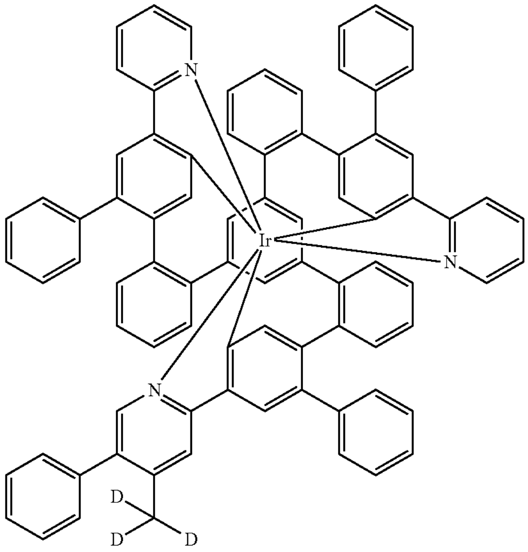
Further explicit examples of phosphorescent sensitizers are iridium and platinum complexes containing carbene ligands and the structures listed below, wherein homoleptic and heteroleptic complexes and meridonal and facial isomers may be suitable:
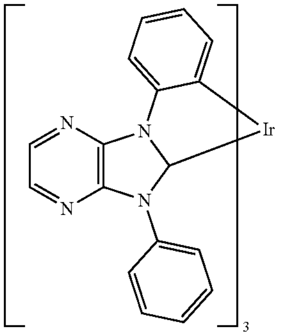
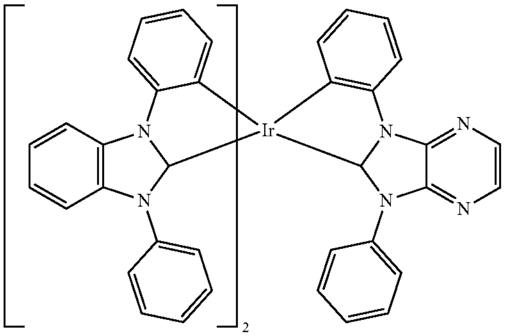

-continued
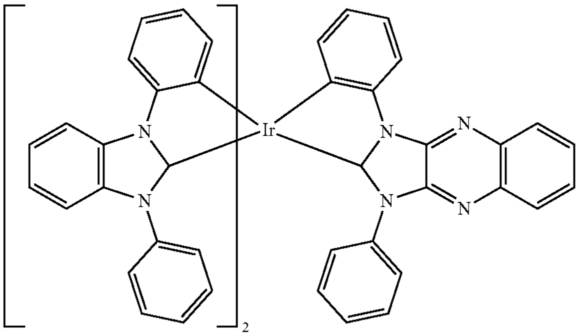
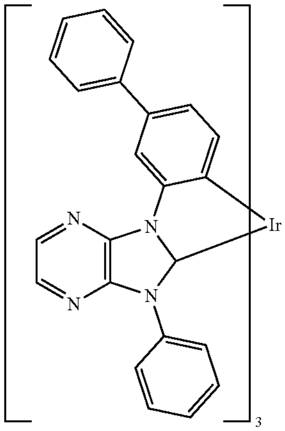
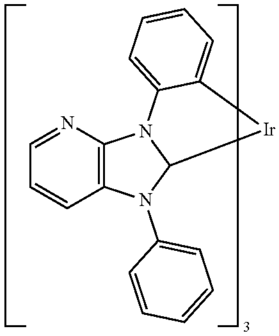
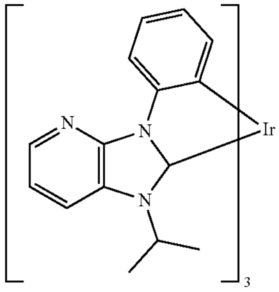
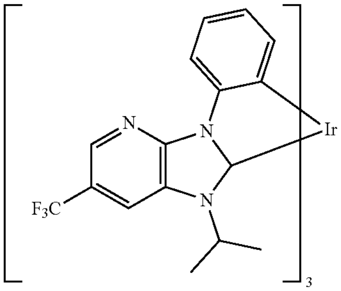
-continued
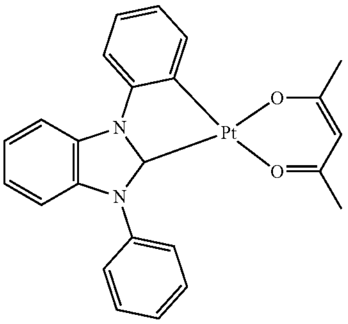
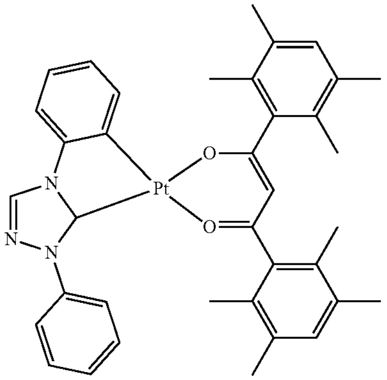
Further explicit examples of phosphorescent sensitizers are also copper complexes and the structures listed below:
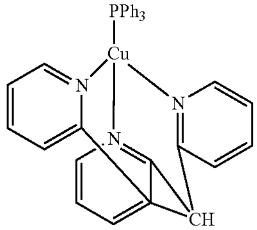
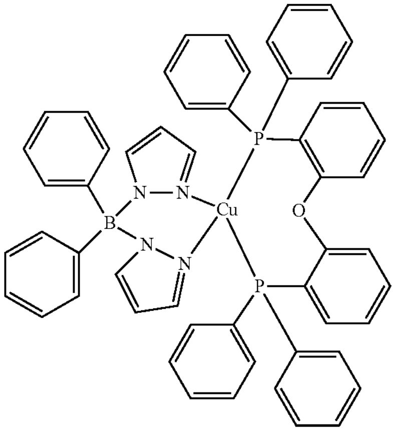

-continued

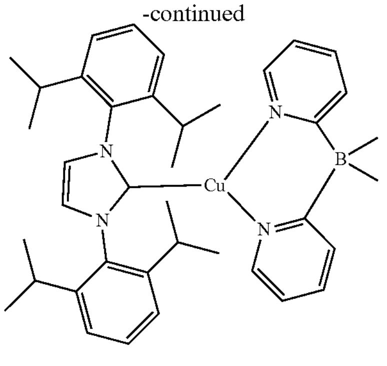

Besides the compounds according to the invention, suitable TADF compounds are compounds in which the energy gap between the lowest triplet state $T_1$ and the first excited singlet state $S_1$ is sufficiently small that the $S_1$ state is thermally accessible from the $T_1$ state. Preferably, TADF compounds have a gap between the lowest triplet state $T_1$ and the first excited singlet state $S_1$ of ≤0.30 eV. More preferably, the gap between $S_1$ and $T_1$ is ≤0.20 eV, even more preferably ≤0.15 eV, especially more preferably ≤0.10 eV and even more especially preferably ≤0.08 eV.

The energy of the lowest excited singlet state ($S_1$) and the lowest triplet state ($T_1$) as well as the HOMO and LUMO values are determined by quantum-chemical calculations. The Gaussian09 program package (revision D or later) is used. Neutral ground state geometries of all purely organic molecules are optimized at the AM1 level of theory. Subsequently, B3 PW91/6-31G(d) single point calculations including a calculation of the lowest singlet and triplet excited states with TD-B3 PW91/6-31G(d). HOMO and LUMO values as well as S1 and T1 excitation energies are taken from this single-point calculation at the B3 PW91/6-31G(d) level of theory.

Similarly, for metalorganic compounds, neutral ground state geometries are optimized at the HF/LANL2 MB level of theory. B3 PW91/6-31G(d)+LANL2DZ (LANL2DZ for all metal atoms, 6-31G(d) for all low-weight elements) is subsequently employed to calculate HOMO and LUMO values as well as TD-DFT excitation energies.

HOMO (HEh) and LUMO (LEh) values from the calculation are given in Hartree units. The HOMO and LUMO energy levels calibrated with reference to cyclic voltammetry measurements are determined therefrom in electron volts as follows:

$$\mathrm{HOMO}(eV)=((HEh*27.212)-0.9899)/1.1206$$

$$\mathrm{LUMO}(eV)=((LEh*27.212)-2.0041)/1.385$$

These values are to be regarded in the sense of the present invention as HOMO and LUMO energy levels of the materials.

The lowest triplet state $T_1$ is defined as the energy of the lowest TD-DFT triplet excitation energy.

The lowest excited singlet state $S_1$ is defined as the energy of the lowest TD-DFT singlet excitation energy.

Preferably, the TADF compound is an organic compound. Organic compounds in the context of the present invention are carbonaceous compounds that do not contain any metals. More particularly, organic compounds are formed from the elements C, H, D, B, Si, N, P, O, S, F, Cl, Br and I.

The TADF compound is more preferably an aromatic compound having both donor and acceptor substituents, with only slight spatial overlap between the LUMO and the HOMO of the compound. What is understood by donor and acceptor substituents is known in principle to those skilled in the art. Suitable donor substituents are especially diaryl- or -heteroarylamino groups and carbazole groups or carbazole derivatives, each preferably bonded to the aromatic compound via N. These groups may also have further substitution. Suitable acceptor substituents are especially cyano groups, but also, for example, electron-deficient heteroaryl groups which may also have further substitution, for example substituted or unsubstituted triazine groups.

The preferred dopant concentrations of the TADF compound in the emitting layer are described hereinafter. Because of the difference in production of the organic electroluminescent device, the dopant concentration in the case of production of the emitting layer by vapor deposition is reported in % by volume, and in the case of production of the emitting layer from solution in % by weight. The dopant concentrations in % by volume and % by weight is generally very similar.

In a preferred embodiment of the invention, in the case of production of the emitting layer by vapor deposition, the TADF compound is present in a dopant concentration of 1% to 70% by volume in the emitting layer, more preferably of 5% to 50% by volume, even more preferably of 5% to 30% by volume.

In a preferred embodiment of the invention, in the case of production of the emitting layer from solution, the TADF compound is present in a dopant concentration of 1% to 70% by weight in the emitting layer, more preferably of 5% to 50% by weight, even more preferably of 5% to 30% by weight.

The general art knowledge of the person skilled in the art includes knowledge of which materials are generally suitable as TADF compounds. The following references disclose, by way of example, materials that are potentially suitable as TADF compounds:

Tanaka et al., Chemistry of Materials 25 (18), 3766 (2013).

Lee et al., Journal of Materials Chemistry C 1 (30), 4599 (2013).

Zhang et al., Nature Photonics advance online publication, 1 (2014), doi: 10.1038/nphoton.2014.12.

Serevicius et al., Physical Chemistry Chemical Physics 15 (38), 15850 (2013).

Li et al., Advanced Materials 25 (24), 3319 (2013).

Youn Lee et al., Applied Physics Letters 101 (9), 093306 (2012).

Nishimoto et al., Materials Horizons 1, 264 (2014), doi: 10.1039/C3MH00079F.

Valchanov et al., Organic Electronics, 14 (11), 2727 (2013).

Nasu et al., ChemComm, 49, 10385 (2013).

In addition, the following patent applications disclose potential TADF compounds: US2019058130, WO18155642, WO18117179A1, US2017047522, US2016372682A, US2015041784, US2014336379, US2014138669, WO 2013/154064, WO 2013/133359, WO 2013/161437, WO 2013/081088, WO 2013/081088, WO 2013/011954, JP 2013/116975 und US 2012/0241732.

In addition, the person skilled in the art is able to infer design principles for TADF compounds from these publications. For example, Valchanov et al. show how the colour of TADF compounds can be adjusted.

Examples of suitable molecules which exhibit TADF are the structures shown in the following table:

-continued
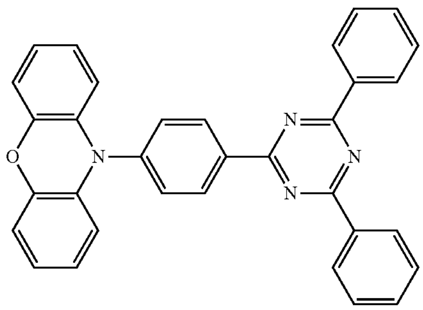
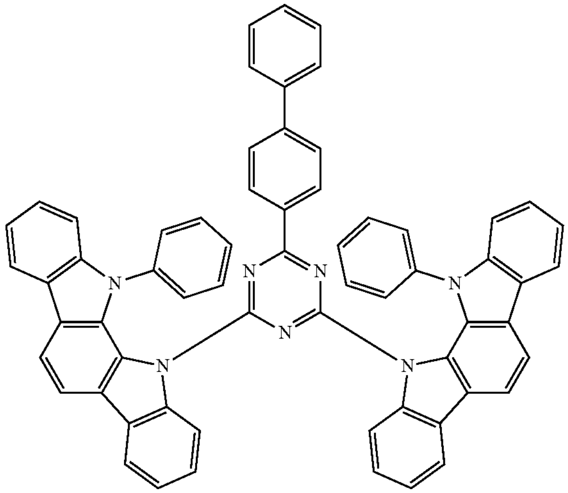
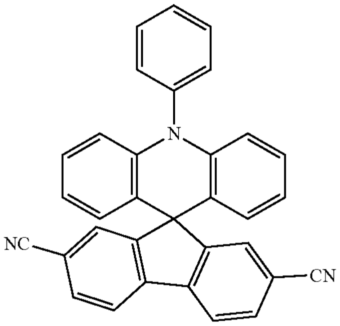
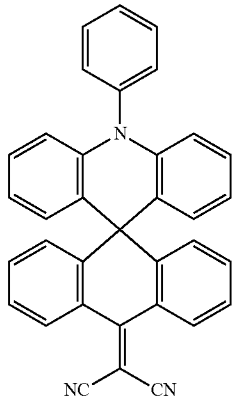
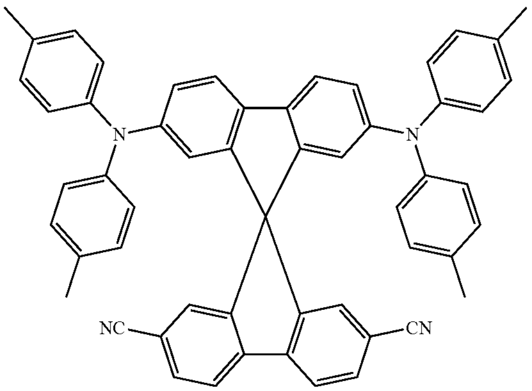
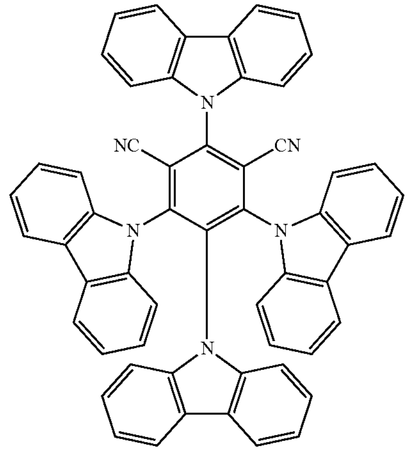
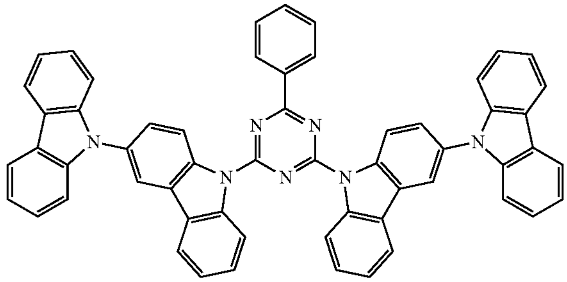

-continued
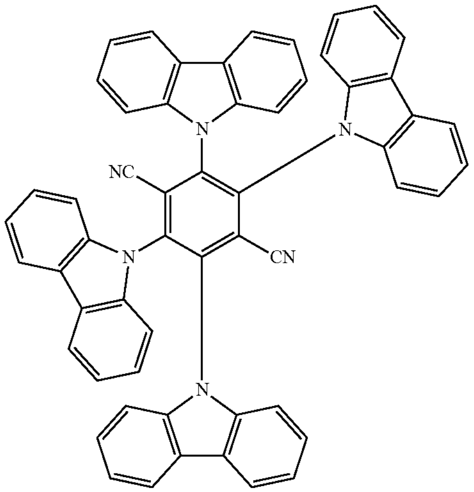
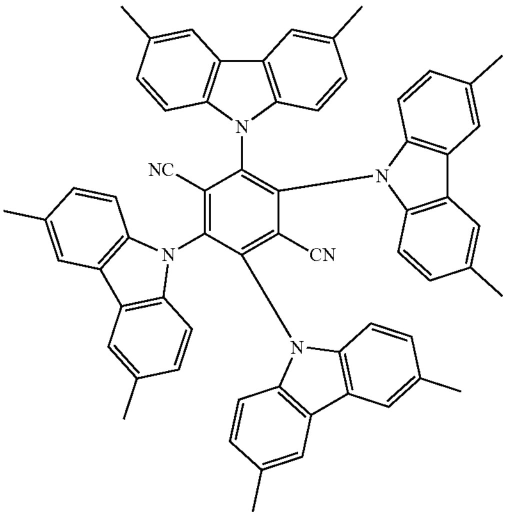
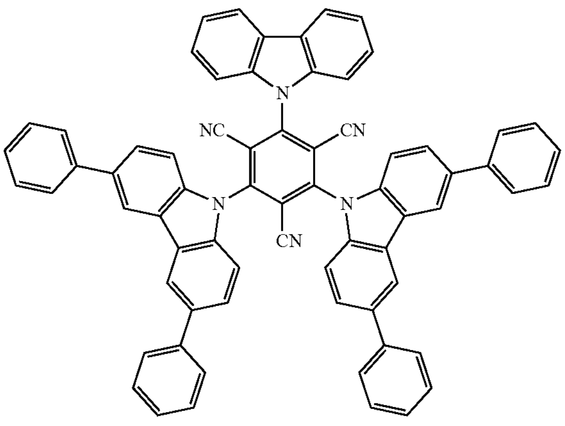
-continued
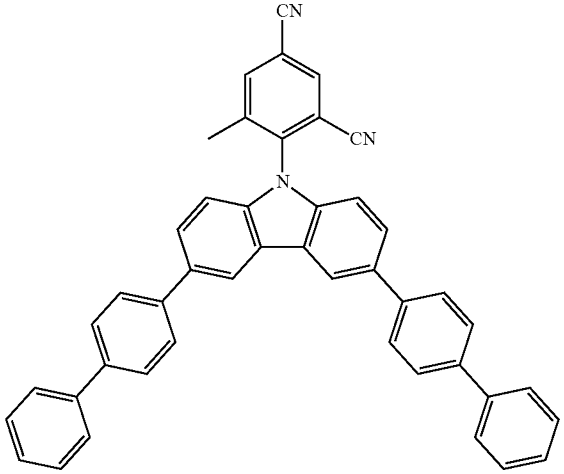
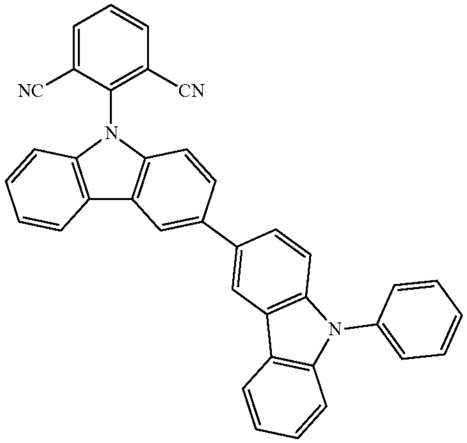
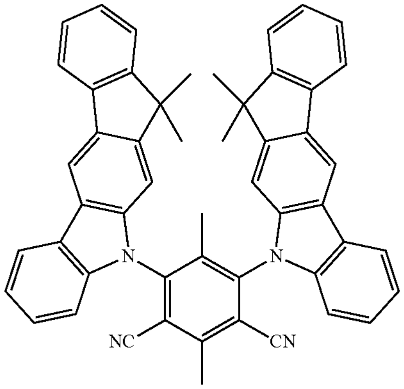
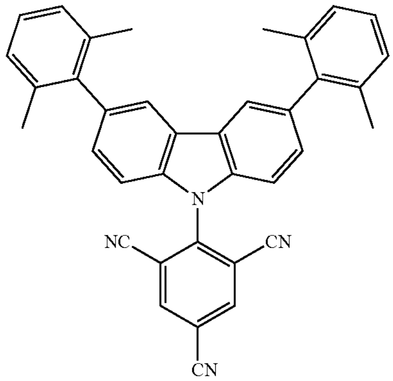

-continued
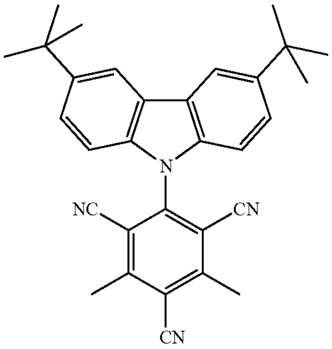
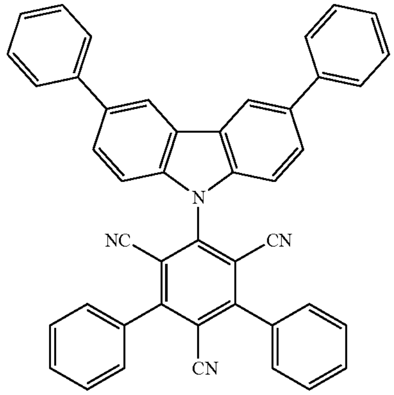
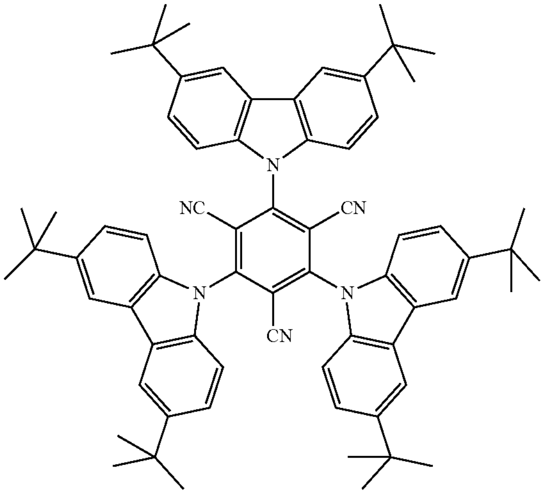
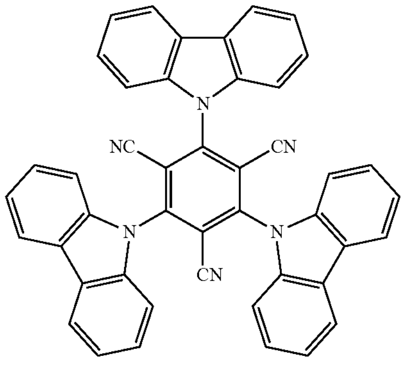
-continued
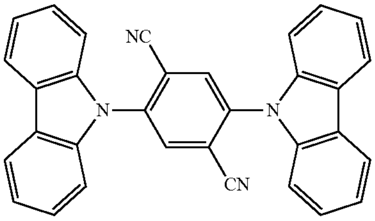
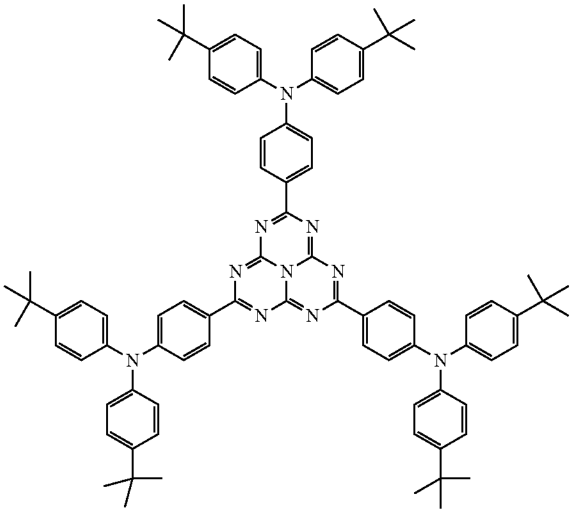
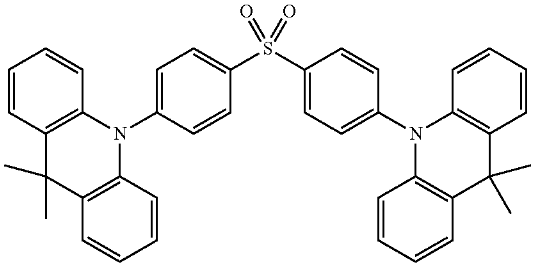
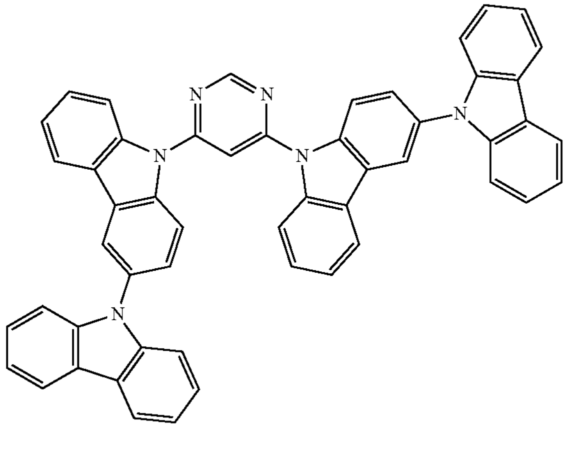

-continued

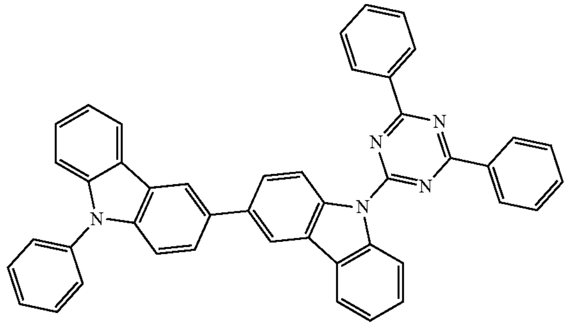

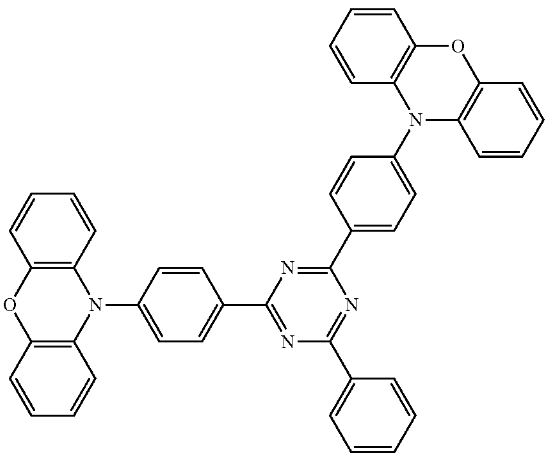

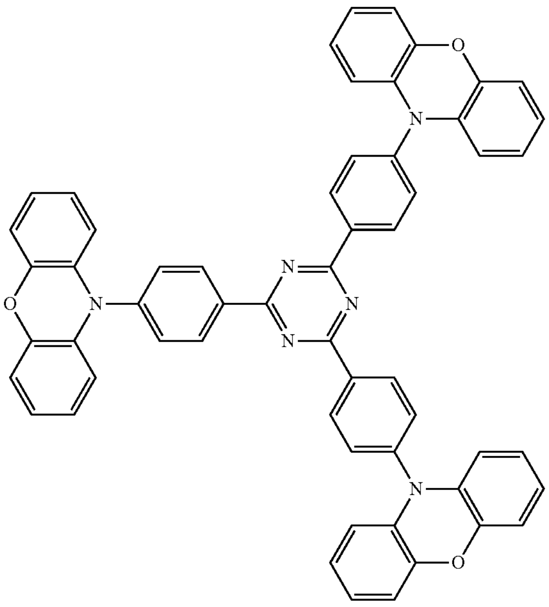

-continued

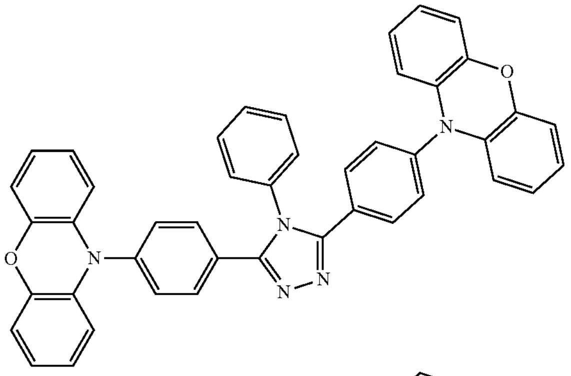

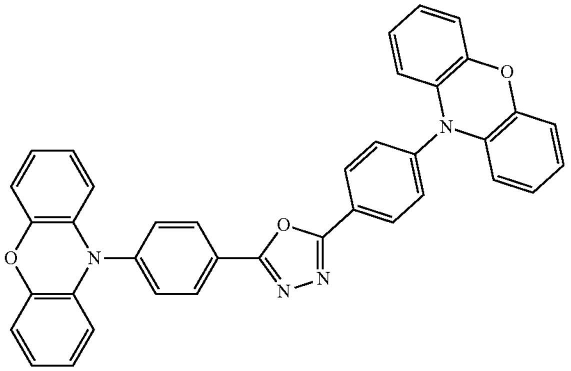

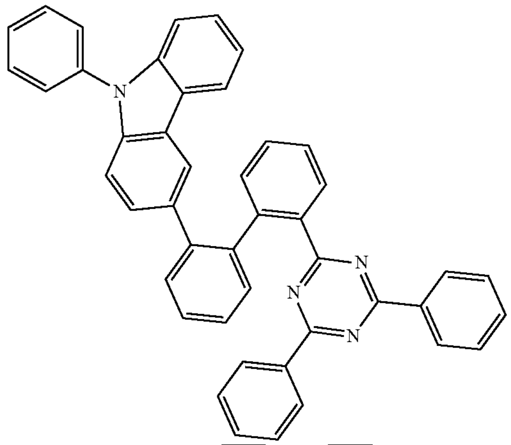

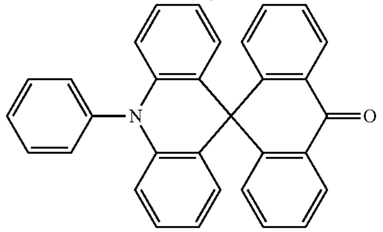

As mentioned above, the compounds of formula (1) or in accordance with the preferred embodiments may be used as fluorescent emitters in combination with a sensitizer in a hyperfluorescent or hyperphosphorescent system. In this case, it is preferred that the compounds of formula (1) are sterically shielded. Preferably, the emitting layer further comprises at least one organic functional material selected from matrix materials.

The compounds of formula (1) or in accordance with preferred embodiments can also be employed in combination with further compounds selected from the group consisting of HTM (Hole Transport Material), HIM (Hole Injection Material), HBM (Hole Blocking Material), p-dopant, ETM (Electron Transport Material), EIM (Electron Injection Material), EBM (Electron Blocking Material), n-dopant, fluorescent emitter, phosphorescent emitter, delayed fluorescent emitter, matrix material, host material, wide band gap material and quantum material, like quantum dot and quantum rod.

In accordance with still another preferred embodiment of the invention, the compound of formula (1) or in accordance with the preferred embodiments is employed as a matrix material for an emitter in the emitting layer, preferably as a matrix material for a phosphorescent emitter, wherein the phosphorescent emitters correspond to phosphorescent emitters as described above.

The compounds of formula (1) or in accordance with preferred embodiments can also be employed in other layers, for example as hole-transport materials in a hole-injection or hole-transport layer or electron-blocking layer or as matrix materials in an emitting layer.

Generally preferred classes of material for use as corresponding functional materials in the organic electroluminescent devices according to the invention are indicated below.

Suitable charge-transport materials, as can be used in the hole-injection or hole-transport layer or electron-blocking layer or in the electron-transport layer of the electronic device according to the invention, are, for example, the compounds disclosed in Y. Shirota et al., Chem. Rev. 2007, 107 (4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example LiQ, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives.

Furthermore, suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as applications EP 2875092, EP 2875699 and EP 2875004), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers).

Preferred anode materials here are conductive mixed metal oxides. Particular preference is given to indium tin oxide (ITO) or indium zinc oxide (IZO).

Preference is furthermore given to conductive, doped organic materials, in particular conductive doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

In accordance with the invention, the electronic devices comprising one or more compounds according to the invention can be employed in displays, as light sources in lighting applications and as light sources in medical and/or cosmetic applications (for example light therapy).

The invention will now be explained in greater detail by the following examples, without wishing to restrict it thereby.

A) Syntheses Examples

Unless otherwise stated, the following syntheses are carried out in a protective gas atmosphere in dried solvents. The solvents and reagents can be obtained from Sigma-ALDRICH or ABCR. The CAS numbers of the compounds known from the literature are also indicated below. The compounds according to the invention can be synthesised by means of synthesis methods known to the skilled person.

a)3-bromo-2-chloro-N,N-diphenyl-aniline

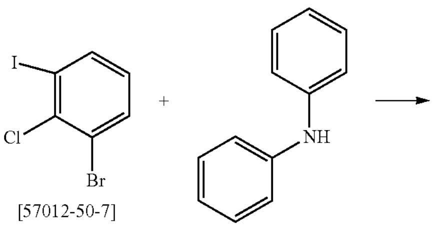

[57012-50-7]

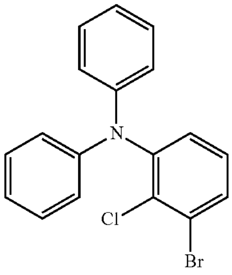

11 g (35 mmol, 1 eq) of N-phenylaniline together with 6 g (35 mmol, 1 eq) of 1-bromo-2-chloro-3-iodobenzene and 10 g (112 mmol, 3 eq) of sodium t-butoxide in 150 ml of absolute toluene are added in a 2 L four-necked flask and degassed for 30 minutes. Then, 310 mg (1.3 mmol, 0.04 eq) of palladium(II) acetate and 1.5 g (2.7 mmol, 0.08 eq) of DPPF are added and the preparation is heated overnight under reflux. When the reaction is complete, the preparation is cooled down to room temperature and extracted with 500 ml water. The aqueous phase is then washed three times with toluene, the combined organic phases are dried over sodium sulphate and the solvent is removed on the rotary evaporator. The brown residue is absorbed in approx. 200 ml toluene and filtered via silica gel. For further purification a recrystallisation from toluene/heptane is carried out.

The yield is 11.3 g (31.5 mmol), corresponding to 89% of the theory.

b) 5-[2-chloro-3-(N-phenylanilino)phenyl]phenanthridin-6-one

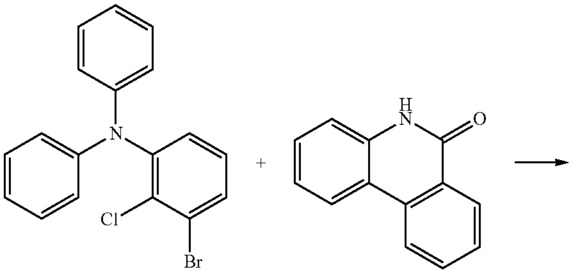

[1015-89-0]

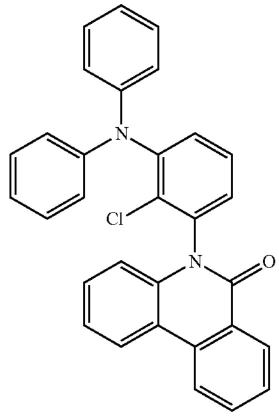

9.76 g (50 mmol, 1.00 eq.) of 6-phenanthridinone, 25 g (70 mmol, 1.4 eq.) of 3-bromo-2-chloro-N,N-diphenyl-aniline and 14.4 g of potassium carbonate (104 mmol, 2.10 eq.) are placed in 420 ml dry DMF and degassed with argon. Then 1.24 g (5.4 mmol, 0.11 eq) of 1,3-di(2-pyridyl)-1,3-propanedione and 1.02 g (5.4 mmol, 0.11 eq) of copper(I) iodide are added and the mixture is heated at 140° C. for three days. When the reaction is complete, the mixture is carefully concentrated on the rotary evaporator, the precipitated solid is removed by suction and washed with water and ethanol. The raw product is purified twice using a hot extractor (toluene/heptane 1:1) and the resulting solid is recrystallised from a toluene.

The yield is 12.8 g (27 mmol), corresponding to 50% of the theoretical yield.

The following compounds can be obtained analogously:
| | Educt 1 | Educt 2 | Product | Yield |
|---|---|---|---|---|
| 1b | 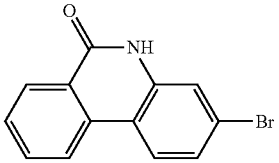<br>[500350-01-6] | 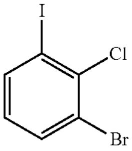<br>[57012-50-7] | 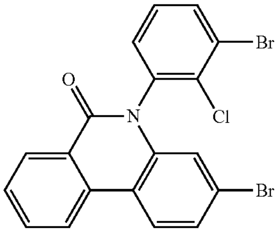 [SMILES: O=c1c2ccccc2c2ccc(Br)cc2n1-c1cccc(Br)c1Cl] | 41% |
| 2b | 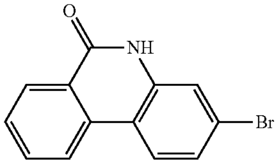<br>[500350-01-6] | 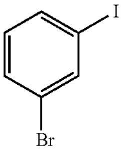 | 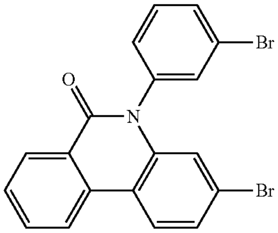 [SMILES: O=c1c2ccccc2c2ccc(Br)cc2n1-c1cccc(Br)c1] | 58% |
| 3b | 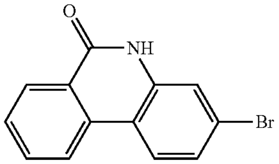<br>[500350-01-6] | 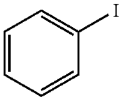 | 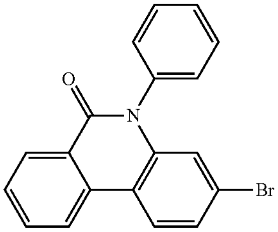 [SMILES: O=c1c2ccccc2c2ccc(Br)cc2n1-c1ccccc1] | 67% |
| 4b | 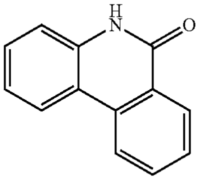<br>[1015-89-0] | 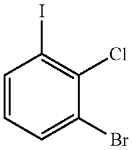<br>[57012-50-7] | 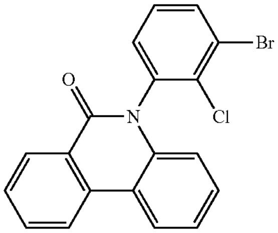 [SMILES: O=c1c2ccccc2c2ccccc2n1-c1cccc(Br)c1Cl] | 58% |
| 5b | 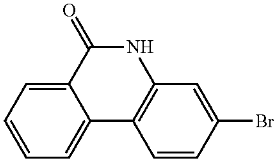<br>[500350-01-6] | 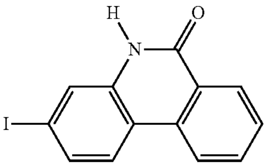<br>[500554-14-3] | 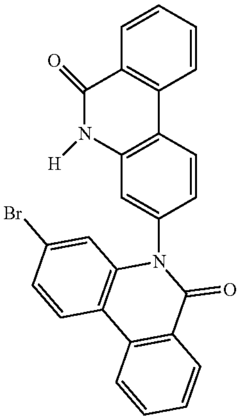 [SMILES: O=c1[nH]c2cc(-n3c(=O)c4ccccc4c4ccc(Br)cc43)ccc2c2ccccc12] | 59% |

-continued
| | Educt 1 | Educt 2 | Product | Yield |
|---|---|---|---|---|
| 6b | 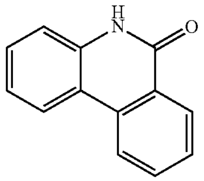 [1015-89-0] | 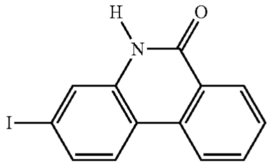 [500554-14-3] | 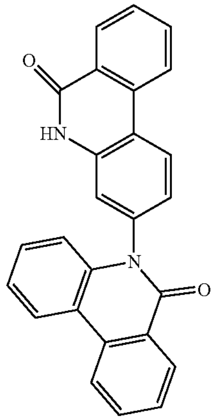 [SMILES: O=c1[nH]c2cc(-n3c(=O)c4ccccc4c4ccccc43)ccc2c2ccccc12] | 61% |
| 7b | 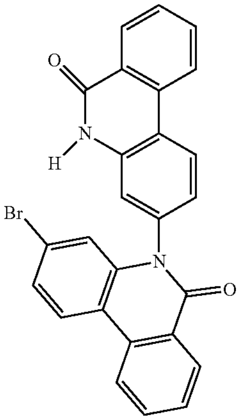 [SMILES: O=c1[nH]c2cc(-n3c(=O)c4ccccc4c4ccc(Br)cc43)ccc2c2ccccc12] | 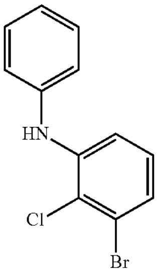 [2375361-69-4] | 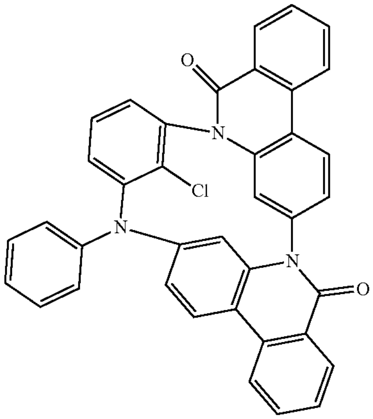 [SMILES: O=c1c2ccccc2c2ccc3cc2n1c1ccc2c4ccccc4c(=O)n(c4cccc(c4Cl)n3-c3ccccc3)c2c1] | 44% |
| 8b | 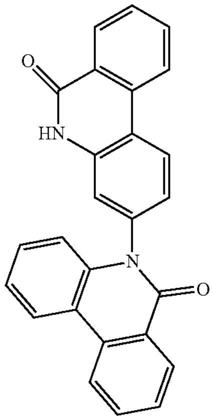 | 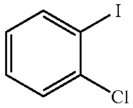 | 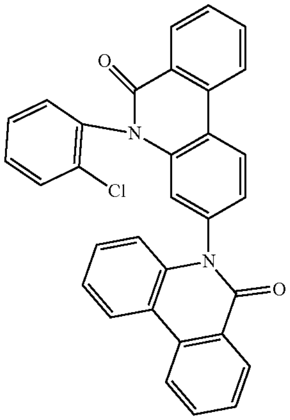 [SMILES: O=c1c2ccccc2c2ccccc2n1-c1ccc2c3ccccc3c(=O)n(-c3ccccc3Cl)c2c1] | 71% |
| 9b | 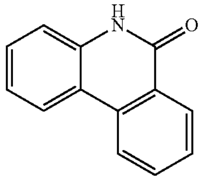 [1015-89-0] | 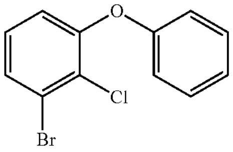 [1800321-81-6] | 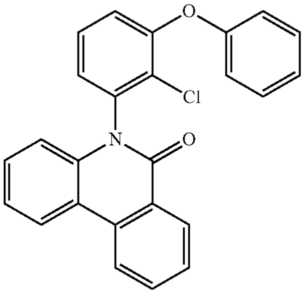 [SMILES: O=c1c2ccccc2c2ccccc2n1-c1cccc(Oc2ccccc2)c1Cl] | 67% |

c) Ring Formation

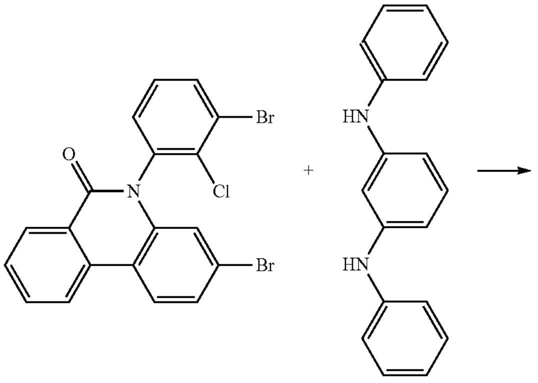

[5905-36-2]

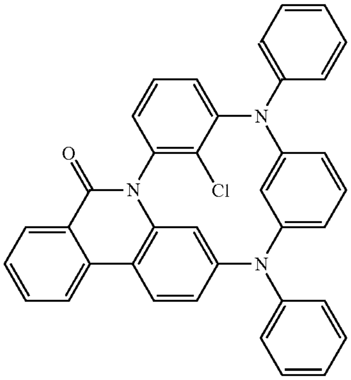

16.2 g (35 mmol, 1 eq) of m-phenylenediamine is mixed together with 9.1 g (35 mmol, 1 eq) of 3-bromo-5-(3-bromo-2-chloro-phenyl) phenanthridin-6-one and 10 g (111 mmol, 3 eq) of sodium t-butoxide in 150 ml absolute toluene and degassed for 30 minutes. Then, 310 mg (1.3 mmol, 0.04 eq) of palladium(II) acetate and 1.5 g (2.7 mmol, 0.08 eq) of DPPF are added and the preparation is heated overnight under reflux. When the reaction is complete, the preparation is cooled down to room temperature and extracted with 500 ml water. The aqueous phase is then washed three times with toluene, the combined organic phases are dried over sodium sulphate and the solvent is removed using the rotary evaporator. The brown residue is mixed with approx. 200 ml of toluene and filtered via silica gel. For further purification, a recrystallisation from toluene/heptane is carried out.

The yield is 13.7 g (24 mmol), corresponding to 70% of the theory.

The following connections can be obtained analogously:
| | Educt 1 | Educt 2 | Product | Yield |
|---|---|---|---|---|
| 1c | 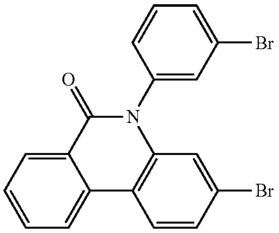 [SMILES: O=c1c2ccccc2c2ccc(Br)cc2n1-c1cccc(Br)c1] | 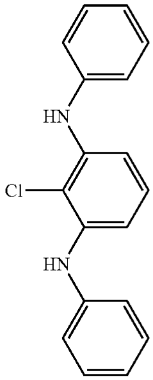 [2093315-64-9] | 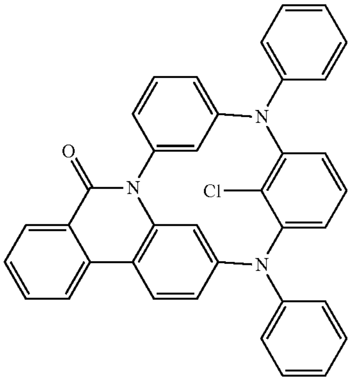 [SMILES: O=c1c2ccccc2c2ccc3cc2n1c1cccc(c1)n(-c1ccccc1)c1cccc(c1Cl)n3-c1ccccc1] | 57% |
| 2c | 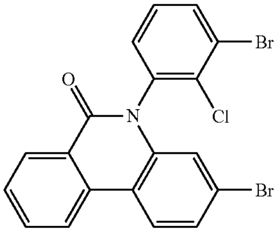 [SMILES: O=c1c2ccccc2c2ccc(Br)cc2n1-c1cccc(Br)c1Cl] | 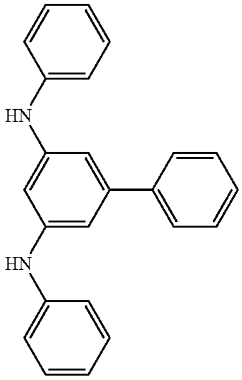 [2241082-93-7] | 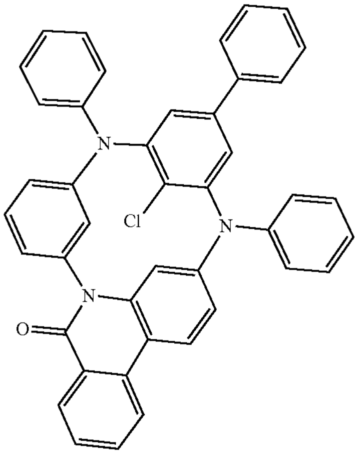 [SMILES: O=c1c2ccccc2c2ccc3cc2n1c1cccc(c1)n(-c1ccccc1)c1cc(-c2ccccc2)cc(c1Cl)n3-c1ccccc1] | 60% |
| 3c | 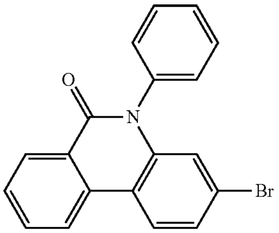 [SMILES: O=c1c2ccccc2c2ccc(Br)cc2n1-c1ccccc1] | 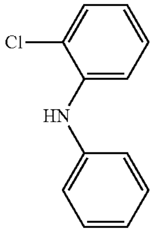 [1205-40-9] | 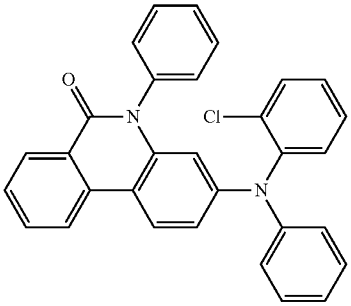 [SMILES: O=c1c2ccccc2c2ccc(N(c3ccccc3)c3ccccc3Cl)cc2n1-c1ccccc1] | 57% |
| 4c | 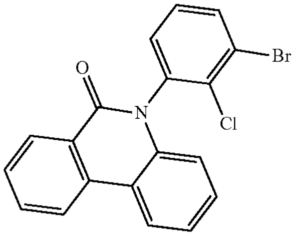 [SMILES: O=c1c2ccccc2c2ccccc2n1-c1cccc(Br)c1Cl] | 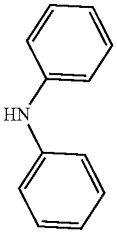 [SMILES: c1ccc(Nc2ccccc2)cc1] | 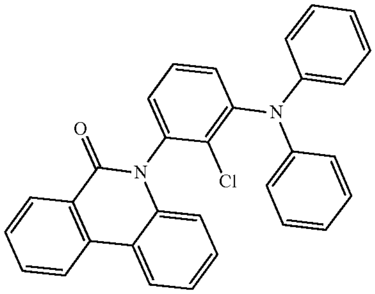 [SMILES: O=c1c2ccccc2c2ccccc2n1-c1cccc(N(c2ccccc2)c2ccccc2)c1Cl] | 67% |

d) Borylation

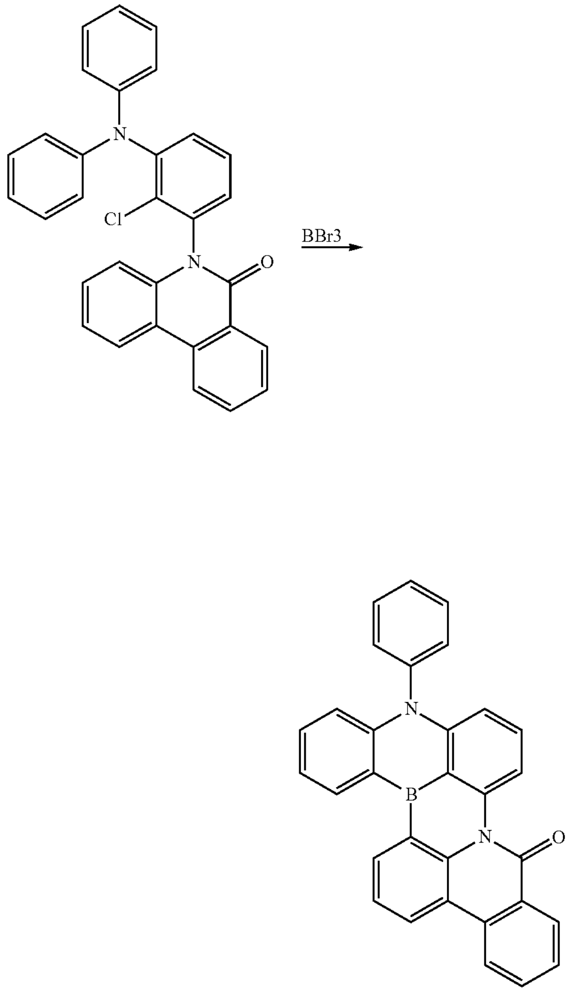

A solution of 32 ml (1.70 M, 54 mmol) of tert-butyllithium in pentane is slowly added to a solution of 21.2 g (45 mmol) of 5-[2-chloro-3-(N-phenylanilino)phenyl] phenanthridin-6-one in 150 ml of tert-butylbenzene at −30° C. under a nitrogen atmosphere. After 2 h stirring at 60° C., the pentane is removed under vacuum. After addition of 5.1 ml (53.9 mmol) of boron tribromide at −30° C., the reaction mixture is stirred at room temperature for 0.5 h, then 15.6 ml (91.1 mmol) of N-diisopropylethylamine is added at 0° C., and then the reaction mixture is warmed to room temperature. After 3 h stirring at 120° C., the reaction mixture is cooled down to room temperature. An aqueous solution of 13.0 g of sodium acetate in 100 ml of water and 50 ml of ethyl acetate is added to the reaction mixture. The aqueous layer is separated and extracted with 100 ml of ethyl acetate. The combined organic layer is condensed in vacuum.

The residue is dissolved in toluene and filtered with a silica gel pad (eluent: toluene). The solvent is removed under vacuum.

The residue is recrystallized from toluene/heptane and finally purified by sublimation.

The yield is 8.2 g (18.5 mmol), corresponding to 41% of the theory. Purity according to 1H NMR approx. 99.9%.

The following compounds can be obtained analogously:
| | Educt | Product | Yield |
|---|---|---|---|
| 1d | 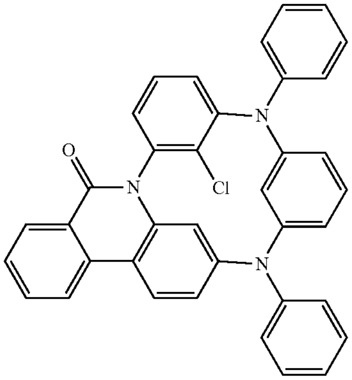 [SMILES: O=c1c2ccccc2c2ccc3cc2n1c1cccc(c1Cl)n(-c1ccccc1)c1cccc(c1)n3-c1ccccc1] | 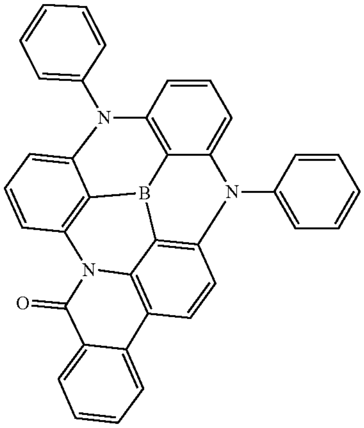 [SMILES: O=c1c2ccccc2c2ccc3c4c2n1-c1cccc2c1B4c1c(cccc1N3c1ccccc1)N2c1ccccc1] | 43% |
| 2d | 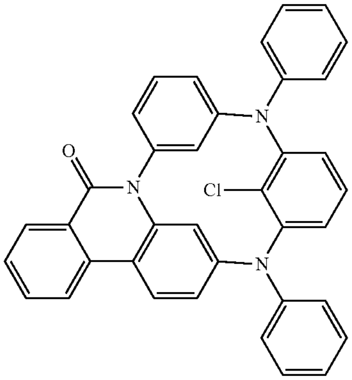 [SMILES: O=c1c2ccccc2c2ccc3cc2n1c1cccc(c1)n(-c1ccccc1)c1cccc(c1Cl)n3-c1ccccc1] | 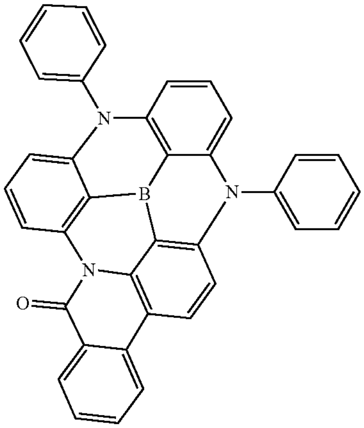 [SMILES: O=c1c2ccccc2c2ccc3c4c2n1-c1cccc2c1B4c1c(cccc1N3c1ccccc1)N2c1ccccc1] | 51% |
| 3d | 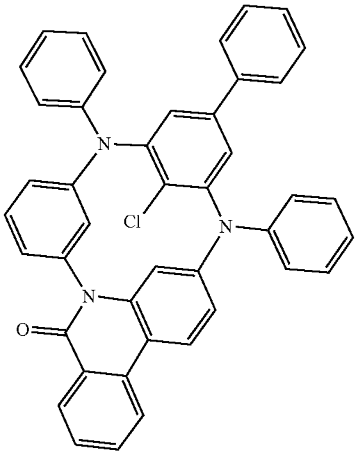 [SMILES: O=c1c2ccccc2c2ccc3cc2n1c1cccc(c1)n(-c1ccccc1)c1cc(-c2ccccc2)cc(c1Cl)n3-c1ccccc1] | 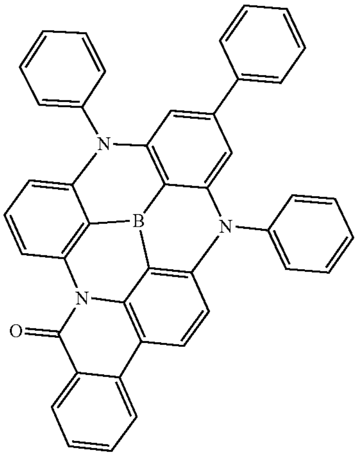 [SMILES: O=c1c2ccccc2c2ccc3c4c2n1-c1cccc2c1B4c1c(cc(-c4ccccc4)cc1N3c1ccccc1)N2c1ccccc1] | 40% |

-continued
| | Educt | Product | Yield |
|---|---|---|---|
| 4d | 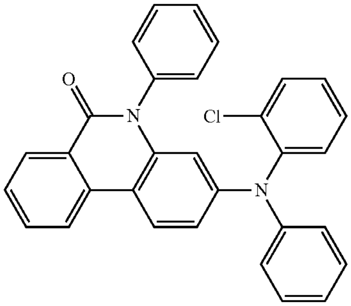 [SMILES: O=c1c2ccccc2c2ccc(N(c3ccccc3)c3ccccc3Cl)cc2n1-c1ccccc1] | 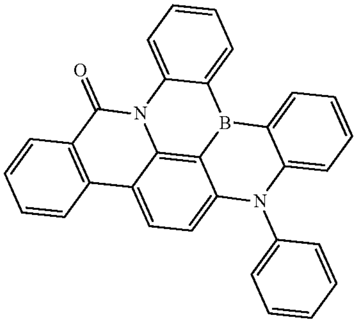 [SMILES: O=c1c2ccccc2c2ccc3c4c2n1-c1ccccc1B4c1ccccc1N3c1ccccc1] | 45% |
| 5d | 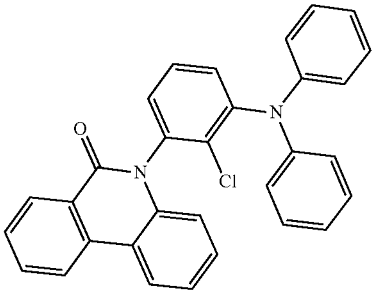 [SMILES: O=c1c2ccccc2c2ccccc2n1-c1cccc(N(c2ccccc2)c2ccccc2)c1Cl] | 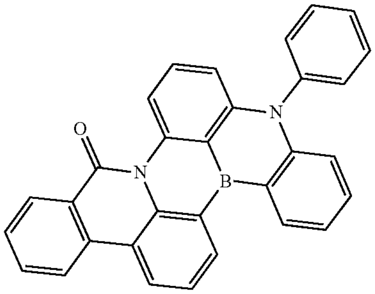 [SMILES: O=c1c2ccccc2c2cccc3c2n1-c1cccc2c1B3c1ccccc1N2c1ccccc1] | 47% |
| 6d | 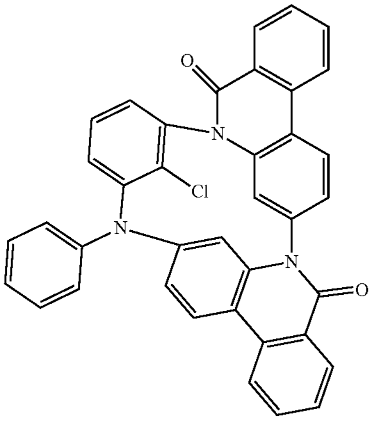 [SMILES: O=c1c2ccccc2c2ccc3cc2n1c1ccc2c4ccccc4c(=O)n(c4cccc(c4Cl)n3-c3ccccc3)c2c1] | 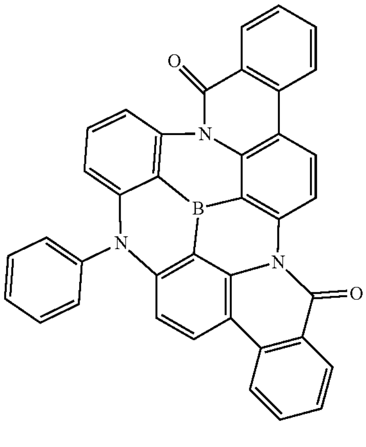 [SMILES: O=c1c2ccccc2c2ccc3c4c2n1-c1ccc2c5ccccc5c(=O)n5c2c1B4c1c(cccc1-5)N3c1ccccc1] | 42% |
| 7d | 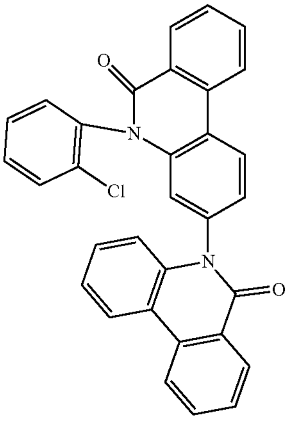 [SMILES: O=c1c2ccccc2c2ccccc2n1-c1ccc2c3ccccc3c(=O)n(-c3ccccc3Cl)c2c1] | 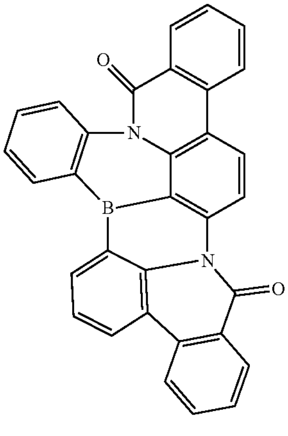 [SMILES: O=c1c2ccccc2c2cccc3c2n1-c1ccc2c4ccccc4c(=O)n4c2c1B3c1ccccc1-4] | 45% |

-continued

| | Educt | Product | Yield |
|---|---|---|---|
| 8d | 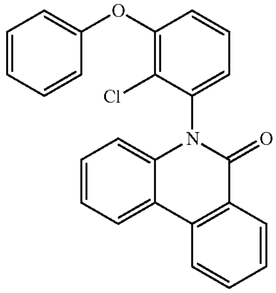 [SMILES: O=c1c2ccccc2c2ccccc2n1-c1cccc(Oc2ccccc2)c1Cl] | 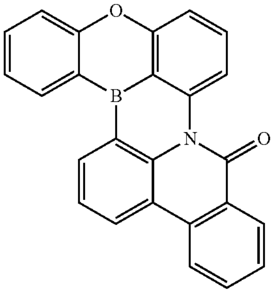 [SMILES: O=c1c2ccccc2c2cccc3c2n1-c1cccc2c1B3c1ccccc1O2] | 28% |

e) Reaction with Benzoyl Chloride

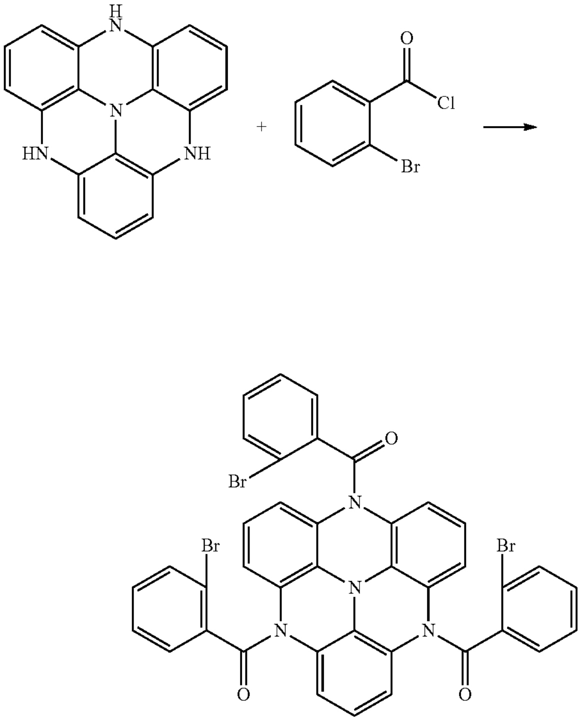

42 g of (150 mmol, 1 equivalent) of 4H,8H, 12H-4,8,12-triaza-12c-boradibenzo[cd,mn]pyrene and 195 ml (194 mmol, 1.3 equivalents) of pyridine are added to 300 ml dry toluene under argon. A solution of 39 g (180 mmol, 1,2 equivalents) of 2-bromobenzoyl chloridine and 100 ml of dry toluene is added slowly at room temperature under argon. The resulting mixture is heated under reflux for 24 hours. After cooling to room temperature, the reaction is diluted with water (50 ml) and extracted with dichloromethane (3x30 ml). The combined organic fractions are washed successively with 1.5 M aqueous HCl, saturated aqueous $Na_2CO_3$ solution and then dried over $Na_2SO_4$ and concentrated under reduced pressure.

The residue is separated by column chromatography with EtOAc/PE (1:5).

The yield is 92 g (110 mmol), corresponding to 75% of the theory.

The following connections can be obtained analogously:
| | Educt 1 | Educt 2 | Product | Yield |
|---|---|---|---|---|
| 1e | 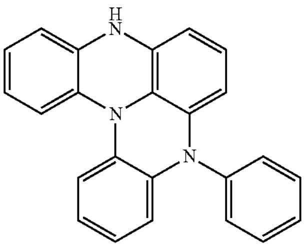 [2101472-60-8] | 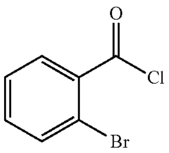 | 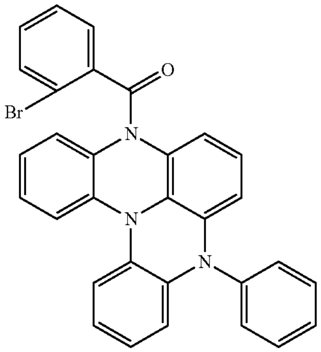 [SMILES: O=C(c1ccccc1Br)N1c2ccccc2N2c3ccccc3N(c3ccccc3)c3cccc1c32] | 77% |
| 2e | 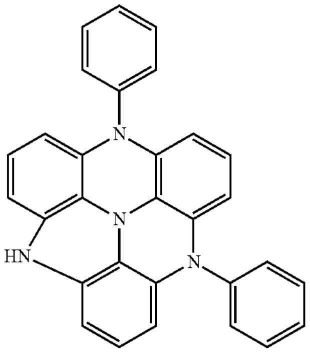 [SMILES: c1ccc(N2c3cccc4c3N3c5c(cccc5N(c5ccccc5)c5cccc2c53)N4)cc1] | 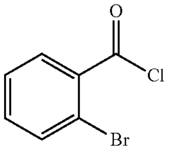 | 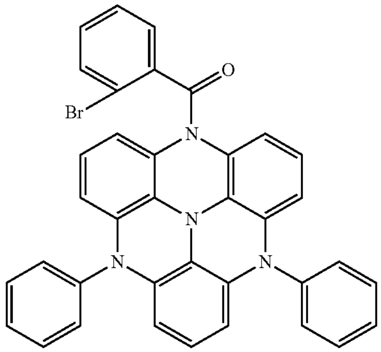 [SMILES: O=C(c1ccccc1Br)N1c2cccc3c2N2c4c1cccc4N(c1ccccc1)c1cccc(c12)N3c1ccccc1] | 80% |
| 3e | 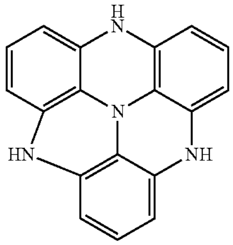 [1694672-52-0] | 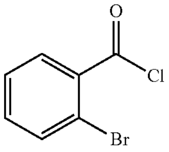 | 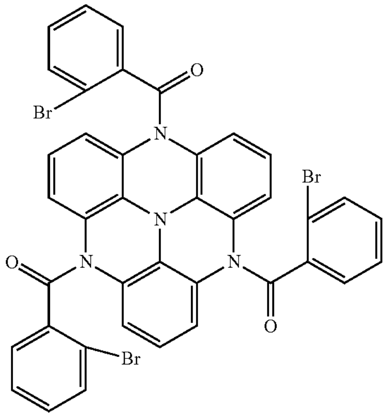 [SMILES: O=C(c1ccccc1Br)N1c2cccc3c2N2c4c1cccc4N(C(=O)c1ccccc1Br)c1cccc(c12)N3C(=O)c1ccccc1Br] | 53% |
| 4e | 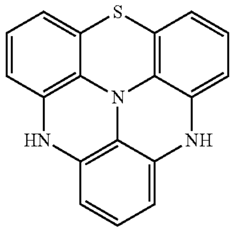 [1694672-62-2] | 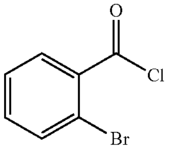 | 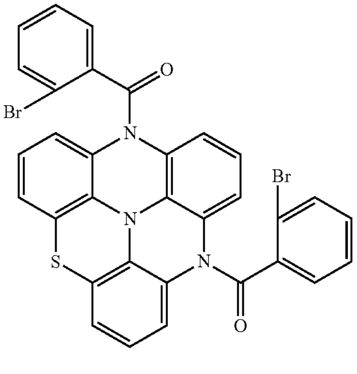 [SMILES: O=C(c1ccccc1Br)N1c2cccc3c2N2c4c(cccc4N(C(=O)c4ccccc4Br)c4cccc1c42)O3] | |

-continued
| | Educt 1 | Educt 2 | Product | Yield |
|---|---|---|---|---|
| 5e | 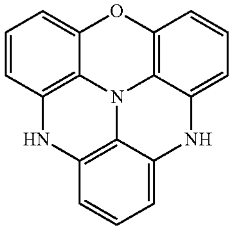 [1694672-60-0] | 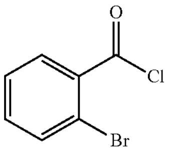 | 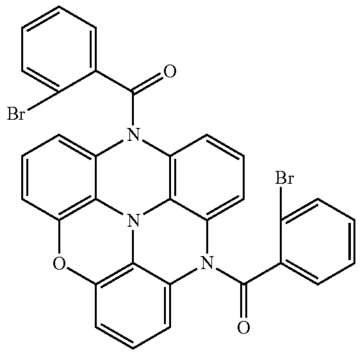 | 62% |
| 6e | 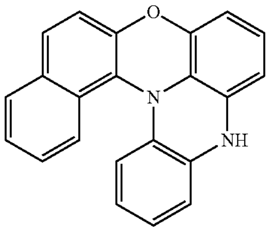 [1694672-40-6] | 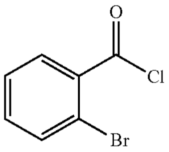 | 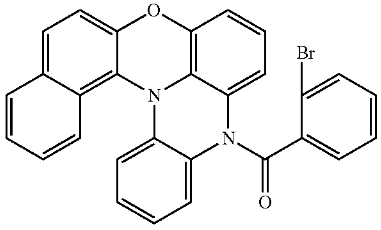 [SMILES: O=C(c1ccccc1Br)N1c2ccccc2N2c3c(cccc31)Oc1ccc3ccccc3c12] | 74% |
| 7e | 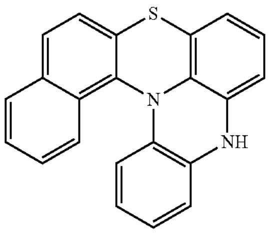 [1694672-48-4] | 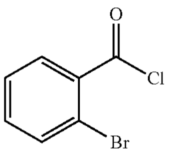 | 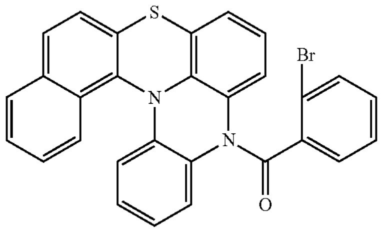 | 76% |
| 8e | 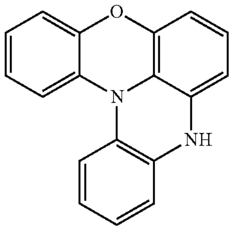 [2055620-82-9] | 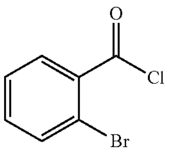 | 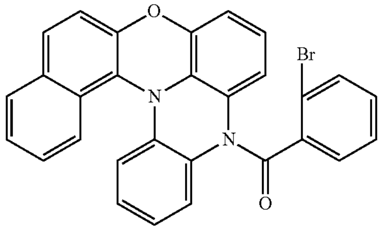 | 81% |
| 9e | 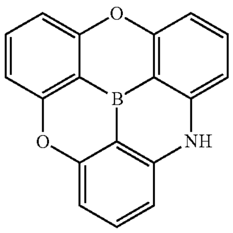 [2088305-62-6] | 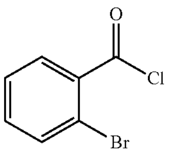 | 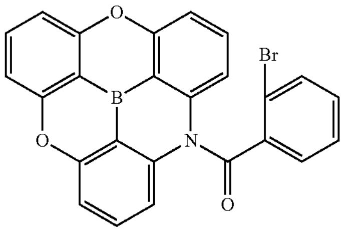 [SMILES: O=C(c1ccccc1Br)N1c2cccc3c2B2c4c(cccc4Oc4cccc1c42)O3] | 80% |

-continued

| | Educt 1 | Educt 2 | Product | Yield |
|---|---|---|---|---|
| 10e | 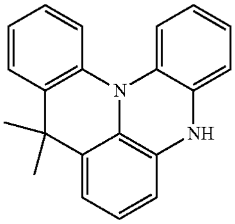 [2032395-59-6] | 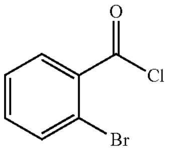 | 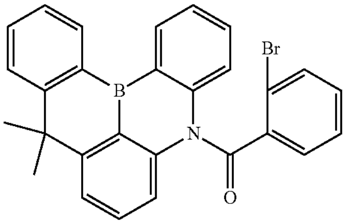 [SMILES: CC1(C)c2ccccc2B2c3ccccc3N(C(=O)c3ccccc3Br)c3cccc1c32] | 87% |

f) Ring Closure

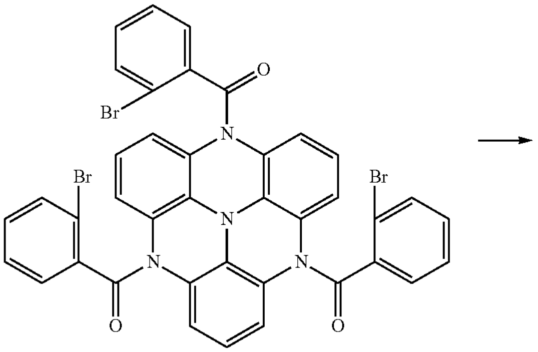

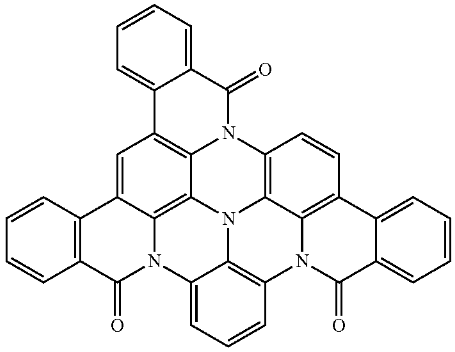

A

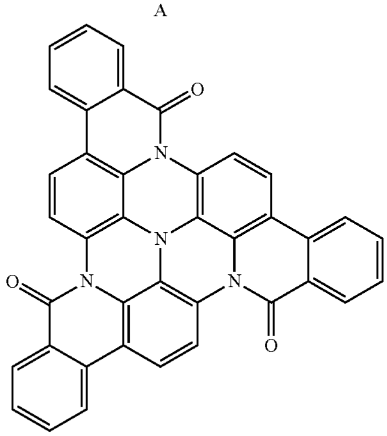

B

-continued

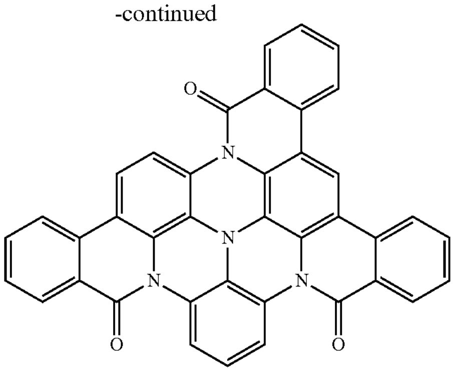

C 172 ml of tributyltin hydride (64 mmol) and 120 g (50 mmol) of 1,1'-azobis(cyclohexane-1-carbonitrile) in 2000 ml of toluene are added dropwise under inert gas over a period of 4 hours in a boiling solution of 41.6 g (50 mmol) of a compound (e) in 1000 ml of toluene. The mixture is boiled during 3 hours under reflux. Afterwards, the reaction mixture is poured on ice and extracted three times with dichloromethane. The combined organic phases are dried over $Na_2SO_4$ and concentrated. The three products are separated by column chromatography and recrystallized from toluene/dichloromethane and finally sublimated in high vacuum.

The yield is 18.8 g (31 mmol) of the mixture A+B+C, corresponding to 64% of the theory. After column chromatographic separation: 15% A, 31% B and 14% C are obtained.

The following compounds can be obtained analogously:
| | Educt | Product | Yield |
|---|---|---|---|
| 1f | 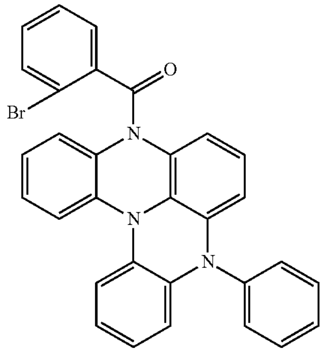 [SMILES: O=C(c1ccccc1Br)N1c2ccccc2N2c3ccccc3N(c3ccccc3)c3cccc1c32] | 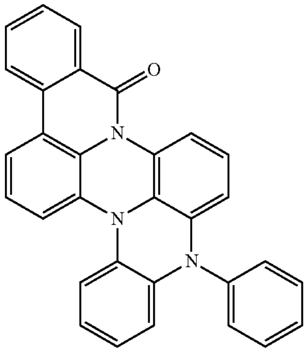<br>A<br>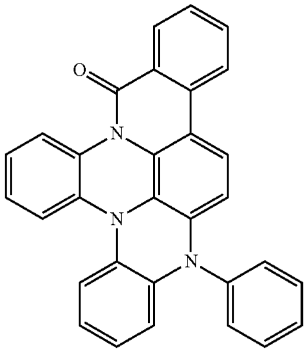<br>B | A 25%,<br>B 27% |
| 2f | 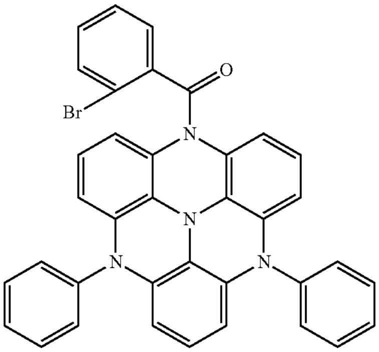 [SMILES: O=C(c1ccccc1Br)N1c2cccc3c2N2c4c1cccc4N(c1ccccc1)c1cccc(c12)N3c1ccccc1] | 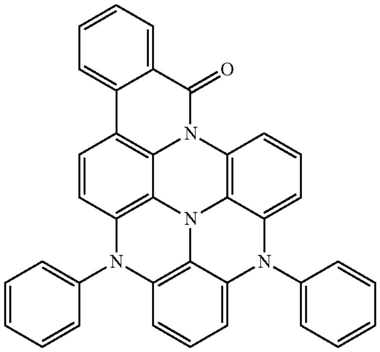<br>A | A 51% |

-continued
| | Educt | Product | Yield |
|---|---|---|---|
| 3f | 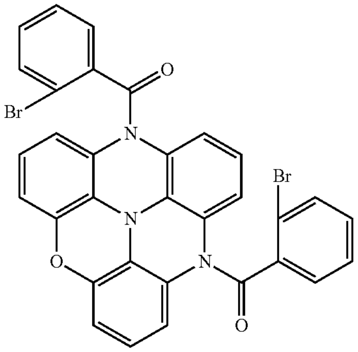 | 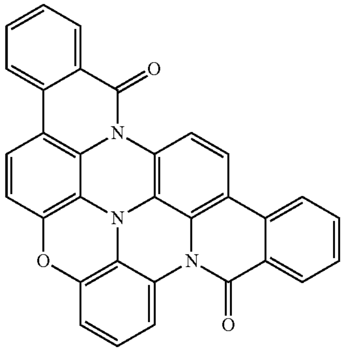<br>A<br>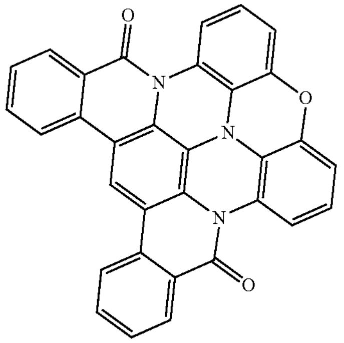<br>B<br>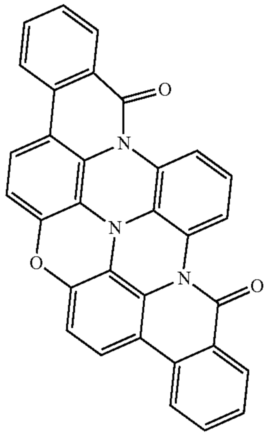<br>C | A 27%, B 22%, C 32% |

-continued
| | Educt | Product | Yield |
|---|---|---|---|
| 4f | 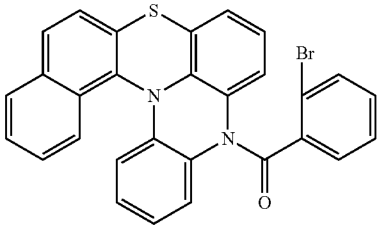 [SMILES: O=C(c1ccccc1Br)N1c2ccccc2N2c3c(cccc31)Sc1ccc3ccccc3c12] | 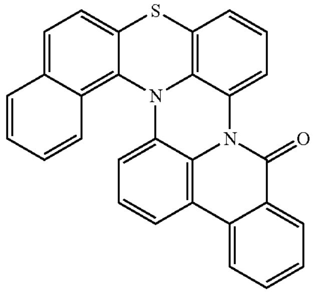 A | A 37%, B 21% |
| | | 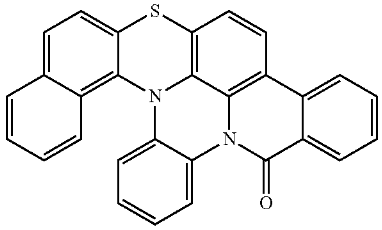 B | |
| 5f | 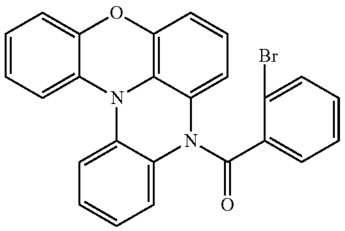 [SMILES: O=C(c1ccccc1Br)N1c2ccccc2N2c3ccccc3Oc3cccc1c32] | 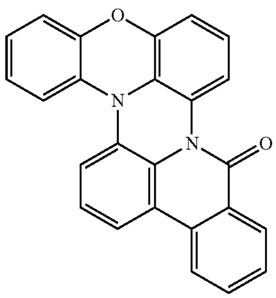 A | A 40%, B 22% |
| | | 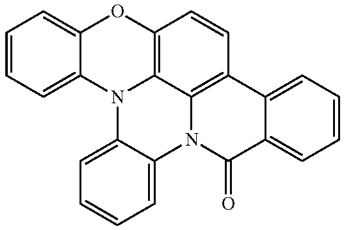 B | |
| 6f | 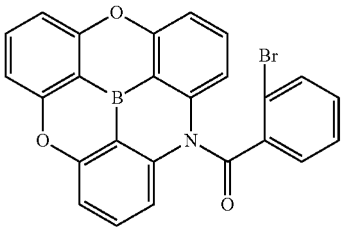 [SMILES: O=C(c1ccccc1Br)N1c2cccc3c2B2c4c(cccc4Oc4cccc1c42)O3] | 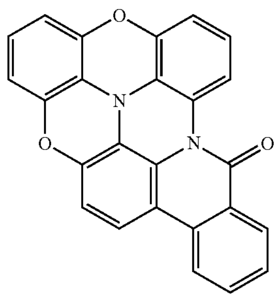 A | A 31%, |

-continued

| | Educt | Product | Yield |
|---|---|---|---|
| 7f | 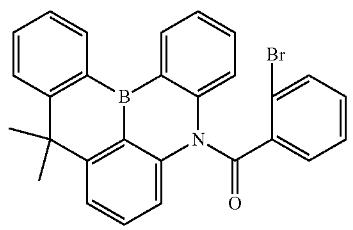 [SMILES: CC1(C)c2ccccc2B2c3ccccc3N(C(=O)c3ccccc3Br)c3cccc1c32] | 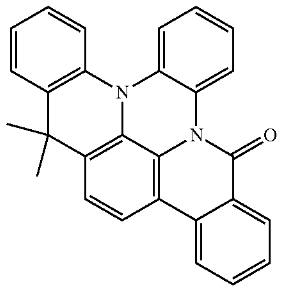<br>A<br>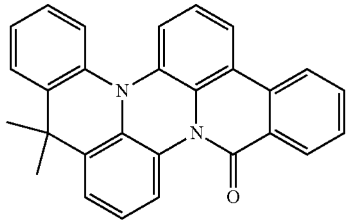<br>B | A 35%,<br>B 27% |

B) Fabrication of OLEDs

The fabrication of OLEDs is based on a process, which is described for example in WO 04/058911, and which is adapted to the individual conditions (e.g. layer thickness variation to achieve optimum efficiency or color).

In the following examples E1 to E12, the results of different OLEDs comprising compounds according to the invention are presented. Glass plates coated with structured ITO (indium tin oxide) form the substrates of the OLEDs. In principle, the OLEDs have the following layer structure: substrate/hole injection layer (HIL)/hole transport layer (HTL1) 60 nm/hole transport layer (HTL2) 20 nm/emission layer (EML) 30 nm/electron transport layer (ETL) 20 nm and finally a cathode. All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. The cathode is formed by a 1 nm thin LiF layer and a 100 nm Al layer deposited on it. Table 1 shows the chemical structures of the materials used to build OLEDs.

The OLEDs are characterized by standard methods. For this purpose, the electroluminescence spectra, efficiency (measured in cd/A), power efficiency (measured in lm/W), determined as a function of luminance, calculated from current-voltage-luminance characteristics assuming a Lambertian radiation characteristic, voltage (V) and lifetime are determined. The electroluminescence spectra are determined at a brightness of 1000 cd/$m^2$ and the CIE 1931 x and y colour coordinates are determined. The lifetime is defined as the time after which the initial brightness of 6000 cd/$m^2$ (for blue emitting OLEDs) or 25000 cd/$m^2$ (for green emitting OLEDs) has been divided by two.

Table 2 and 3 summarize the results of some OLEDs (examples E1 to E12 according to the invention and comparative example E13). The examples E1, E2 and E3 comprise compounds according to the invention, which are used green fluorescent emitters.

E4 to E12 comprise compounds according to the invention, which are used as blue emitter materials. As a comparative example, the compound D13 in E13 is used according to the state of the art.

As can be seen from the results summarized in Table 3, OLEDs comprising compound according to the invention have a significantly improved lifetime compared to state-of-the-art OLEDs. Furthermore, with deep blue color coordinates, a comparable or higher efficiency is achieved compared to the state of the art.

TABLE 1
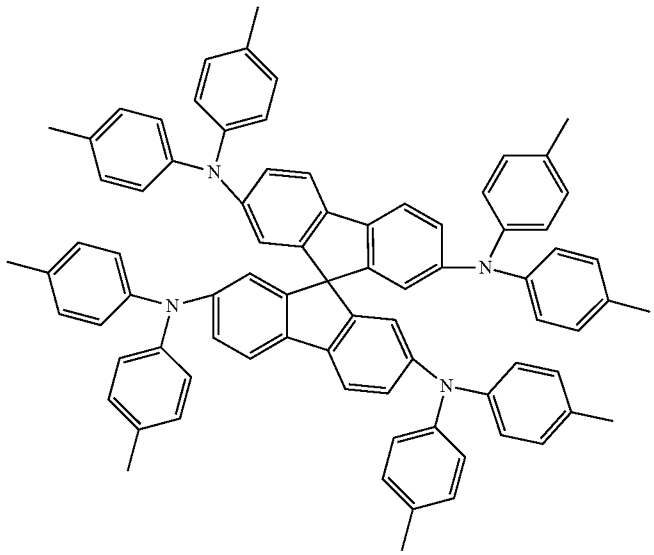
HTM1
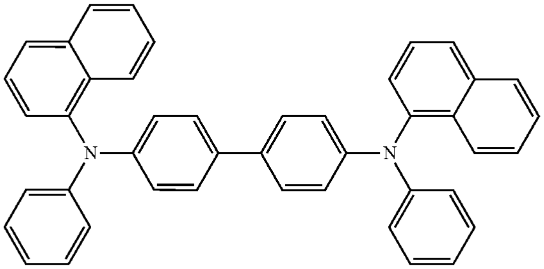 [SMILES: c1ccc(N(c2ccc(-c3ccc(N(c4ccccc4)c4cccc5ccccc45)cc3)cc2)c2cccc3ccccc23)cc1]
HTM2
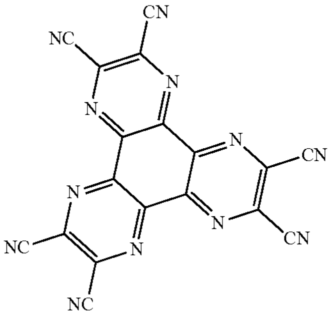 [SMILES: N#Cc1nc2c3nc(C#N)c(C#N)nc3c3nc(C#N)c(C#N)nc3c2nc1C#N]
HIM
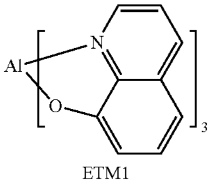
ETM1

TABLE 1-continued
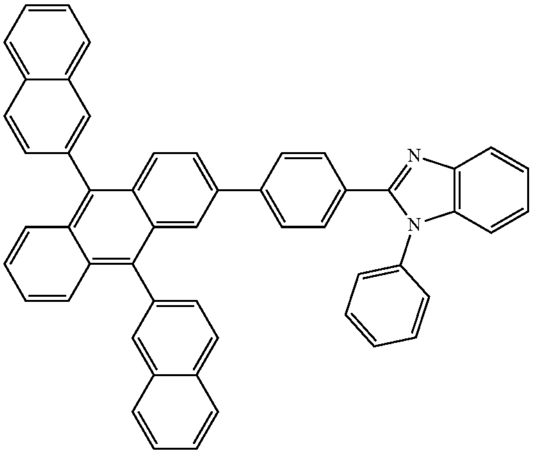 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM2
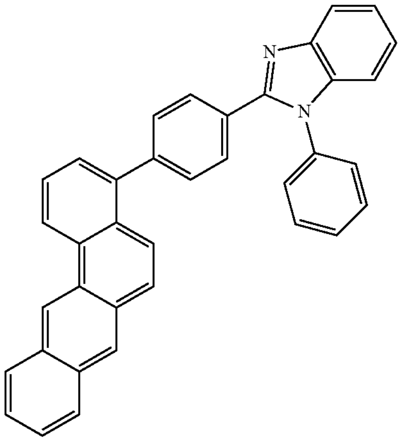 [SMILES: c1ccc(-n2c(-c3ccc(-c4cccc5c4ccc4cc6ccccc6cc45)cc3)nc3ccccc32)cc1]
ETM3
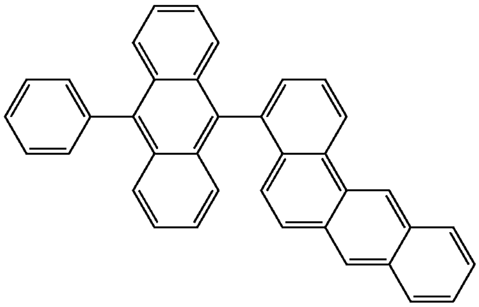 [SMILES: c1ccc(-c2c3ccccc3c(-c3cccc4c3ccc3cc5ccccc5cc34)c3ccccc23)cc1]
H2
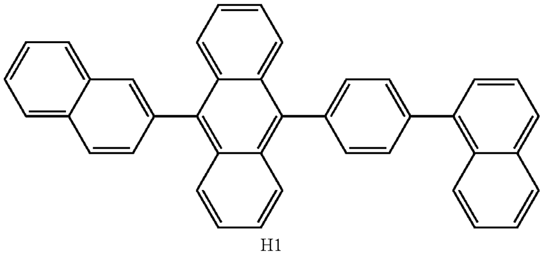
H1

TABLE 1-continued
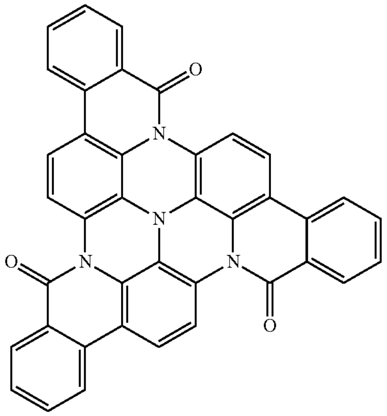 [SMILES: O=c1c2ccccc2c2ccc3c4c2n1c1ccc2c5ccccc5c(=O)n5c6ccc7c8ccccc8c(=O)n3c7c6n4c1c25]
D1 (fB)
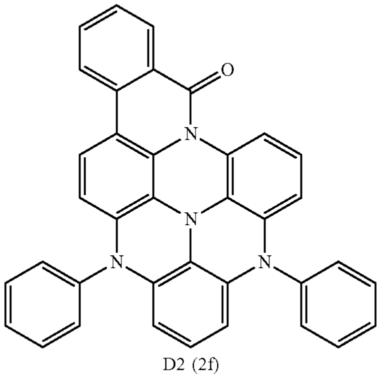
D2 (2f)
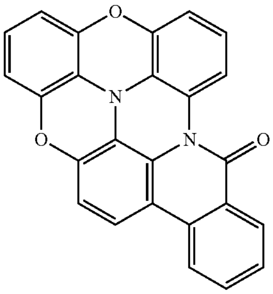 [SMILES: O=c1c2ccccc2c2ccc3oc4cccc5oc6cccc7c6-n(c54)c3c2n17]
D3 (6f)
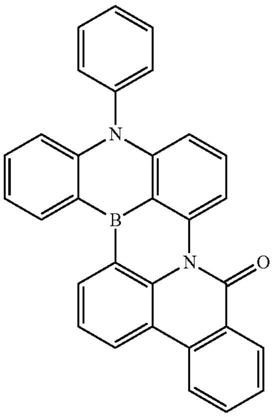 [SMILES: O=c1c2ccccc2c2cccc3c2n1-c1cccc2c1B3c1ccccc1N2c1ccccc1]
D4 (d)

TABLE 1-continued
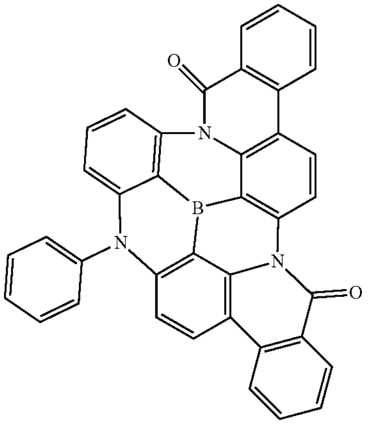 [SMILES: O=c1c2ccccc2c2ccc3c4c2n1-c1ccc2c5ccccc5c(=O)n5c2c1B4c1c(cccc1-5)N3c1ccccc1]
D5 (6d)
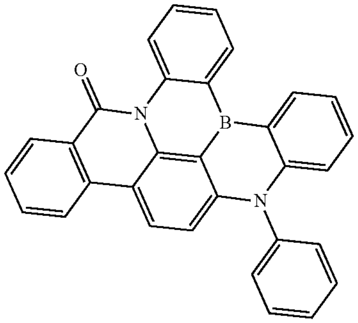 [SMILES: O=c1c2ccccc2c2ccc3c4c2n1-c1ccccc1B4c1ccccc1N3c1ccccc1]
D6 (4d)
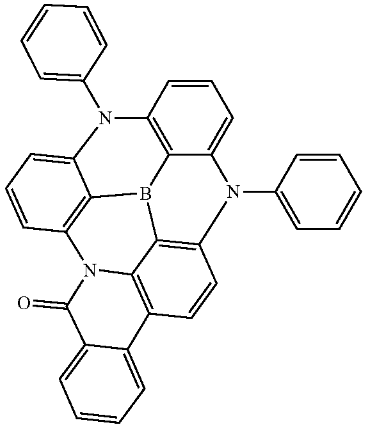 [SMILES: O=c1c2ccccc2c2ccc3c4c2n1-c1cccc2c1B4c1c(cccc1N3c1ccccc1)N2c1ccccc1]
D7 (1d)
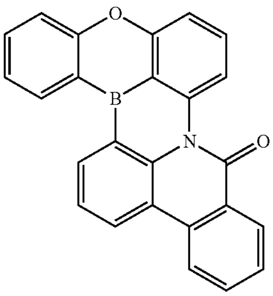 [SMILES: O=c1c2ccccc2c2cccc3c2n1-c1cccc2c1B3c1ccccc1O2]
D8 (8d)

TABLE 1-continued
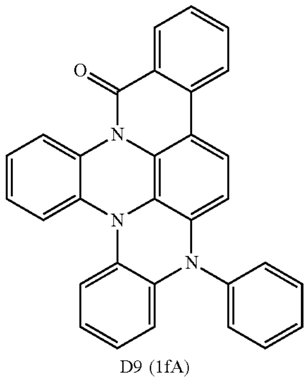
D9 (1fA)
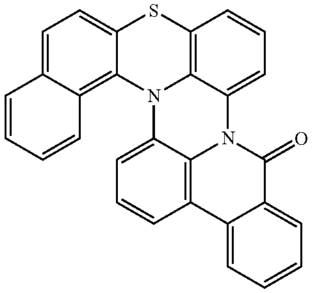 [SMILES: O=c1c2ccccc2c2cccc3c2n1c1cccc2sc4ccc5ccccc5c4n3-c21]
D10 (4fA)
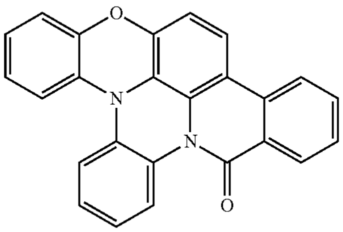 [SMILES: O=c1c2ccccc2c2ccc3c4c2n1-c1ccccc1N4c1ccccc1O3]
D11 (5fB)
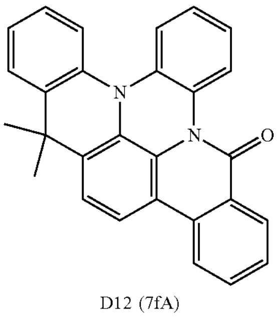
D12 (7fA)

TABLE 1-continued

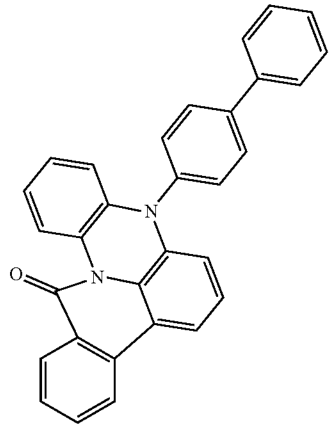 [SMILES: O=c1c2ccccc2c2cccc3c2n1-c1ccccc1N3c1ccc(-c2ccccc2)cc1]

D13 (WO2011/137951)

TABLE 2

| | EML | ETM | color | Efficiency (cd/A) at 1000 cd/m$^2$ | Voltage (V) at 1000 cd/m$^2$ | CIE | Lifetime (h) at 25000 cd/m$^2$ |
|---|---|---|---|---|---|---|---|
| E1 | H1 + 9% D1 | ETM2 | green | 16.2 | 4.4 | x = 0.28/ y = 0.61 | 348 |
| E2 | H1 + 9% D2 | ETM2 | green | 16.0 | 4.5 | x = 0.29/ y = 0.61 | 345 |
| E3 | H1 + 9% D3 | ETM2 | green | 15.4 | 4.8 | x = 0.29/ y = 0.60 | 350 |

TABLE 3

| | EML | ETM | color | Efficiency (cd/A) at 1000 cd/m$^2$ | Voltage (V) at 1000 cd/m$^2$ | CIE | Lifetime (h) at 6000 cd/m$^2$ |
|---|---|---|---|---|---|---|---|
| E4 | H1 + 5% D4 | ETM1 | blau | 4.7 | 5.0 | x = 0.15/ y = 0.16 | 770 |
| E5 | H2 + 5% D5 | ETM1 | blau | 4.6 | 5.1 | x = 0.16/ y = 0.13 | 640 |
| E6 | H2 + 5% D6 | ETM1 | blau | 4.5 | 5.2 | x = 0.16/ y = 0.10 | 660 |
| E7 | H2 + 5% D7 | ETM1 | blau | 4.6 | 5.2 | x = 0.16/ y = 0.13 | 641 |
| E8 | H2 + 5% D8 | ETM1 | blau | 4.7 | 4.3 | x = 0.16/ y = 0.12 | 658 |
| E9 | H1 + 5% D9 | ETM3 | blau | 5.3 | 4.5 | x = 0.15/ y = 0.16 | 790 |
| E10 | H2 + 5% D10 | ETM3 | blau | 6.2 | 4.8 | x = 0.16/ y = 0.17 | 770 |
| E11 | H1 + 5% D11 | ETM3 | blau | 6.1 | 4.2 | x = 0.16/ y = 0.15 | 680 |
| E12 | H2 + 5% D12 | ETM3 | blau | 6.40 | 4.4 | x = 0.16/ y = 0.15 | 710 |
| E13 comp | H2 + 5% D13 | ETM3 | blau | 4.0 | 5.7 | x = 0.16/ y = 0.16 | 450 |

The invention claimed is:

1. A compound of formula (1), formula (1)

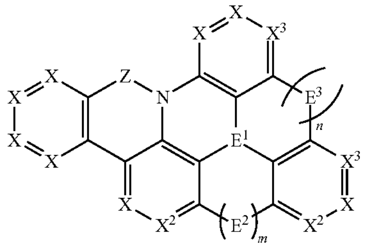

where the following applies to the symbols and indices used:

Z stands, on each occurrence, identically or differently, for C═O, C═S, C═NR, BR, SO or $SO_2$;

$E^1$ stands for N, B, P or P═O;

$E^2$, $E^3$ stand, on each occurrence, identically or differently, for a single bond or for a divalent bridge selected from $B(R^0)$, $N(R^N)$, $C(R^0)_2$, $Si(R^0)_2$, C═O, C═NRN, $C{=}C(R^0)_2$, O, S, S═O, $SO_2$, $P(R^0)$ or $P(=O)R^0$; or a group $E^2$ forms a lactam ring (L-1) as depicted below with one group $X^2$, or a group $E^3$ forms a lactam ring (L-1) with one group $X^3$;

(L-1)

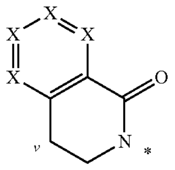

where the sign "v" indicates the position of the group $X^2$ or $X^3$, which stands for C in this case, and the N atom marked with the sign "*" corresponds to $E^2$ or $E^3$;

X stands, on each occurrence, identically or differently, for $CR^1$ or N;

$X^2$, $X^3$ stand, on each occurrence, identically or differently, for X;

$R^0$, $R^1$, $R^N$ stand on each occurrence, identically or differently, for H, D, F, Cl, Br, I, CHO, CN, C(═O)Ar, $P(=O)(Ar)_2$, $S(=O)Ar$, $S(=O)_2Ar$, $N(R)_2$, $N(Ar)_2$, $NO_2$, $Si(R)_3$, $B(OR)_2$, $OSO_2R$, a straight-chain alkyl, alkoxy or thioalkyl group having 1 to 40 C atoms or branched or a cyclic alkyl, alkoxy or thioalkyl group having 3 to 40 C atoms, each of which may be substituted by one or more radicals R, where in each case one or more non-adjacent $CH_2$ groups may be replaced by RC=CR, C≡C, $Si(R)_2$, $Ge(R)_2$, $Sn(R)_2$, C=O, C=S, C=Se, P(=O)(R), SO, $SO_2$, O, S or CONR and where one or more H atoms may be replaced by D, F, Cl, Br, I, CN or $NO_2$, an aromatic or heteroaromatic ring system having 5 to 60 aromatic ring atoms, which may in each case be substituted by one or more radicals R, an aralkyl or heteroaralkyl group having 5 to 60 aromatic ring atoms, which may be substituted by one or more R radicals, or an aryloxy or heteroaryloxy group having 5 to 60 aromatic ring atoms, which may be substituted by one or more radicals R; where two radicals $R^0$, $R^1$, $R^N$ may form an aliphatic, aromatic or heteroaromatic ring system together, which may be substituted by one or more radicals R;

R stands on each occurrence, identically or differently, for H, D, F, Cl, Br, I, CHO, CN, C(=O)Ar, $P(=O)(Ar)_2$, S(=O)Ar, $S(=O)_2Ar$, $N(R')_2$, $N(Ar)_2$, $NO_2$, $Si(R')_3$, $B(OR')_2$, $OSO_2R'$, a straight-chain alkyl, alkoxy or thioalkyl group having 1 to 40 C atoms or branched or a cyclic alkyl, alkoxy or thioalkyl group having 3 to 40 C atoms, each of which may be substituted by one or more radicals R', where in each case one or more non-adjacent $CH_2$ groups may be replaced by R'C=CR', C=C, $Si(R')_2$, $Ge(R')_2$, $Sn(R')_2$, C=O, C=S, C=Se, P(=O)(R'), SO, $SO_2$, O, S or CONR and where one or more H atoms may be replaced by D, F, Cl, Br, I, CN or $NO_2$, an aromatic or heteroaromatic ring system having 5 to 60 aromatic ring atoms, which may in each case be substituted by one or more radicals R'; where two substituents R may form an aliphatic or aromatic ring system together, which may be substituted by one or more radicals R';

Ar is, on each occurrence, identically or differently, an aromatic or heteroaromatic ring system having 5 to 60 aromatic ring atoms, which may in each case also be substituted by one or more radicals R';

R' stands on each occurrence, identically or differently, for H, D, F, Cl, Br, I, CN, a straight-chain alkyl, alkoxy or thioalkyl group having 1 to 20 C atoms or branched or cyclic alkyl, alkoxy or thioalkyl group having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 aromatic ring atoms;

m, n are, identically or differently, 0 or 1; with the proviso that m+n=1 or 2, and when m is 0, then $E^2$ is absent and a group X is present at each bonding site of $E^2$, and when n is 0, then $E^3$ is absent and a group X is present at each bonding site of $E^3$; and wherein at least one of the following is true:

(i) $E^1$ is P or P=O;

(ii) Z is C=O, C=S, C=NR, SO, or $SO_2$;

(iii) at least one of $E^2$ or $E^3$ is $C(R^0)_2$, $Si(R^0)_2$, C=O, C=NRN $C=C(R^0)_2$, S=O, $SO_2$, $P(R^0)$ or $P(=O)R^0$;

(iv) Z is BR and R is not joined to form an aliphatic, aromatic, or heteroaromatic ring system; or (v) $E^2$ forms a lactam ring (L-1) with one group $X^2$, or a group $E^3$ forms a lactam ring (L-1) with one group $X^3$.

2. The compound according to claim 1, wherein the compound of formula (1) comprises at least one group $E^2$ or $E^3$, which stands for a divalent bridge selected from $B(R^0)$, $N(R^N)$, $C(R^0)_2$, $Si(R^0)_2$, C=O, C=NRN, $C=C(R^0)_2$, O, S, S=O, $SO_2$, $P(R^0)$ or $P(=O)R^0$; or at least one group $E^2$ or $E^3$ forms a lactam ring (L-1) with one group $X^2$ or one group $X^3$.

3. The compound according to claim 1, wherein the compound is selected from compounds of formula (1A) or (1B), formula (1A)

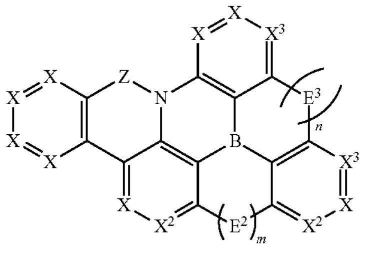

formula (1B)

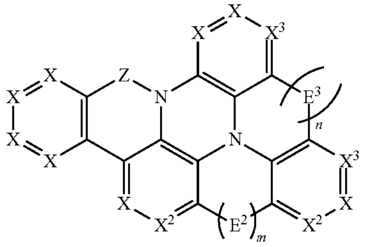

4. The compound according to claim 1, wherein Z stands, on each occurrence, identically or differently, for C=O or C=S.

5. The compound according to claim 1, wherein the compound is selected from compounds of formula (2A) or (2B), formula (2A)

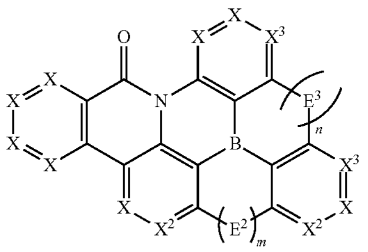

-continued formula (2B)

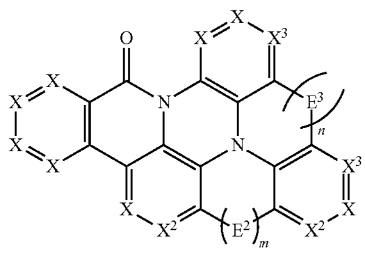

6. The compound according to claim 1, wherein the compound is selected from compounds of formulae (2A-1) to (2B-3), formula (2A-1)

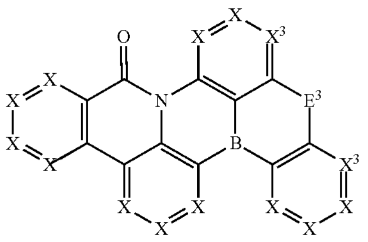

formula (2A-2)

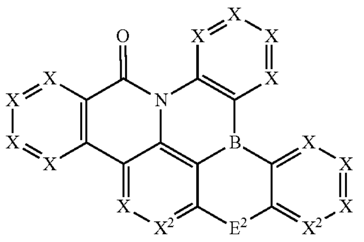

formula (2A-3)

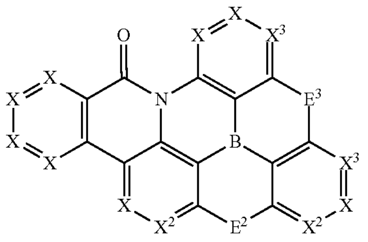

formula (2B-1)

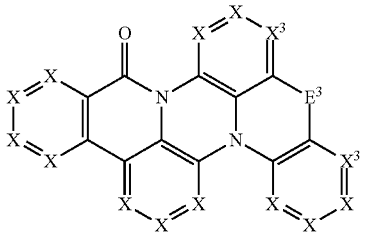

-continued formula (2B-2)

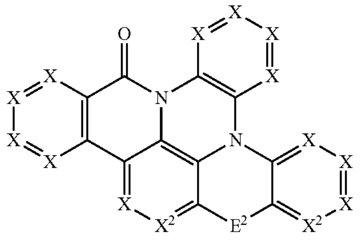

formula (2B-3)

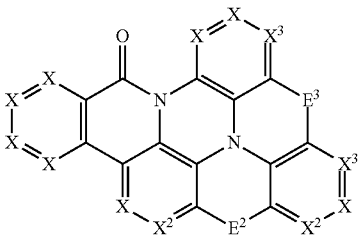

7. The compound according to claim 1, wherein the groups $E^2$ and $E^3$ stand, on each occurrence, identically or differently, for a divalent bridge selected from $B(R^0)$, $N(R^N)$, $C(R^0)_2$, O or S, or a group $E^2$ forms a lactam ring (L-1) with a group $X^2$, or a group $E^3$ forms a lactam ring (L-1) with a group $X^3$; or wherein the compound comprises at least one group $E^2$ or $E^3$, which stands for a divalent bridge selected from $N(R^N)$, or which forms a lactam ring (L-1) with a group $X^2$ or $X^3$.

8. The compound according to claim 1, wherein the compound is selected from compounds of formulae (2A-1-1) to (2-A-3-6), formula (2A-1-1)

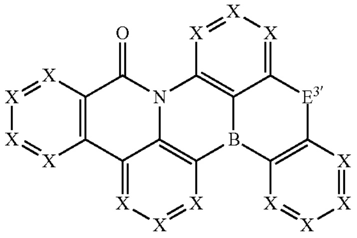

formula (2A-1-2)

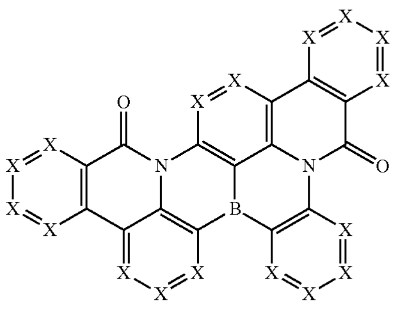

-continued
formula (2A-1-3)
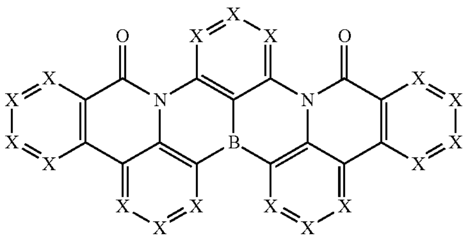
formula (2A-2-1)
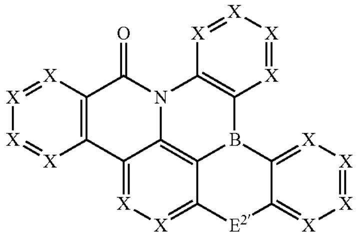
formula (2A-2-2)
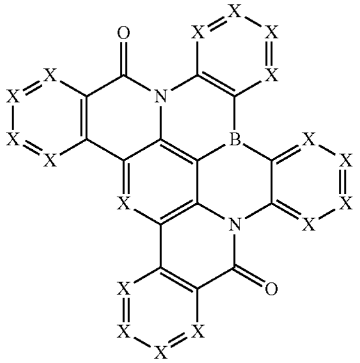
formula (2A-2-3)
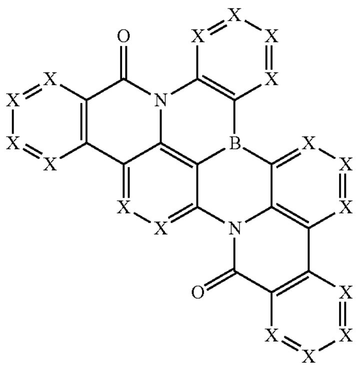
formula (2A-3-1)
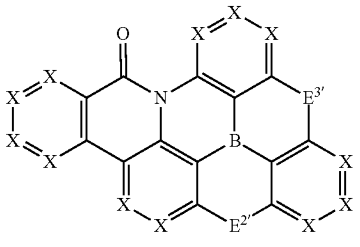
-continued
formula (2A-3-2)
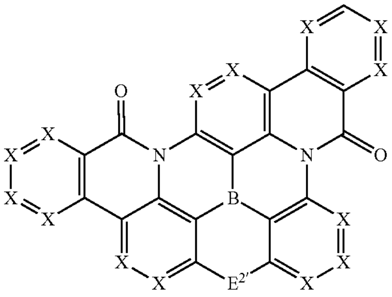
formula (2A-3-3)
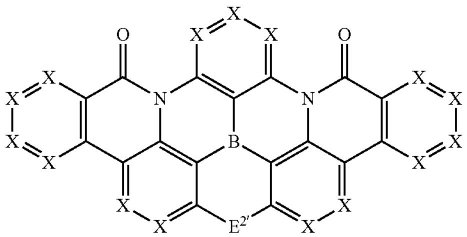
formula (2A-3-4)
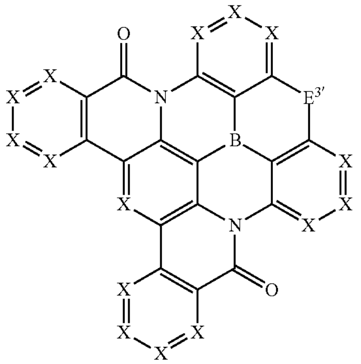
formula (2A-3-5)
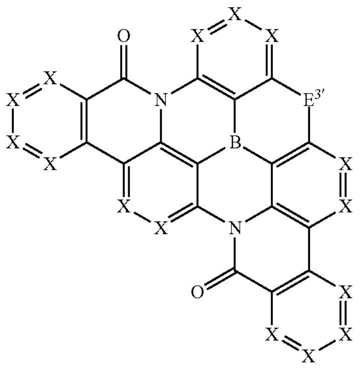

-continued
formula (2A-3-6)
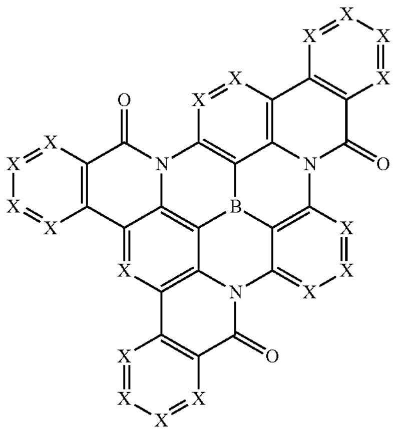
formula (2B-1-1)
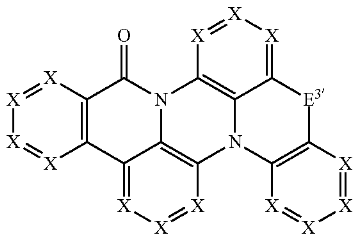
formula (2B-1-2)
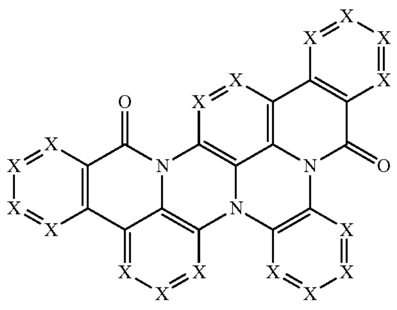
formula (2B-1-3)
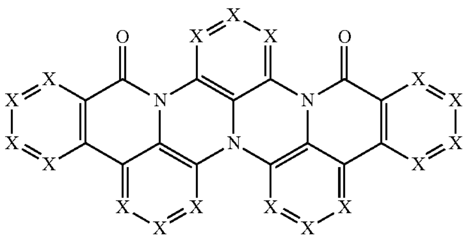
formula (2B-2-1)
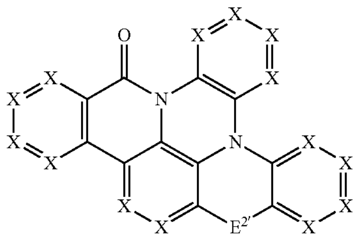
-continued
formula (2B-2-2)
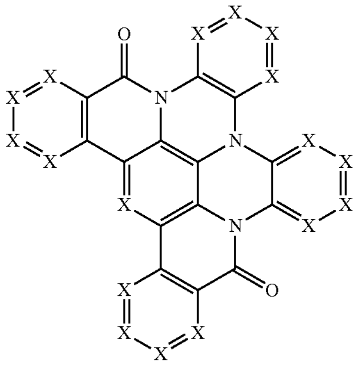
formula (2B-2-3)
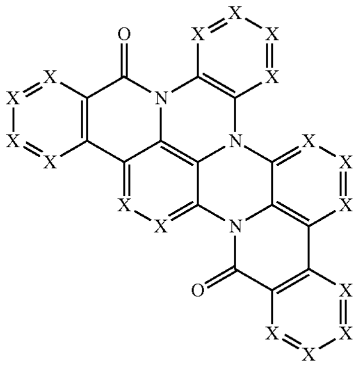
formula (2B-3-1)
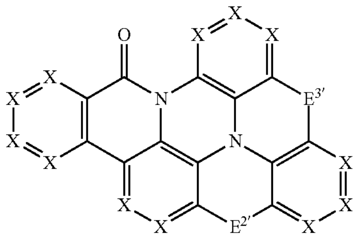
formula (2B-3-2)
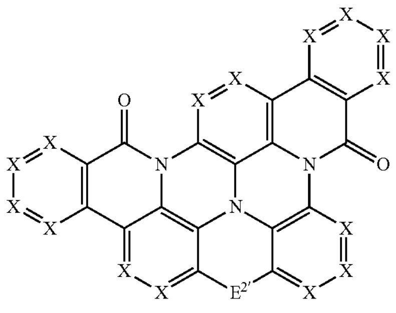
formula (2B-3-3)
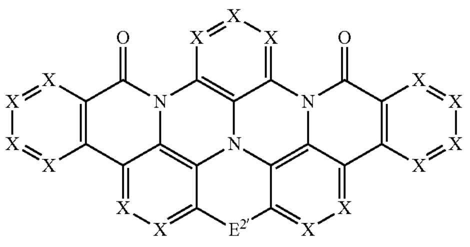

-continued formula (2B-3-4)

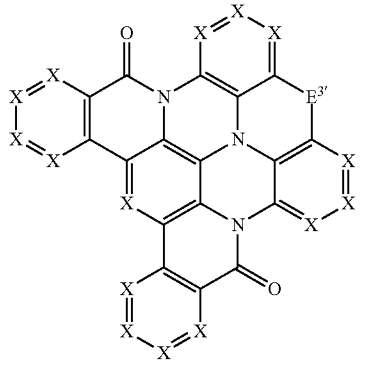

formula (2B-3-5)

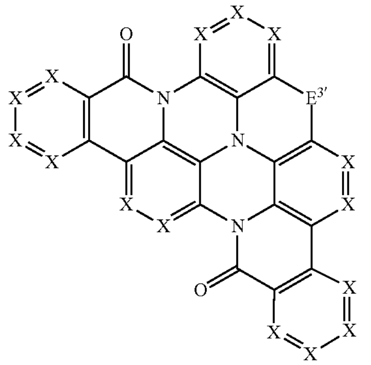

formula (2B-3-6)

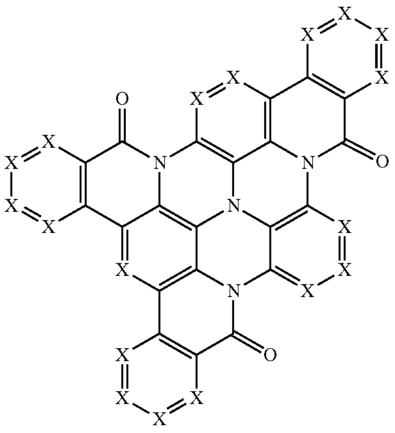

where $E^{2'}$, $E^{3'}$ stand, on each occurrence, identically or differently, for a single bond or for a divalent bridge selected from $B(R^0)$, $N(R^N)$, $C(R^0)_2$, $Si(R^0)_2$, C═O, C═NRN, $C{=}C(R^0)_2$, O, S, S═O, $SO_2$, $P(R^0)$ or $P({=}O)R^0$.

9. The compound according to claim 8, wherein $E^{2'}$, $E^{3'}$ stand, on each occurrence, identically or differently, for a divalent bridge selected from $B(R^0)$, $N(R^N)$, $C(R^0)_2$, O or S.

10. The compound according to claim 1, wherein the compound comprises at least one radical $R^0$, $R^1$, $R^N$ or R selected from:

branched or cyclic alkyl groups represented by the general following formula a group of formula (RS-a), (RS-a)

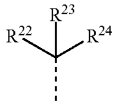

wherein $R^{22}$, $R^{23}$, $R^{24}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{25}$, and where two of radicals $R^{22}$, $R^{23}$, $R^{24}$ or all radicals $R^{22}$, $R^{23}$, $R^{24}$ may be joined to form a (poly)cyclic alkyl group, which may be substituted by one or more radicals $R^{25}$, $R^{25}$ is at each occurrence, identically or differently, selected from a straight-chain alkyl group having 1 to 10 carbon atoms, or a branched or cyclic alkyl group having 3 to 10 carbon atoms;

with the proviso that at each occurrence at least one of radicals $R^{22}$, $R^{23}$ and $R^{24}$ is other than H, with the proviso that at each occurrence all of radicals $R^{22}$, $R^{23}$ and $R^{24}$ together have at least 4 carbon atoms and with the proviso that at each occurrence, if two of radicals $R^{22}$, $R^{23}$, $R^{24}$ are H, the remaining radical is not a straight-chain; or branched or cyclic alkoxy groups represented by the general following formula (RS-b)

(RS-b)

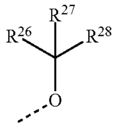

wherein $R^{26}$, $R^{27}$, $R^{28}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{25}$ as defined above, and where two of radicals $R^{26}$, $R^{27}$, $R^{28}$ or all radicals $R^{26}$, $R^{27}$, $R^{28}$ may be joined to form a (poly)cyclic alkyl group, which may be substituted by one or more radicals $R^{25}$ as defined above;

with the proviso that at each occurrence only one of radicals $R^{26}$, $R^{27}$ and $R^{28}$ may be H;

aralkyl groups represented by the general following formula (RS-c)

(RS-c)

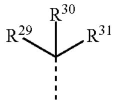

wherein $R^{29}$, $R^{30}$, $R^{31}$ are at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{32}$, or an aromatic ring system having 6 to 30 aromatic ring atoms, which may in each case be substituted by one or more radicals $R^{32}$, and where two or all of radicals $R^{29}$, $R^{30}$, $R^{31}$ may be joined to form a (poly)cyclic alkyl group or an aromatic ring system, each of which may be substituted by one or more radicals $R^{32}$;

$R^{32}$ is at each occurrence, identically or differently, selected from a straight-chain alkyl group having 1 to 10 carbon atoms, or a branched or cyclic alkyl group having 3 to 10 carbon atoms, or an aromatic ring system having 6 to 24 aromatic ring atoms;

with the proviso that at each occurrence at least one of radicals $R^{29}$, $R^{30}$ and $R^{31}$ is other than H and that at each occurrence at least one of radicals $R^{29}$, $R^{30}$ and $R^{31}$ is or contains an aromatic ring system having at least 6 aromatic ring atoms;

aromatic ring systems represented by the general formula (RS-d)

(RS-d)

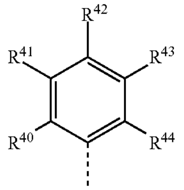

wherein $R^{40}$ to $R^{44}$ is at each occurrence, identically or differently, selected from H, a straight-chain alkyl group having 1 to 10 carbon atoms, or a branched or cyclic alkyl group having 3 to 10 carbon atoms, where the above-mentioned groups may each be substituted by one or more radicals $R^{32}$, or an aromatic ring system having 6 to 30 aromatic ring atoms, which may in each case be substituted by one or more radicals $R^{32}$, and where two or more of radicals $R^{40}$ to $R^{44}$ may be joined to form a (poly)cyclic alkyl group or an aromatic ring system, each of which may be substituted by one or more radicals $R^{32}$ as defined above; or groups of formula (RS-e), formula (RS-e)

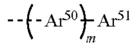

where the dashed bond in formula (RS-e) indicates the bonding to the compound, where $Ar^{50}$, $Ar^{51}$ stand on each occurrence, identically or differently, for an aromatic or heteroaromatic ring systems having 5 to 60 aromatic ring atoms, which may in each case be substituted by one or more radicals R; and where m is an integer selected from 1 to 10.

11. A polymer, oligomer or dendrimer containing one or more compounds according to claim 1, where the bond(s) to the polymer, oligomer or dendrimer may be localised at any positions in formula (1) which is substituted by $R^0$, $R^1$, $R^N$ or R.

12. A formulation comprising at least one compound according to claim 1 and at least one solvent.

13. An electronic device comprising at least one compound according to claim 1, selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

14. An organic electroluminescent device comprising at least one compound according to claim 1, wherein the compound is employed as an emitter in an emitting layer.

15. The organic electroluminescent device according to claim 14, wherein at least one of the following is true:

the compound is employed as a fluorescent emitter in an emitting layer, wherein the emitting layer comprises at least one further component selected from matrix materials; or the compound is employed as an emitter showing Thermally Activated Delayed Fluorescence in an emitting layer, wherein the emitting layer comprises at least one further component selected from matrix materials; or the compound is employed as a fluorescent emitter in an emitting layer, wherein the emitting layer comprises at least one sensitizer selected from phosphorescent compounds and thermally activated delayed fluorescence compounds.

16. The compound according to claim 1, wherein $E^1$ is P or P=O.

17. The compound according to claim 1, wherein Z is C=O, C=S, C=NR, SO, or $SO_2$.

18. The compound according to claim 1, wherein at least one of $E^2$ or $E^3$ is $C(R^0)_2$, $Si(R^0)_2$, C=O, C=NRN, $C=C(R^0)_2$, S=O, $SO_2$, $P(R^0)$ or $P(=O)R^0$.

19. The compound according to claim 1, wherein Z is BR and R is not joined to form an aliphatic, aromatic, or heteroaromatic ring system.

20. The compound according to claim 1, wherein $E^2$ forms a lactam ring (L-1) with one group $X^2$, or a group $E^3$ forms a lactam ring (L-1) with one group $X^3$.

* * * * *